(12) United States Patent
Saadat et al.

(10) Patent No.: US 11,376,028 B1
(45) Date of Patent: Jul. 5, 2022

(54) DEVICES, SYSTEMS, AND METHODS FOR REMOVING OBSTRUCTIVE MATERIAL FROM BODY LUMENS

(71) Applicant: Inquis Medical, Inc., Redwood City, CA (US)

(72) Inventors: Vahid Saadat, Atherton, CA (US); William Jason Fox, San Mateo, CA (US); Richard Christian Ewers, Fullerton, CA (US); Mojgan Saadat, Atherton, CA (US); Sherwin Llamido, Redwood City, CA (US)

(73) Assignee: Inquis Medical, Inc., Atherton, CA (US)

( * ) Notice: Subject to any disclaimer, the term of this patent is extended or adjusted under 35 U.S.C. 154(b) by 0 days.

(21) Appl. No.: 17/393,618

(22) Filed: Aug. 4, 2021

Related U.S. Application Data

(60) Provisional application No. 63/192,562, filed on May 24, 2021, provisional application No. 63/184,083, (Continued)

(51) Int. Cl.
*A61B 17/221* (2006.01)
*A61B 17/22* (2006.01)

(52) U.S. Cl.
CPC .. *A61B 17/221* (2013.01); *A61B 2017/22051* (2013.01); *A61B 2017/22079* (2013.01)

(58) Field of Classification Search
CPC ........ A61B 17/00234; A61B 17/22032; A61B 17/221; A61B 2017/00323; A61B 2017/00526; A61B 2017/00778; A61B 2017/00867; A61B 2017/2212; A61B 2090/3966; A61B 6/12; A61M 25/0108

See application file for complete search history.

(56) References Cited

U.S. PATENT DOCUMENTS

| 5,569,275 A | 10/1996 | Kotula et al. |
| 5,954,737 A | 9/1999 | Lee |

(Continued)

FOREIGN PATENT DOCUMENTS

| DE | 212015000300 U1 | 8/2017 |
| EP | 1292244 B1 | 1/2007 |

(Continued)

*Primary Examiner* — Mohamed G Gabr
(74) *Attorney, Agent, or Firm* — Shay Glenn LLP

(57) ABSTRACT

According to some embodiments, the present technology includes a device for the disruption and/or removal of obstructive material in a blood vessel. The device can comprise an elongated shaft having a proximal portion, a distal portion, and a lumen extending therebetween. The device can further comprise a capture structure carried by the distal portion of the elongated shaft and having a greater cross-sectional dimension than a cross-sectional dimension of the elongated shaft. The capture structure can comprise an opening at a first end portion that is fluidly coupled to the lumen of the elongated shaft, a fluid impermeable sidewall enclosing an interior region, and an opening extending through a thickness of the sidewall. A portion of the sidewall surrounding the opening can be configured to deform towards or away from the interior region such that a cross-sectional dimension of the opening increases to receive the obstructive material therethrough.

30 Claims, 35 Drawing Sheets

Related U.S. Application Data filed on May 4, 2021, provisional application No. 63/176,224, filed on Apr. 17, 2021.

(56) References Cited

U.S. PATENT DOCUMENTS

| | | | |
|---|---|---|---|
| 7,655,016 | B2 | 2/2010 | Demarais et al. |
| 7,699,790 | B2 | 4/2010 | Simpson |
| 7,713,235 | B2 | 5/2010 | Torrance et al. |
| 7,927,346 | B2 | 4/2011 | Vancamp et al. |
| 8,252,020 | B2 | 8/2012 | Hauser et al. |
| 8,298,252 | B2 | 10/2012 | Krolik et al. |
| 8,430,837 | B2 | 4/2013 | Jenson et al. |
| 8,613,717 | B2 | 12/2013 | Aklog et al. |
| 8,956,386 | B2 | 2/2015 | Hauser et al. |
| 9,055,964 | B2 | 6/2015 | Cartier et al. |
| 9,402,938 | B2 | 8/2016 | Aklog et al. |
| 9,655,633 | B2 | 5/2017 | Leynov et al. |
| 9,808,266 | B2 | 11/2017 | Ray et al. |
| 9,848,975 | B2 | 12/2017 | Hauser |
| 10,016,266 | B2 | 7/2018 | Hauser |
| 10,226,268 | B2 | 3/2019 | Ulm |
| 10,285,720 | B2 | 5/2019 | Gilvarry et al. |
| 10,383,983 | B2 | 8/2019 | Aklog et al. |
| 10,517,617 | B2 | 12/2019 | Aklog et al. |
| 10,568,654 | B2 | 2/2020 | Cartier et al. |
| 10,661,053 | B2 | 5/2020 | Yang et al. |
| 10,695,159 | B2 | 6/2020 | Hauser |
| 10,716,586 | B2 | 7/2020 | Krolik et al. |
| 10,722,238 | B2 | 7/2020 | Sutton et al. |
| 10,743,907 | B2 | 8/2020 | Bruzzi et al. |
| 10,799,331 | B2 | 10/2020 | Hauser |
| 10,835,257 | B2 | 11/2020 | Ferrera et al. |
| 10,945,758 | B1 | 3/2021 | Davis et al. |
| 11,013,523 | B2 | 5/2021 | Arad Hadar |
| 2003/0191493 | A1 | 10/2003 | Epstein et al. |
| 2009/0069828 | A1* | 3/2009 | Martin ................. A61B 17/221 606/159 |
| 2010/0023033 | A1 | 1/2010 | Mauch et al. |
| 2011/0137399 | A1* | 6/2011 | Chomas ............ A61M 25/0075 623/1.12 |
| 2013/0317589 | A1* | 11/2013 | Martin ............... A61B 17/3207 623/1.2 |
| 2015/0005781 | A1* | 1/2015 | Lund-Clausen ..... A61B 17/221 606/127 |
| 2016/0089227 | A1 | 3/2016 | Loh |
| 2018/0206865 | A1* | 7/2018 | Martin ................. A61B 17/221 |
| 2018/0235644 | A1* | 8/2018 | Jaffe ............... A61B 17/22032 |
| 2019/0167287 | A1 | 6/2019 | Vale et al. |
| 2019/0175210 | A1 | 6/2019 | Wittens |
| 2019/0321525 | A1 | 10/2019 | Aklog et al. |
| 2020/0054432 | A1* | 2/2020 | Martin .................... A61F 2/014 |
| 2020/0121333 | A1 | 4/2020 | Aklog et al. |
| 2020/0129202 | A1 | 4/2020 | Schoenle et al. |
| 2020/0129741 | A1 | 4/2020 | Kawwas et al. |
| 2020/0164117 | A1 | 5/2020 | Culhane et al. |
| 2020/0170666 | A1 | 6/2020 | Trosper et al. |
| 2020/0187976 | A1 | 6/2020 | Cartier et al. |
| 2020/0246029 | A1 | 8/2020 | Singleton et al. |
| 2020/0281612 | A1 | 9/2020 | Kelly et al. |
| 2020/0305900 | A1 | 10/2020 | Vale et al. |
| 2021/0022766 | A1 | 1/2021 | Bruzzi et al. |
| 2021/0022843 | A1 | 1/2021 | Hauser |
| 2021/0161544 | A1 | 6/2021 | Casey |
| 2021/0161545 | A1 | 6/2021 | Bhogal et al. |

FOREIGN PATENT DOCUMENTS

| | | |
|---|---|---|
| EP | 2782514 B1 | 12/2016 |
| EP | 3215034 A1 | 9/2017 |
| EP | 3244813 A1 | 11/2017 |
| EP | 3311875 A1 | 4/2018 |
| EP | 2231256 B1 | 5/2018 |
| EP | 1617893 B1 | 6/2018 |
| EP | 2299916 B1 | 8/2018 |
| EP | 2309934 B1 | 11/2018 |
| EP | 3500191 B1 | 9/2020 |
| EP | 3705067 A2 | 9/2020 |
| EP | 3705067 A3 | 11/2020 |
| EP | 3787523 A1 | 3/2021 |
| EP | 2908901 B1 | 5/2021 |
| EP | 3831318 A1 | 6/2021 |
| WO | 2017154748 A1 | 9/2017 |
| WO | 2017161204 A1 | 9/2017 |
| WO | 2020160179 A1 | 8/2020 |
| WO | 2021016213 A1 | 1/2021 |

* cited by examiner

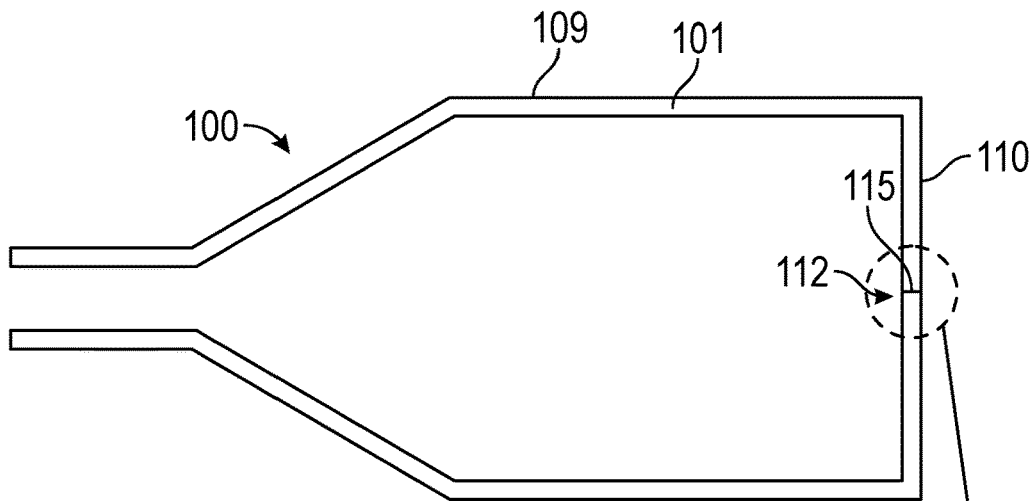
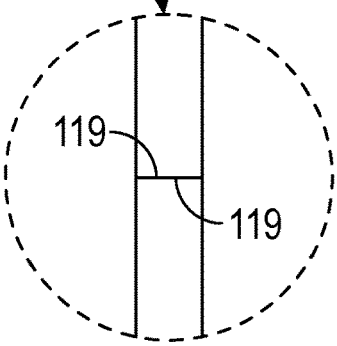
FIG. 6A
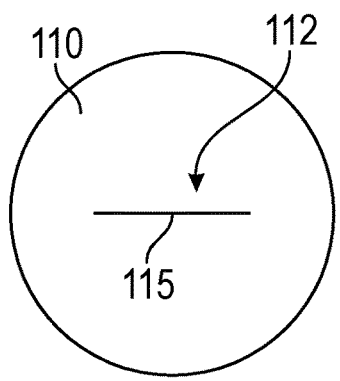
FIG. 6B
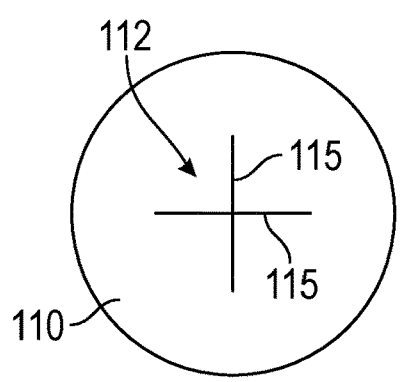
FIG. 6C
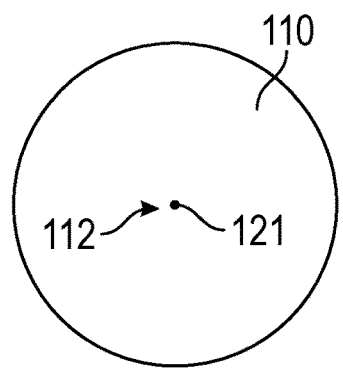
FIG. 6D

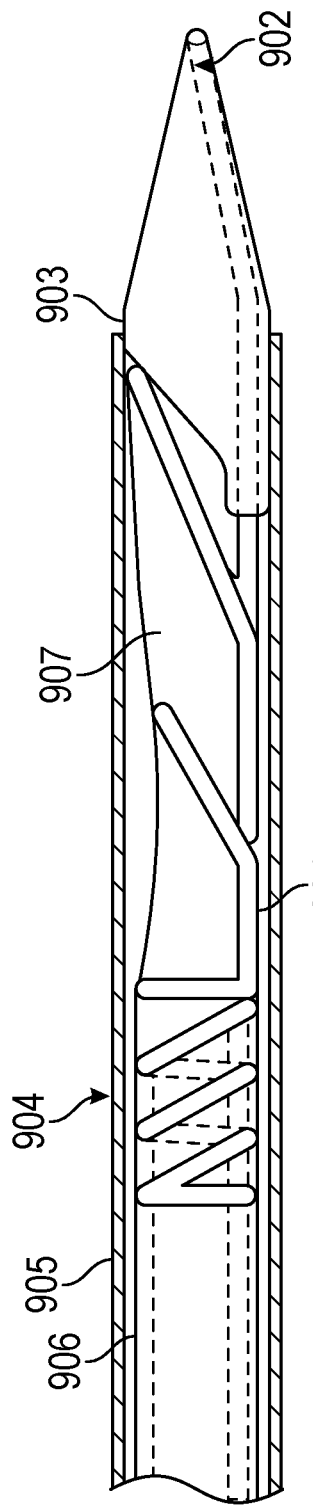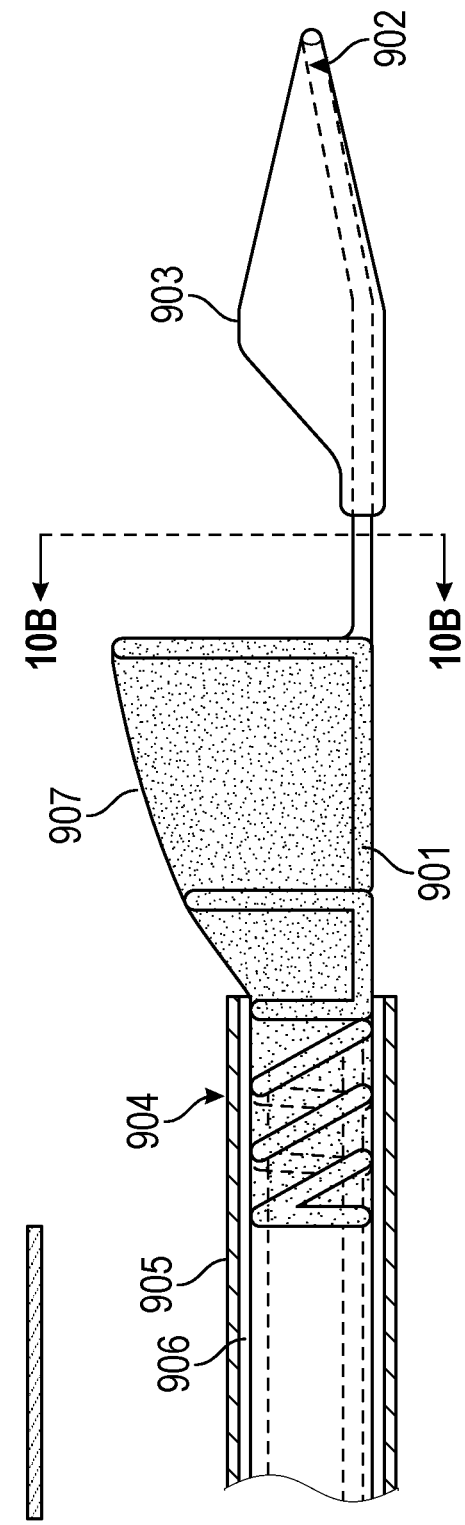

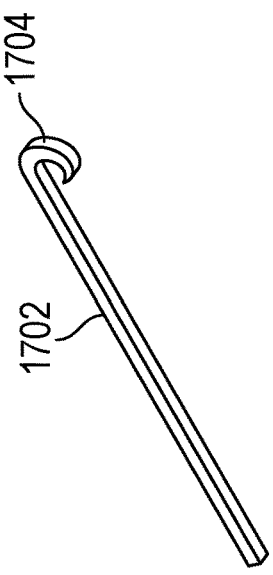
FIG. 17C
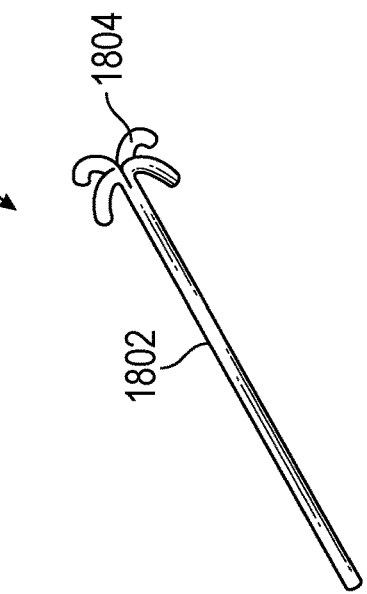
FIG. 18C
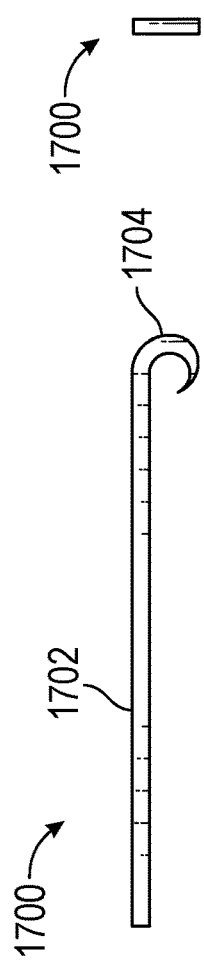
FIG. 17B
FIG. 17A
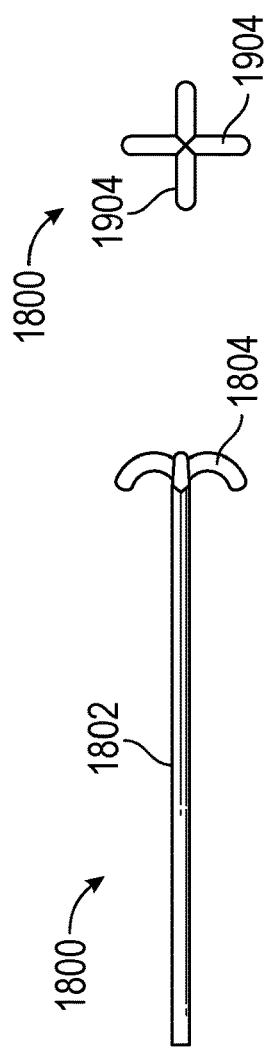
FIG. 18B
FIG. 18A

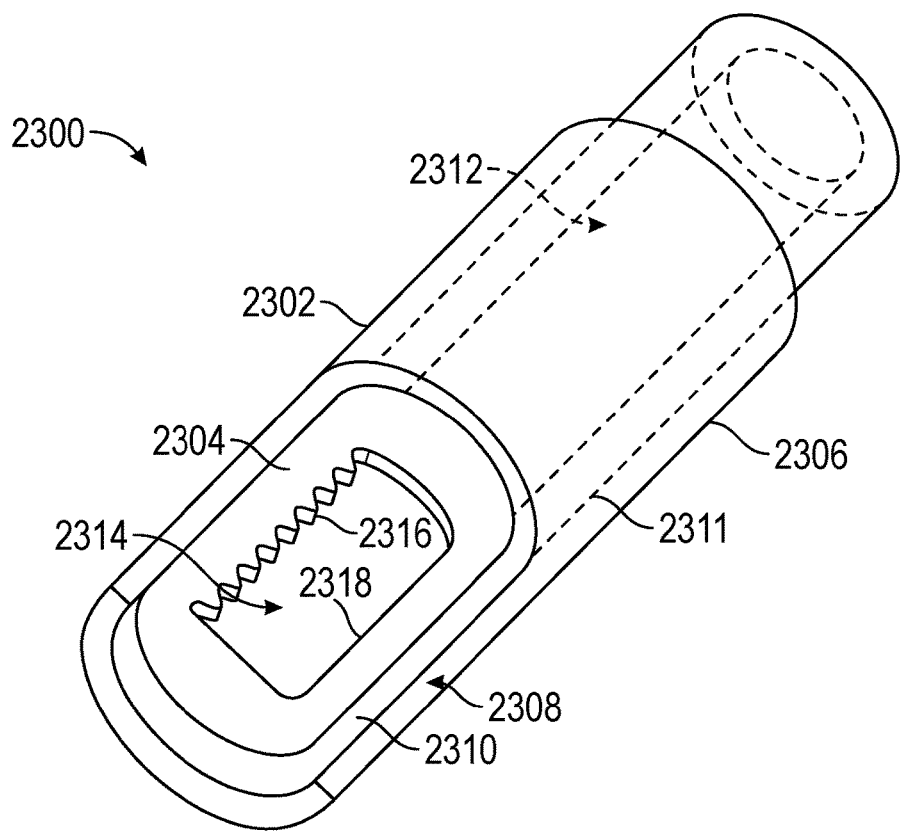
FIG. 23
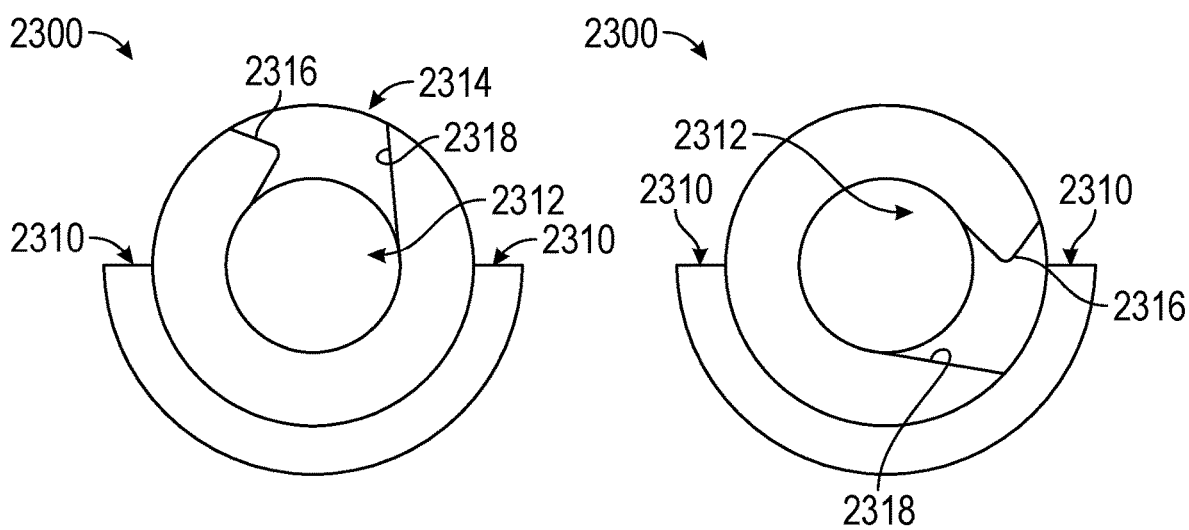
FIG. 24A          FIG. 24B

DEVICES, SYSTEMS, AND METHODS FOR REMOVING OBSTRUCTIVE MATERIAL FROM BODY LUMENS

CROSS-REFERENCE TO RELATED APPLICATION(S)

The present application incorporates by reference herein each of the following references in their entireties: U.S. Provisional Application No. 63/176,224, filed Apr. 17, 2021, U.S. Provisional Application No. 63/184,083, filed May 4, 2021, and U.S. Provisional Application No. 63/192,562, filed May 24, 2021.

TECHNICAL FIELD

The present technology relates to devices, systems, and methods for removing obstructive material from body lumens. In particular embodiments, the present technology relates to devices, systems, and methods for removing clot material from blood vessel lumens.

BACKGROUND

Venous thromboembolism (VTE) is the third leading vascular diagnosis after heart attack and stroke, affecting between 300,000 to 600,000 people in the US each year. There are two types of VTE which are Deep Vein Thrombosis (DVT) and Pulmonary Embolism (PE). DVT is a clot in a deep vein, usually in the leg. PE occurs when a deep vein thrombus breaks free from the vein, travels through the heart, into the lungs and then blocks some or all the blood supply to the lungs. Venous thrombosis is known to be associated with considerable short-term morbidity and mortality having a 20% mortality rate within a year of a venous thrombosis event and a two to four times higher mortality rate for patients with PE within three months after the event.

The recommended treatment for VTE according to the American Society of Hematology guidelines is the use of thrombolytic therapy and direct oral anticoagulants. Thrombolytic therapy includes intravenous or local delivery of tissue Plasminogen Activator (tPA) which is an enzyme designed to dissolve the blood clot that is blocking the blood flow. The thrombolytic therapy has been shown to be effective, but the treatment takes hours and involves the risk of hemorrhaging elsewhere in the body. In some cases, the thrombus is surgically removed from the vessel via an open surgical procedure. More recently, the thrombus or emboli is mechanically removed using a thrombectomy device via a percutaneous procedure with access through a distal or proximal vein. The current thrombectomy devices on the market use expandable cages, shape memory wires, and compliant balloons to physically grab and/or scrape off and extract the thrombus from the blood vessel. Several existing thrombectomy devices also aspirate the thrombus, with and without mechanically engaging and securing the clot. The use of aspiration for thrombus extraction has produced promising results. However, current PE thrombectomy devices require electrically powered suction systems or large profile catheters to generate sufficient aspiration power to aspirate the large pulmonary emboli in the pulmonary arteries. The use of such larger diameter aspiration catheters can cause safety concerns, such as access site complications, excessive blood loss, and damage to the vessel wall or the valves of the heart. These current technologies also require multiple passes and repositioning steps to completely remove the large pulmonary emboli. For DVT removal, mechanical scraping of thrombus from the vessel wall and removal with aspiration has been shown to increase blood flow within the vessel. However risk of damaging the vessel wall or valves remains high. Accordingly, there is a need for improved systems and methods for removing thrombus from the vascular anatomy as described herein.

SUMMARY

The present technology provides devices, systems, and methods for disrupting and/or removing obstructive material from a blood vessel. The subject technology is illustrated, for example, according to various aspects described below, including with reference to FIGS. 1-36. Various examples of aspects of the subject technology are described as numbered clauses (1, 2, 3, etc.) for convenience. These are provided as examples and do not limit the subject technology.

1. A device for the disruption and/or removal of obstructive material in a blood vessel, the device comprising:
   an elongated shaft having a proximal portion, a distal portion, and a lumen extending therebetween, wherein the distal portion of the elongated shaft is configured to be positioned at a treatment site within the blood vessel proximate the obstructive material; and
   a capture structure carried by the distal portion of the elongated shaft and having a greater cross-sectional dimension than a cross-sectional dimension of the elongated shaft, the capture structure comprising (a) a first end portion, a second end portion, and a longitudinal axis extending therebetween, (b) an opening at the first end portion that is fluidly coupled to the lumen of the elongated shaft, (c) a fluid impermeable wall enclosing an interior region, and (d) an opening extending through a thickness of the wall, and
   wherein a portion of the wall surrounding the opening is configured to deform towards or away from the interior region, thereby increasing a cross-sectional dimension of the opening.

2. The device of Clause 1, wherein a proximal portion of the elongated shaft is configured to be fluidly coupled to a negative pressure source to apply a negative pressure within the capture structure.

3. The device of Clause 2, wherein the portion of the wall is configured to deform in response to the application of negative pressure.

4. The device of Clause 1, further comprising a disruptor configured to be positioned within the interior region of the capture structure, wherein the disruptor is configured to break up obstructive material received through the opening in the wall.

5. The device of any one of Clauses 1 to 4, wherein the wall has (a) a first region extending longitudinally between the opening and the second end portion, and (b) a second region extending radially inwardly from the first region.

6. The device of any one of Clauses 1 to 5, wherein the opening is a slit.

7. The device of any one of Clauses 1 to 6, wherein the capture structure is configured to transform between (a) a collapsed state in which the capture structure has a first cross-sectional dimension, and (b) an expanded state in which the capture structure has a second cross-sectional dimension greater than the first cross-sectional dimension.

8. A device for the disruption and/or removal of obstructive material in a blood vessel, the device comprising:
   an elongated shaft having a proximal portion, a distal portion, and a lumen extending therebetween, the lumen having a cross-sectional dimension, wherein the distal portion of the elongated shaft is configured to be positioned at a treatment site within the blood vessel proximate the obstructive material;

a capture structure carried by the distal portion of the elongated shaft and defining an interior cavity in fluid communication with the lumen of the elongated shaft, the interior cavity having a cross-sectional dimension and configured to receive the obstructive material therein, wherein a cross-sectional dimension of the interior cavity is greater than the cross-sectional dimension of the lumen; and an engagement wall extending radially inwardly from a distal end of the capture structure and having an opening therethrough that is in fluid communication with the cavity, wherein the opening has a cross-sectional dimension less than the cross-sectional dimension of the interior cavity of the capture structure.

9. The device of Clause 8, wherein the opening in the engagement wall has a cross-sectional dimension greater than the cross-sectional dimension of the lumen of the elongated shaft.

10. The device of Clause 8, wherein the opening in the engagement wall has a cross-sectional dimension less than the cross-sectional dimension of the lumen of the elongated shaft.

11. A device for the disruption and/or removal of obstructive material in a blood vessel, the device comprising:

an elongated shaft having a proximal portion, a distal portion, and a lumen extending therebetween, wherein the distal portion of the elongated shaft is configured to be positioned at a treatment site within the blood vessel proximate the obstructive material;

a capture structure carried by the distal portion of the elongated shaft and defining an interior cavity in fluid communication with the lumen of the elongated shaft, the interior cavity having a cross-sectional dimension and configured to receive the obstructive material therein; and an engagement wall extending radially inwardly from a distal end of the capture structure and having an opening therethrough, the opening in fluid communication with the cavity, wherein the opening has a cross-sectional dimension less than the cross-sectional dimension of the interior cavity of the capture structure, wherein the engagement wall is configured to deform in response to engagement with the obstructive material to increase the cross-sectional dimension of the opening.

12. A device for the disruption and/or removal of obstructive material in a blood vessel, the device comprising:

an elongated shaft having a proximal portion, a distal portion, and a lumen extending therebetween, wherein the distal portion of the elongated shaft is configured to be positioned at a treatment site within the blood vessel proximate the obstructive material;

a capture structure carried by the distal portion of the elongated shaft and defining an interior cavity in fluid communication with the lumen of the elongated shaft, the interior cavity having a cross-sectional dimension and configured to receive the obstructive material therein; and an engagement wall extending radially inwardly from a distal end of the capture structure and having an opening therethrough that is in fluid communication with the cavity, wherein the opening has a cross-sectional dimension less than the cross-sectional dimension of the interior cavity of the capture structure, wherein, when the engagement wall is pushed up against the obstructive material so that the obstructive material is in contact with an edge of the engagement wall surrounding the opening, the engagement wall deforms around the obstructive material such that the opening is stretched to an increased cross-sectional dimension.

13. The device of Clause 11 or Clause 12, wherein the portion of the engagement wall defining the opening is configured to apply a radially compressive force on obstructive material positioned within the opening.

14. The device of Clause 13, wherein the edge of the engagement wall surrounding the opening is configured to apply a radially compressive force on obstructive material positioned within the opening.

15. The device of any one of Clauses 11 to 14, wherein the proximal portion of the elongated shaft is configured to be coupled to a negative pressure source to apply a negative pressure in the interior cavity.

16. The device of any one of Clauses 11 to 15, wherein the capture structure comprises a sidewall that is substantially impermeable to fluids.

17. The device of any one of Clauses 11 to 16, wherein the portion of the engagement wall surrounding the opening is substantially impermeable to fluids.

18. The device of any one of Clauses 11 to 17, wherein the cross-sectional dimension of the interior cavity of the capture structure increases or remains substantially constant in a direction towards the distal end of the capture structure.

19. The device of any one of Clauses 11 to 18, wherein a maximum cross-sectional dimension of the interior cavity of the capture structure is at least two times greater than the cross-sectional dimension of the lumen of the elongated shaft.

20. The device of any one of Clauses 11 to 19, wherein the elongated shaft has an outer diameter of about 30 French or less, about 24 French of less, about 20 French or less, about 18 French of less, or about 16 French or less.

21. The device of any one of Clauses 11 to 20, wherein the interior cavity of the capture structure is configured to receive a disruptor, and wherein the disruptor is configured to mechanically engage and break up obstructive material received at least partially within the interior cavity.

22. A device for the disruption and/or removal of obstructive material in a blood vessel, the device comprising:

an elongated shaft having a proximal portion, a distal portion, and a lumen extending therebetween, wherein the distal portion of the elongated shaft is configured to be positioned at a treatment site within the blood vessel proximate the obstructive material; and a distal housing carried by the distal portion of the elongated shaft, the distal housing comprising (a) a sidewall extending between a first end portion fluidly coupled to the lumen of the elongated shaft and a second end portion, and (b) a distal wall extending across the second end portion and including an opening configured to receive the obstructive material therethrough, wherein the sidewall and the distal wall together enclose an interior region, and wherein the distal surface is configured such that advancement of the distal wall onto and/or over the obstructive material increases a cross-sectional dimension of the opening.

23. The device of Clause 22, wherein the opening of the distal surface has a cross-sectional dimension greater than the cross-sectional dimension of the lumen of the elongated shaft.

24. The device of Clause 22 or Clause 23, wherein a cross-sectional dimension of the opening is greater than a cross-sectional dimension of the lumen of the elongated shaft.

25. The device of any one of Clauses 22 to 24, wherein a cross-sectional dimension of the sidewall at the first end portion is less than a cross-sectional dimension of the sidewall at the second end portion.

26. The device of any one of Clauses 22 to 25, wherein a cross-sectional dimension of the interior region of the sidewall at the first end portion is less than a cross-sectional dimension of the interior region at the second end portion.

27. The device of any one of Clauses 22 to 26, wherein the portion of the distal wall defining the opening is configured to apply a radially compressive force on obstructive material positioned within the opening.

28. The device of any one of Clauses 22 to 27, wherein the proximal portion of the elongated shaft is configured to be fluidly coupled to a negative pressure source to apply a negative pressure in the interior region of the distal housing.

29. The device of any one of Clauses 22 to 28, wherein the sidewall is substantially impermeable to fluids.

30. The device of any one of Clauses 22 to 29, wherein the portion of the distal wall surrounding the opening is substantially impermeable to fluids.

31. The device of any one of Clauses 22 to 30, wherein the elongated shaft has an outer diameter of about 30 French or less, about 24 French of less, about 20 French or less, about 18 French of less, or about 16 French or less.

32. The device of any one of Clauses 22 to 31, wherein the interior region of the distal wall is configured to receive a disruptor, and wherein the disruptor is configured to mechanically engage and break up obstructive material received at least partially within the interior region.

33. A method for treating a blood vessel of a human patient, the method comprising:
   positioning a distal portion of a treatment device in the blood vessel at a treatment site proximate obstructive material, the treatment device comprising an elongated shaft and a capture structure disposed at a distal portion of the elongated shaft and enclosing an interior region, wherein a surface of the capture structure has an opening therethrough with a cross-sectional dimension less than a cross-sectional dimension of the interior region of the capture structure;
   engaging the obstructive material with the surface of the capture structure such that at least a portion of the obstructive material is positioned in and/or through the opening, thereby increasing a cross-sectional dimension of the opening; and
   removing at least the portion of the obstructive material from the patient's body.

34. The method of Clause 33, wherein engaging the obstructive material causes the surface to deform around the obstructive material, thereby stretching the opening.

35. The method of Clause 33, wherein engaging the obstructive material comprises creating a seal between the obstructive material and an edge of the surface surrounding the opening.

36. The method of Clause 33, wherein engaging the obstructive material comprises pushing the surface onto and/or over a portion of the obstructive material.

37. The method of Clause 33, further comprising applying negative pressure to the interior region of the capture structure before, during, and/or after engaging the obstructive material, thereby pulling the obstructive material through the surface opening and into the interior region.

38. The method of Clause 37, further comprising increasing a proximally-directed force on the obstructive material without increasing the negative pressure.

39. The method of Clause 33, further comprising positioning a disrupting element within the interior region of the capture structure before, during, and/or after engaging the obstructive material.

40. The method of Clause 39, further comprising breaking up the portion of the obstructive material positioned within the interior region with the disrupting element.

41. The method of Clause 39 or Clause 40, further comprising mechanically engaging the obstructive material with the disrupting element and pulling the obstructive material into the interior region of the capture structure with the disrupting element.

42. The method of any one of Clauses 33 to 41, further comprising removing the disrupting element from the patient's body while holding the capture structure at the treatment site.

43. The method of Clause 33, further comprising:
   applying negative pressure to the interior region of the capture structure before, during, and/or after engaging the obstructive material, and
   breaking up the portion of the obstructive material positioned within the interior region with a disrupting element positioned within the interior region,
   wherein applying the negative pressure and breaking up the obstructive material occur at different times.

44. The method of Clause 33, further comprising:
   applying negative pressure to the interior region of the capture structure before, during, and/or after engaging the obstructive material, and
   breaking up the portion of the obstructive material positioned within the interior region with a disrupting element positioned within the interior region,
   wherein at least some of the application of negative pressure occurs while the disrupting element is breaking up the obstructive material, or vice versa.

45. A device for the disruption and/or removal of obstructive material in a blood vessel, the device comprising:
   an elongated shaft having a proximal portion, a distal portion, and a lumen extending therebetween, wherein the distal portion of the elongated shaft is configured to be positioned at a treatment site within the blood vessel proximate the obstructive material; and
   a distal housing carried by the distal portion of the elongated shaft and having a greater cross-sectional dimension than a cross-sectional dimension of the elongated shaft, the distal housing comprising (a) a sidewall extending between an opening at a first end portion and a second end portion, the opening fluidly coupled to the lumen of the elongated shaft, (b) an engagement wall extending across the second end portion of the sidewall, and (c) an aperture extending through the sidewall and/or engagement wall, the aperture configured to receive the obstructive material therethrough, wherein the sidewall and the engagement wall together enclose an interior region, and
   wherein the engagement wall is configured to deform towards or away from the interior region such that a cross-sectional dimension of the opening increases.

46. A method of removing material from the vascular anatomy, the method comprising:
   advancing a distal section of a catheter with central lumen adjacent to unwanted material within vascular anatomy in a first radial profile;

expanding the distal section of a catheter with a central lumen to a second radial profile greater than the first radial profile;

engaging material with distal end of distal section of catheter;

applying negative pressure within central lumen of catheter onto the material causing at least a portion of material to enter distal section of catheter;

agitating material within the distal section of catheter while maintaining negative pressure within catheter;

aspirating at least a portion of the material from the vascular anatomy where the portion has a greater cross-sectional area than the cross-sectional area of the central lumen.

47. An extraction system, comprising;

an elongated catheter, having a proximal end, a proximal section, an expandable articulating distal section, an expandable distal orifice, a central lumen, and an agitating element within the central lumen, wherein the distal section first radial profile cross sectional area is less than or equal to proximal section profile cross-sectional area and the second radial profile cross-sectional area is greater than the proximal section profile area and has an axial length greater than 5 mm and a taper transition to the proximal section profile, and wherein the cross-sectional area of the distal section in the second radial profile maintains an area greater than the proximal section profile when negative pressure is applied within the central lumen.

48. A method for treating a blood vessel of a human patient, the method comprising:

positioning a distal portion of a treatment device in the blood vessel at a treatment site proximate obstructive material, the treatment device comprising an elongate shaft and a capture structure disposed at a distal portion of the elongate shaft and enclosing an interior region;

positioning the obstructive material within the interior region of the capture structure;

macerating the obstructive material within the interior region of the capture structure with a disrupting element positioned within the interior region of the capture structure; and applying aspiration to pull the processed portion of the obstructive material from the patient's body.

49. The method of Clause 48, wherein macerating the obstructive material occurs without aspiration.

50. A method for treating a blood vessel of a human patient, the method comprising:

positioning a distal portion of a treatment device in the blood vessel at a treatment site proximate obstructive material, the treatment device comprising an elongated shaft and a capture structure disposed at a distal portion of the elongated shaft and enclosing an interior region, wherein a surface of the capture structure has an opening therethrough with a cross-sectional dimension less than a cross-sectional dimension of the interior region of the capture structure;

engaging the obstructive material with the surface of the capture structure such that at least a portion of the obstructive material is positioned in and/or through the opening, thereby increasing a cross-sectional dimension of the opening; and removing at least the portion of the obstructive material from the patient's body.

51. The method of Clause 50, wherein engaging the obstructive material causes the surface to deform around the obstructive material, thereby stretching the opening.

52. The method of Clause 50 or Clause 51, wherein engaging the obstructive material comprises creating a seal between the obstructive material and an edge of the surface surrounding the opening.

53. The method of any one of Clauses 50 to 52, wherein engaging the obstructive material comprises pushing the surface onto and/over a portion of the obstructive material.

54. The method of any one of clauses Clause 50 to 53, further comprising applying negative pressure to the interior region of the capture structure before, during, and/or after engaging the obstructive material, thereby pulling the obstructive material through the surface opening and into the interior region.

BRIEF DESCRIPTION OF THE DRAWINGS

[0061] Many aspects of the present disclosure can be better understood with reference to the following drawings. The components in the drawings are not necessarily to scale. Instead, emphasis is placed on illustrating clearly the principles of the present disclosure.

In FIG. 2E, the cover has been removed from the capture structure to better view the frame.

FIG. 6A is a partially schematic cross-sectional side view of a capture structure configured in accordance with the present technology.

FIGS. 6B-6D show different slit configurations for use with the capture structures of the present technology.

FIGS. 9 and 10A show a distal portion of a treatment system in a collapsed state and an expanded state, respectively, in accordance with several embodiments of the present technology.

FIGS. 17A-17C are various views of a disrupting element configured in accordance with several embodiments of the present technology.

FIGS. 18A-18C are various views of a disrupting element configured in accordance with several embodiments of the present technology.

FIGS. 23, 24A, 24B, and 25 are various views of a disrupting device configured in accordance with several embodiments of the present technology.

DETAILED DESCRIPTION

I. Overview

Figure 1:
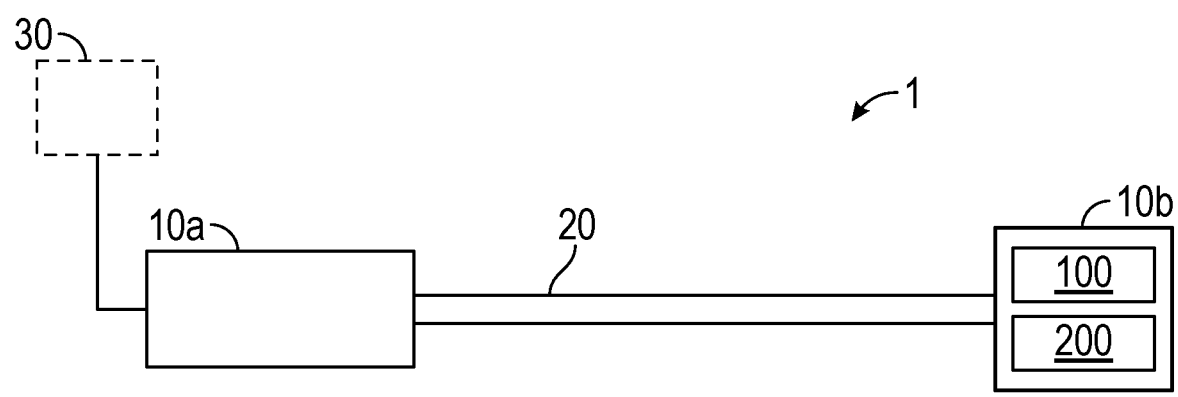
FIG. 1 schematically depicts a treatment system configured in accordance with several embodiments of the present technology.

FIG. 1 schematically depicts a treatment system 1 (also referred to herein as "the system 1") configured in accordance with the present technology. The treatment system 1 is configured to access a blood vessel (such as a vein or an artery) and disrupt, capture, and/or remove obstructive material from the blood vessel lumen. As used herein, "obstruction" or "obstructive material" can comprise, for example, clot material, atherosclerotic plaque, and/or other flow-obstructing structures, including those derivative of clot material, such as fibrotic clot material. Moreover, as used herein, the act of "disrupting" obstructive material includes breaking the material into smaller pieces, modifying the shape of the material, stretching and/or elongating the material, compressing the material, permanently or temporarily repositioning all or a portion of the material, extracting all or a portion of the material, macerating the material, morcellating the material, and/or any other action that modifies the obstructive material.

As shown in FIG. 1, the system 1 may comprise a proximal portion 10a configured to be positioned outside of the patient's body during the procedure, a distal portion 10b configured to be positioned at a treatment site within a blood vessel, and one or more elongated shafts 20 extending between the proximal portion 10a and the distal portion 10b. The proximal portion 10b can comprise one or more handles, actuators, and/or connectors that are coupled to a proximal end region of the elongated shaft(s) 20 to facilitate delivery and/or removal of fluids and other material from the treatment site, as well as to provide a means for manipulating the distal portion 10b of the system 1. In some embodiments, the system 1 further comprises a negative pressure source 30 configured to be fluidly coupled to the distal portion 10b via the one or more handles and the elongated shaft(s) 20.

The distal portion 10b of the system 1 can include a capture structure 100 and a disrupting element 200 that work synergistically to engage and process obstructive material at the treatment site to enable removal of the obstructive material through the elongated shaft(s) 20. The capture structure 100 can be any of the capture structures disclosed herein, and the disrupting element 200 can be any of the disrupting elements and/or disruptors disclosed herein. In some embodiments of the treatment system 1, the distal portion 10b includes only the capture structure 100 and does not include a disrupting element 200.

The capture structure 100 can be carried by a distal end region of the elongated shaft(s) 20 and is configured to engage and capture obstructive material at the treatment site. In some embodiments the capture structure 100 is integral with the elongated shaft(s) 20, and in some embodiments the capture structure 100 is a separate component that is coupled to a distal end region of the elongated shaft(s) 20. The capture structure 100 can be configured to transform between a collapsed or low-profile state for navigation through the vasculature and an expanded state for engaging the obstructive material. In some embodiments, the capture structure 100 has an outer cross-sectional dimension in the collapsed state that is substantially the same as or less than that of the elongated shaft(s) 20, and an outer cross-sectional dimension in the expanded state that is greater than that of the elongated shaft(s) 20. The elongated shaft(s) 20 and/or collapsed capture structure 100 can have an outer cross-sectional dimension of 24 Fr or less, 20 Fr or less, or 16 Fr or less, and the expanded capture structure 100 can have an outer cross-sectional dimension of greater than 24 Fr, including 28 Fr or greater, 36 Fr or greater, 40 Fr or greater, or 45 Fr or greater. The versatile profile of the capture structure 100 confers the delivery advantages associated with a smaller profile catheter, such as improved trackability and reduced risk of damaging a vessel wall or heart structure, as well as the therapeutic benefits of a larger diameter capture structure, such as the ability to engage, hold on to, and remove large volumes of obstructive material efficiently. Efficient material removal reduces the number of passes required to remove all of the obstructive material from the treatment site, which reduces the amount of blood loss and procedure time.

In the expanded state, the capture structure 100 may comprise a fluid impermeable housing that provides a substantially enclosed working space that is configured to receive obstructive material for further processing and extraction from the body. The capture structure 100 can include a small orifice in the housing that is configured to engage and receive the obstructive material. The portion of the capture structure 100 defining the orifice can comprise a material configured to deform in response to negative pressure and/or engagement with the obstructive material, thereby enlarging the orifice. According to several embodiments, if no obstructive material is positioned against the orifice when aspiration is applied, the orifice may deform slightly but the change will be relatively small (i.e., less than 20% of the orifice's original cross-sectional dimension, less than the cross-sectional dimension of the interior region of the capture structure 100, etc.) until the obstructive material is engaged. Limiting the size of the orifice in this way advantageously reduces blood loss during aspiration.

The interior region of the capture structure 100 can be fluidly coupled to the negative pressure source 30 via the elongated shaft 24, and negative pressure can be applied to the capture structure 100 to draw obstructive material through the orifice and continue pulling the material proximally through the elongated shaft(s) 20 to a location outside of the patient's body. Instead of or in addition to applying aspiration to engage the obstructive material and/or pull the obstructive material into the capture structure 100, the operator can advance the capture structure 100 onto and over the obstructive material to force the obstructive material through the orifice. Engagement of the obstructive material in this manner deforms the wall surrounding the opening, thereby enlarging the opening to receive larger volumes of obstructive material and increasing the aspiration force applied at the orifice.

Once all or a portion of the obstructive material is disposed within the capture structure 100, the disrupting element 200 can be activated (if necessary) to disrupt the obstructive material so that the obstructive material is in a form conducive to aspiration through the elongated shaft(s) 20. In some embodiments, the disrupting element 200 disrupts the obstructive material as it enters the interior region of the capture structure 100 and/or a lumen of the elongated shaft(s) 20.

II. Selected System Embodiments

Figure 2A:
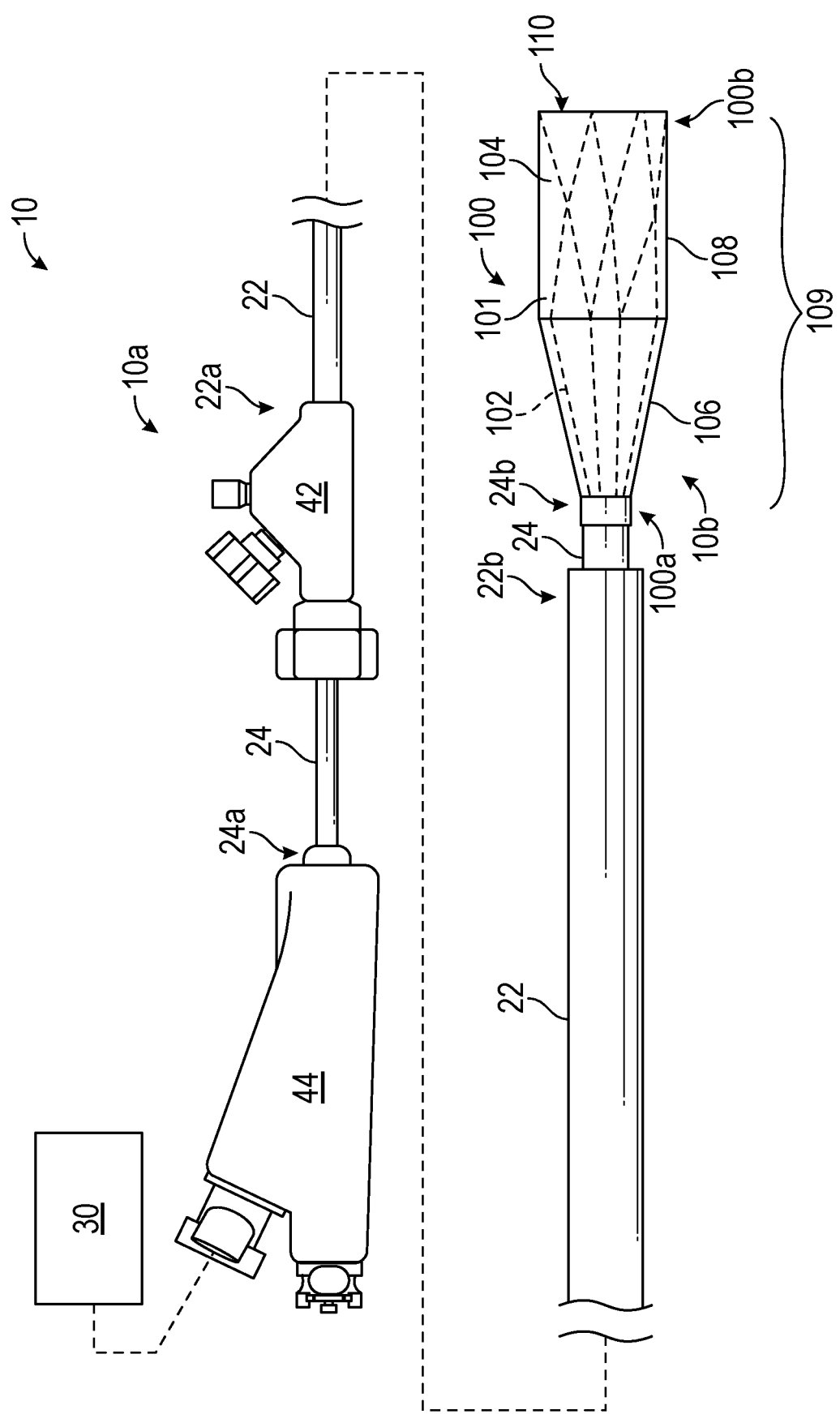
FIG. 2A shows a treatment system configured in accordance with several embodiments of the present technology.

FIG. 2A shows a treatment system 10 configured in accordance with several embodiments of the present technology. The treatment system 10 includes a proximal portion 10a configured to be extracorporeally positioned during a procedure and a distal portion 10b configured to be intravascularly delivered to a treatment site within a blood vessel. The distal portion 10b can comprise a capture structure 100 configured to engage, capture, and/or process obstructive material to facilitate removal of the obstructive material from the patient's body. The capture structure 100 can have a collapsed or low-profile state for delivery through the vasculature to the treatment site, and an expanded state (shown in FIG. 2A) for engaging with the obstructive material.

As shown in FIG. 2A, the treatment system 10 can include a sheath 22 and an elongated shaft 24 extending between the proximal and distal portions 10a, 10b of the system 10. The sheath 22 can be a generally tubular member having a proximal end portion 22a, a distal end portion 22b, and a lumen extending therethrough. The elongated shaft 24 can also be a generally tubular member having a proximal end portion 24a, a distal end portion 24b, and a lumen extending therethrough. The elongated shaft 24 can be configured to be slidably positioned through the lumen of the sheath 22. In some embodiments, the capture structure 100 is carried by a distal end portion 24b of the elongated shaft 24, and both the elongated shaft 24 and the capture structure 100 are configured to be slidably disposed within the sheath's lumen. In those embodiments where the capture structure 100 is self-expanding, the sheath 22 can be configured to radially constrain the capture structure 100 during delivery of the distal portion 10b and release the capture structure 100 to self-expand into the expanded state upon proximal withdrawal of the sheath 22.

The proximal portion 10a of the system 10 can include a first hub 42 and a second hub 44 configured to be positioned external to the patient. A distal region of the first hub 42 can be secured to the proximal end portion 22a of the sheath 22, and a proximal region of the first hub 42 can include an opening configured to slidably receive the elongated shaft 24 therethrough. A distal region of the second hub 44 can be secured to the proximal end portion 24a of the elongated shaft 24, and a proximal region of the second hub 44 can include an opening configured to receive a guidewire and/or another interventional device therethrough (such as a disrupting element, as discussed in greater detail herein). In some embodiments, the system 10 can include a manipulation member (not shown) having a first end coupled to an actuator at a hub (such as first hub 42 and/or second hub 44) and a second end coupled to a distal portion of the corresponding elongated shaft 24 and/or sheath 22. The manipulation member is configured to bend, flex, and/or otherwise articulate a distal portion of the corresponding elongated shaft 24 and/or sheath 22 when actuated by the operator.

The first and/or second hubs 42, 44 can include a hemostatic adaptor, a Tuohy Borst adaptor, and/or other suitable connectors, valves and/or sealing devices. For example, in some embodiments, the second hub 44 includes a connector configured to be coupled to a negative pressure source 30 (shown schematically), such as a syringe or a vacuum pump, for applying a negative pressure through a lumen of the elongated shaft 24. Additionally or alternatively, the first hub 42 can include a connector configured to be coupled to a negative pressure source 30 for applying a negative pressure through a lumen of the sheath 22. In some embodiments, the first and/or second hub 42, 44 can include a port configured to be coupled to a fluid source for delivering one or more fluids to the treatment site before, during and/or after the procedure (e.g., contrast, saline, etc.). Additionally or alternatively, the first and/or second hubs 42, 44 can include one or more ports configured to be coupled to a collection chamber for receiving and containing aspirated material from the treatment site. In some embodiments, the first and/or second hub 42, 44 includes one or more actuators that enable the operator to manipulate the distal portion 10b of the system 10. For example, the second hub 44 can include an actuator for controlling the curvature of an articulating region of the elongated shaft 24, as discussed in greater detail herein.

Figure 2B:
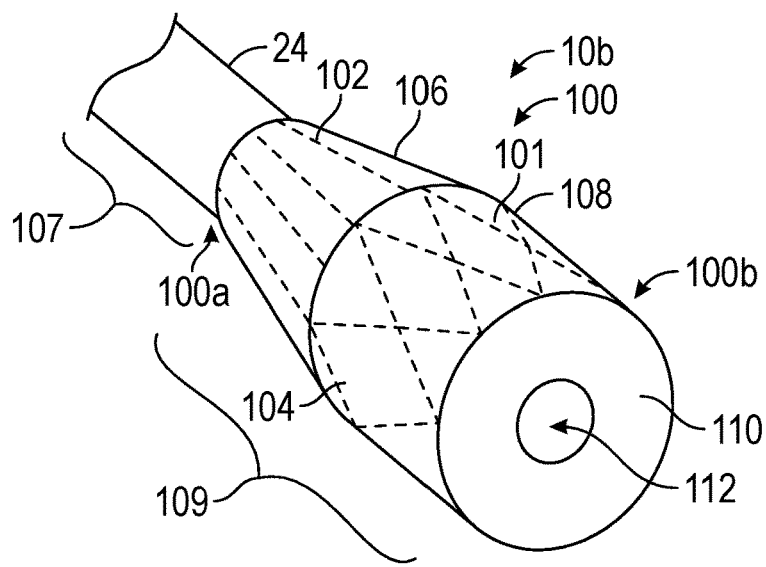
FIG. 2B is an isometric view of a distal portion of the treatment system shown in FIG. 2A.

At least in the expanded state, the capture structure 100 can enclose an interior region 114 (see FIG. 2C) that is configured to receive and process obstructive material from the treatment site to facilitate removal of the obstructive material from the patient's body. As shown in FIGS. 2A and 2B, the capture structure 100 can have a proximal end portion 100a, a distal end portion 100b, and a longitudinal axis L (FIG. 2C) extending therebetween. The proximal end portion 100a of the capture structure 100 defines a proximal opening 103 (see FIG. 2C) and is coupled to the distal end portion 24b of the elongated shaft 24. As such, the interior region 114 of the capture structure 100 is fluidly coupled to the lumen of the elongated shaft 24 such that negative pressure applied to the lumen of the elongated shaft 24 is also applied to the interior region 114 of the capture structure 100. The lumen of the elongated shaft 24 and the interior region 114 of the capture structure 100 can be referred to together as "the aspiration lumen."

The wall of the capture structure 100 can comprise a tubular sidewall 109 extending longitudinally between the first and second end portions 100a, 100b and an engagement wall and/or surface 110 extending across a distal end of the sidewall 109. The tubular sidewall 109 can extend between a proximal opening and a distal opening, and can comprise a tapered portion 106 and a substantially cylindrical portion 108. In some embodiments, the sidewall 109 and/or capture structure 100 comprises a neck portion 107 at the proximal end of the tapered portion 106 that is configured to be coupled to the distal end portion 24b of the elongated shaft 24. The neck portion 107 can have a cross-sectional dimension less than a cross-sectional dimension of the main body of the capture structure 100. All or a portion of the neck portion 107 can be positioned over or within the distal end portion 24b of the elongated shaft 24, or the capture structure 100 and/or neck portion 107 can be joined end-to-end. In some embodiments, the capture structure and/or sidewall 109 do not include a neck portion 107 and the proximal end of the tapered portion 106 is coupled to the distal end portion 24b of the elongated shaft 24.

The engagement wall 110 can extend across and cover a portion of the sidewall 109. In the example shown in FIGS. 2A-2C, the sidewall 109 has an annular distal surface and the engagement wall 110 extends across that surface, thereby forming a distal face of the capture structure 100. In those embodiments where the opening 112 and/or engagement wall 110 are disposed at another portion of the capture structure 100 (as detailed below), such as along the substantially cylindrical portion 108 or tapered portion 106, the engagement wall 110 does not comprise the distal face of the capture structure 100. The engagement wall 110 includes an outer engagement surface 111 configured to contact obstructive material at the treatment site and an opening 112 configured to receive obstructive material therethrough. In some embodiments, the engagement wall 110 coincides with and/or comprises the distal-most portion of the capture structure 100, at least when the capture structure 100 is in a resting state.

Figure 5A:
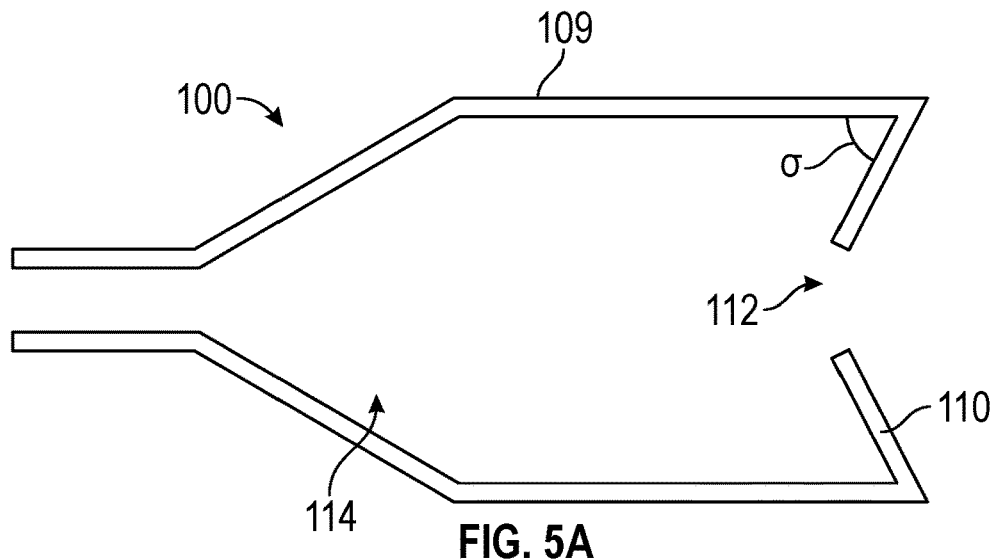
FIGS. 5A-5I depict different capture structure configurations in accordance with the present technology.
Figure 5B:
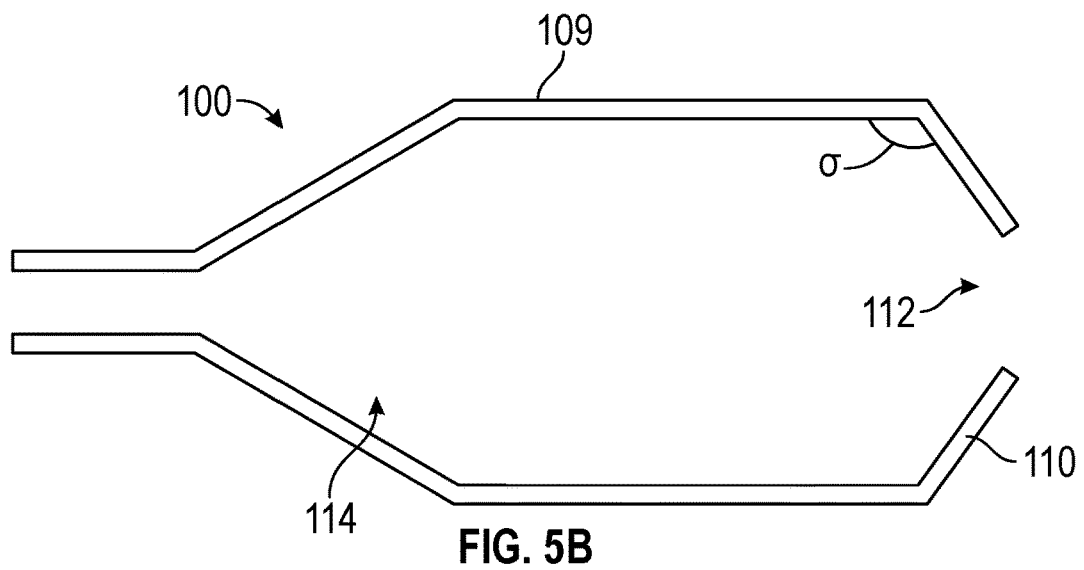
Figure 5C:
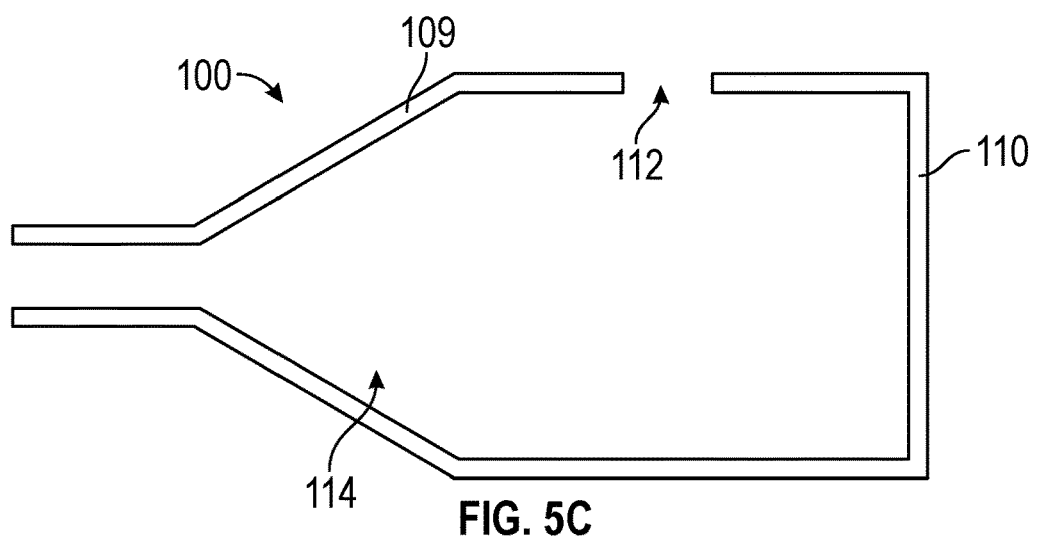
Figure 5D:
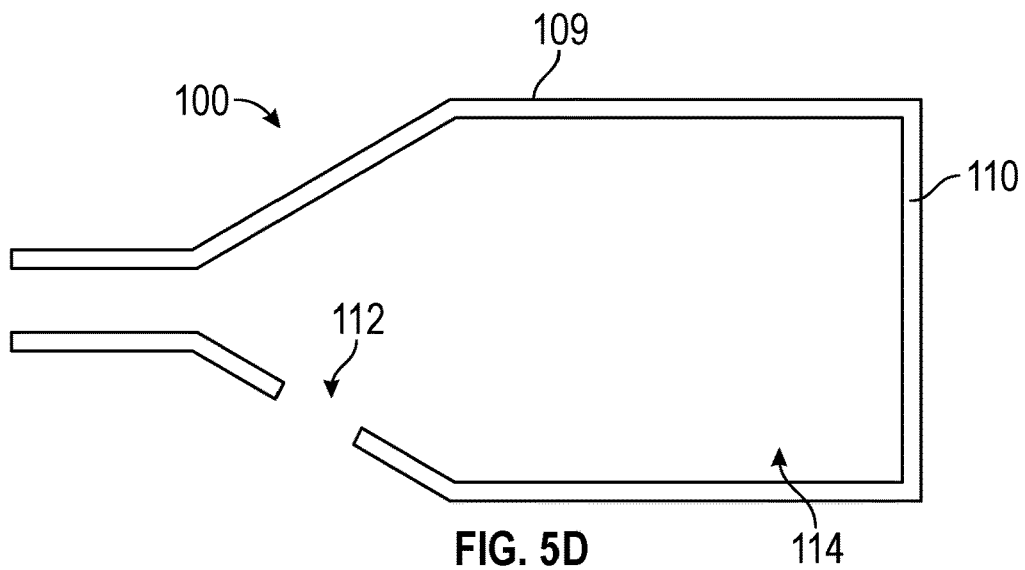
Figure 5E:
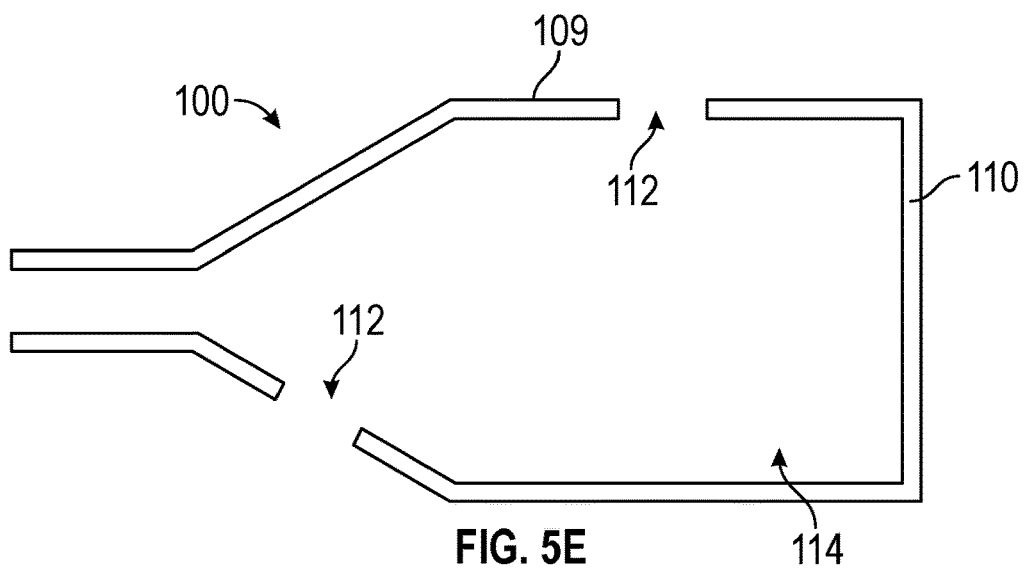

According to several aspects of the present technology, all or a portion of the engagement wall 110 and/or opening 112 is disposed proximal of the distal-most portion of the capture structure 100. For example, the engagement wall 110 and/or opening 112 can be disposed at and/or along the sidewall 109 (for example, as shown in FIGS. 5C and 5D). In such embodiments, the distal face of the capture structure 100 can be closed (e.g., does not include an opening 112). A laterally-positioned engagement wall 110 and/or opening 112 can be beneficial for engaging obstructive material positioned laterally of the capture structure 100 within the blood vessel. In these and other embodiments, the engagement wall 110 can extend toward the interior region 114 such that at least the portions of the engagement wall 110 surrounding the opening 112 are proximal of the distal terminus of the capture structure 100, even in the resting state.

Figure 2C:
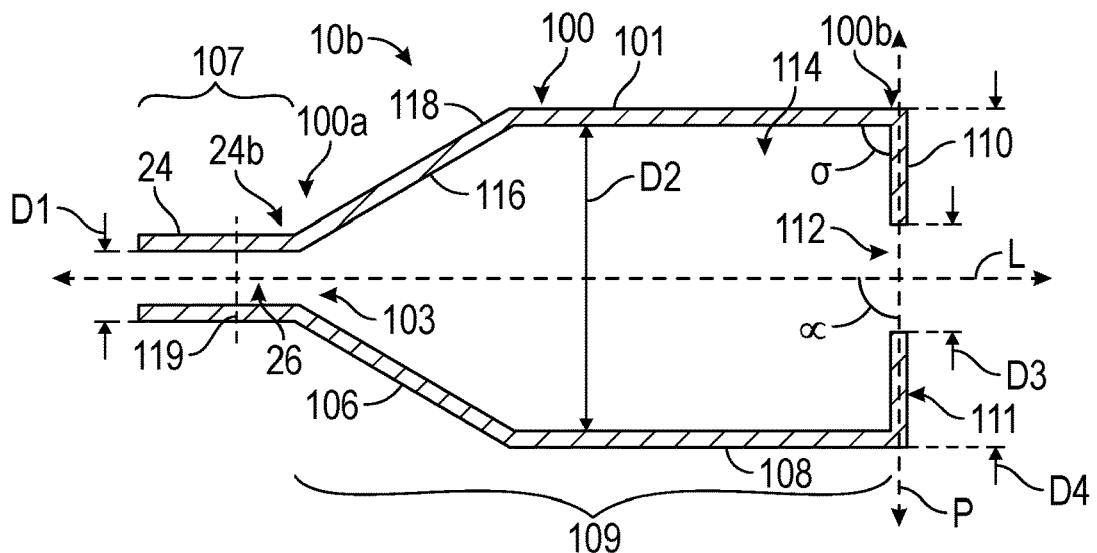
FIG. 2C is a partially schematic cross-sectional side view of the distal portion of the treatment system shown in FIGS. 2A and 2B.

As best shown in FIGS. 2B and 2C, the engagement wall 110 can extend radially inwardly from the annular distal end of the sidewall 109. The engagement wall 110 can lie in a plane P that is substantially perpendicular to a longitudinal axis L of the capture structure 100 (as shown in FIGS. 2A-2D), or the engagement wall 110 may extend radially inwardly from the sidewall 109 in a proximal direction (as shown in FIG. 5A), or may extend radially inwardly from the sidewall 109 in a distal direction (as shown in FIG. 5B). In some embodiments, for example as shown in FIG. 5H, the engagement wall 110 lies within a plane P that is angled relative to the longitudinal axis L of the capture structure 100. In such embodiments, the engagement wall 110 can have a more distal leading edge 120 and a more proximal trailing edge 122. Such a configuration can be beneficial for locating an orifice 112 in the engagement wall 110 at or adjacent to the obstructive material, dislodging obstructive material from a vessel wall, and/or receiving the obstructive material within the interior region 114 of the capture structure 100. For example, the capture structure 100 can be rotated about its longitudinal axis L to align the orifice 112 with obstructive material located at various circumferential locations within a blood vessel. Such a configuration can also enhance collapsibility of the capture structure 100.

The engagement wall 110 can have an orifice 112 configured to receive obstructive material therethrough. As shown in the partially schematic cross-sectional view of the capture structure 100 in FIG. 2C, the orifice 112 can have a resting cross-sectional dimension D3 that is less than a cross-sectional dimension D2 of the interior region 114 of the capture structure 100 in the expanded state. As such, the capture structure 100 initially presents a smaller aspiration area (as compared to a capture structure without the engagement wall 110), which can be especially beneficial when aspirating obstructive material smaller than an inner cross-sectional dimension of the capture structure 100. The engagement wall 110 and orifice 112 provide a reduced cross-sectional aspiration area during initial aspiration that reduces the unintended collateral aspiration of blood and thus helps limit unnecessary blood loss during the procedure.

In any of the embodiments disclosed herein, the resting cross-sectional dimension D3 of the orifice 112 can be of from about 1 mm to about 10 mm. In those embodiments in which the orifice 112 comprises a slit or puncture in the engagement wall 110, the resting cross-sectional dimension D3 of the orifice 112 is effectively zero. Additional details regarding slits and punctures are discussed below with reference to FIGS. 6A-6D.

In some embodiments, the resting cross-sectional dimension D3 of the orifice 112 can be less than an inner cross-sectional dimension D2 of the capture structure 100 but greater than an inner cross-sectional dimension D1 of the elongated shaft 24. In such embodiments, the capture structure 100 is configured to provide an aspiration cross-sectional area and force that is greater than the aspiration cross-sectional area and force would be if aspiration were applied only through the opening at the distal end of the elongated shaft 24. According to some embodiments, the resting cross-sectional dimension D3 of the orifice 112 can be less than an inner cross-sectional dimension D2 of the capture structure 100 and less than an inner cross-sectional dimension D1 of the elongated shaft 24. Reducing the size of the orifice 112 can be desirable for containing captured obstructive material within the interior region 114 of the capture structure 100 and limiting egress of captured material through the orifice 112.

Figure 2D:
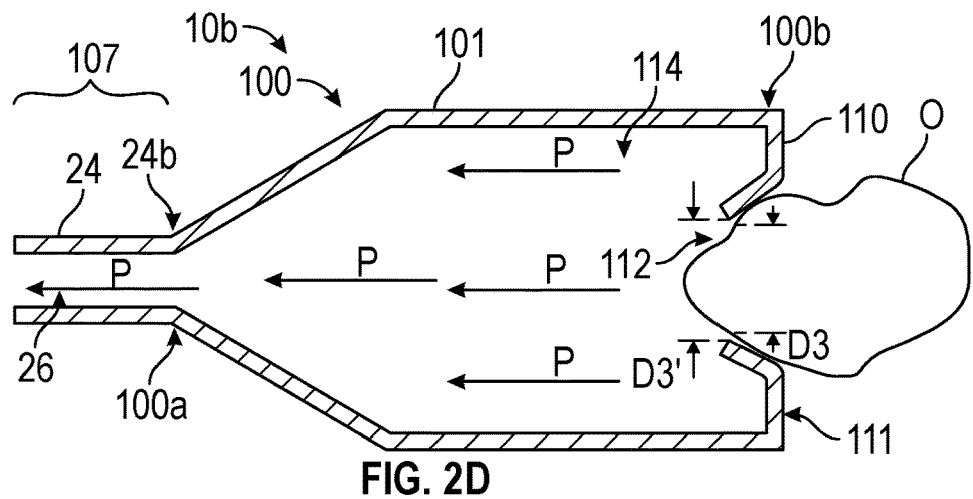
FIG. 2D schematically depicts the capture structure shown in FIG. 2C engaging obstructive material.

In some embodiments, the engagement wall 110 can comprise a material configured to deform in response to negative pressure and/or engagement with the obstructive material. The engagement wall 110, for example, can be configured to stretch and/or bend proximally in response to proximally-directed negative pressure. The engagement wall 110 can also be configured to stretch and/or bend to accommodate progressively larger portions of obstructive material urged into contact with the opening. With or without aspiration, the capture structure 100 can be urged distally against obstructive material, which can exert an opposing force on the engagement wall 110. As depicted in FIG. 2D, for example, the engagement wall 110 can stretch, bend, and/or otherwise deform to adapt to the size of the obstructive material and enlarge a cross-sectional dimension D3 of the orifice 112 (from D3 to D3'). The increased cross-sectional area of the orifice 112, in turn, simultaneously allows more material to be aspirated and increases an aspiration force applied on the obstructive material (described in greater detail below with reference to FIGS. 4A-4C). While the obstructive material is positioned through the orifice 112, the portion of the engagement wall 110 surrounding the orifice 112 can elastically constrict the obstructive material and thus secure the obstructive material in the absence or reduction of aspiration engagement. In such cases, the radially inward force applied to the material by the portion of the engagement wall 110 surrounding the orifice 112 can be greater than the force generated by the blood acting on the material hanging outside of the capture structure 100 but less than the force generated by the negative pressure source through the elongated shaft 24. As such, the orifice 112 is configured to engage the obstructive material in such a way that prevents the obstructive material from escaping the capture structure 100 yet still allows the material to continue to advance through the lumen of the elongated shaft 24 to a location outside of the body.

Figure 2E:
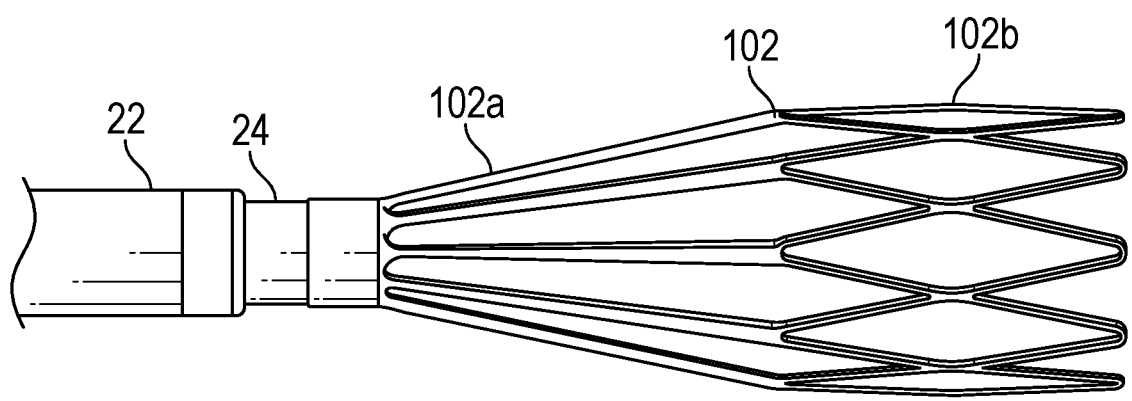
FIG. 2E is an enlarged side view of the distal portion shown in FIGS. 2A and 2B.
Figure 2F:
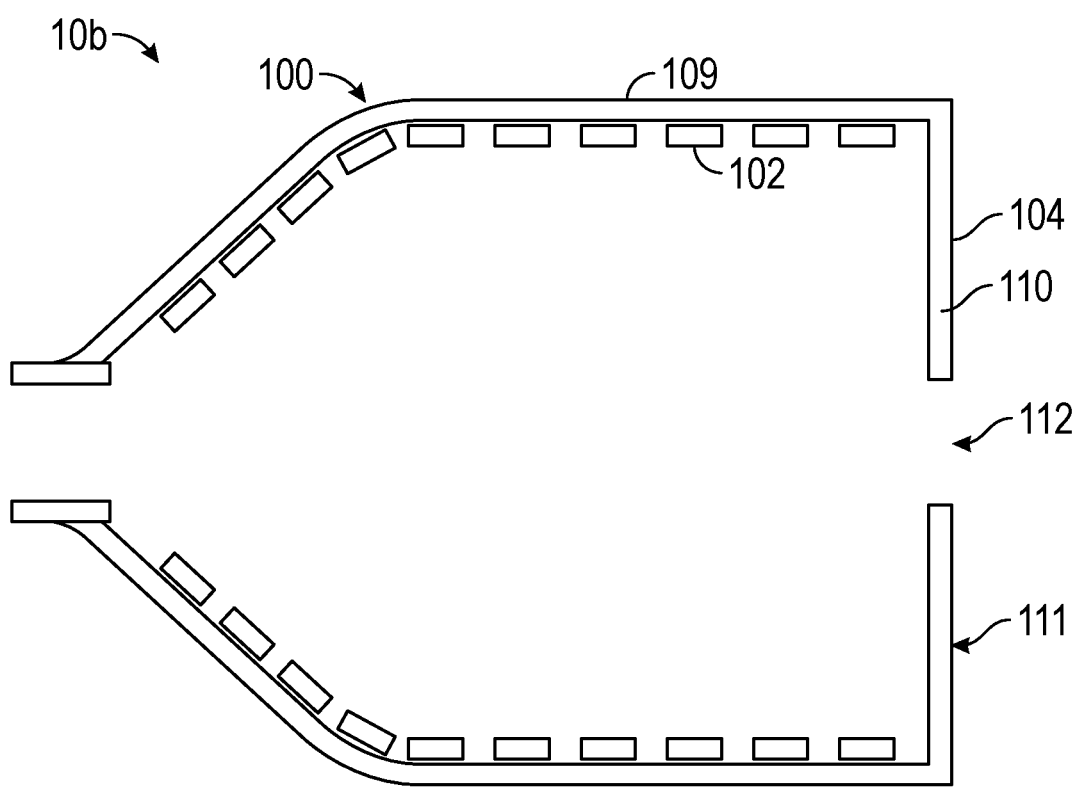
FIG. 2F is a partially schematic cross-sectional side view of the distal portion of the treatment system shown in FIGS. 2A-2E.

In some embodiments, the wall defining the capture structure 100 comprises a frame and a cover. For example, the wall of the capture structure 100 can comprise a frame 102 and a cover 104 disposed on the frame 102. FIG. 2E shows the capture structure 100 with the cover 104 removed for better visualization of the frame 102. FIG. 2F is a partially schematic cross-sectional view of the capture structure 100 showing the frame 102 and the cover 104. The frame 102 is configured to provide structural support to the capture structure 100 while the cover 104 provides a fluid impermeable layer that protects the interior region 114 and enables creation of an aspiration lumen within the interior region 114.

Figure 3:
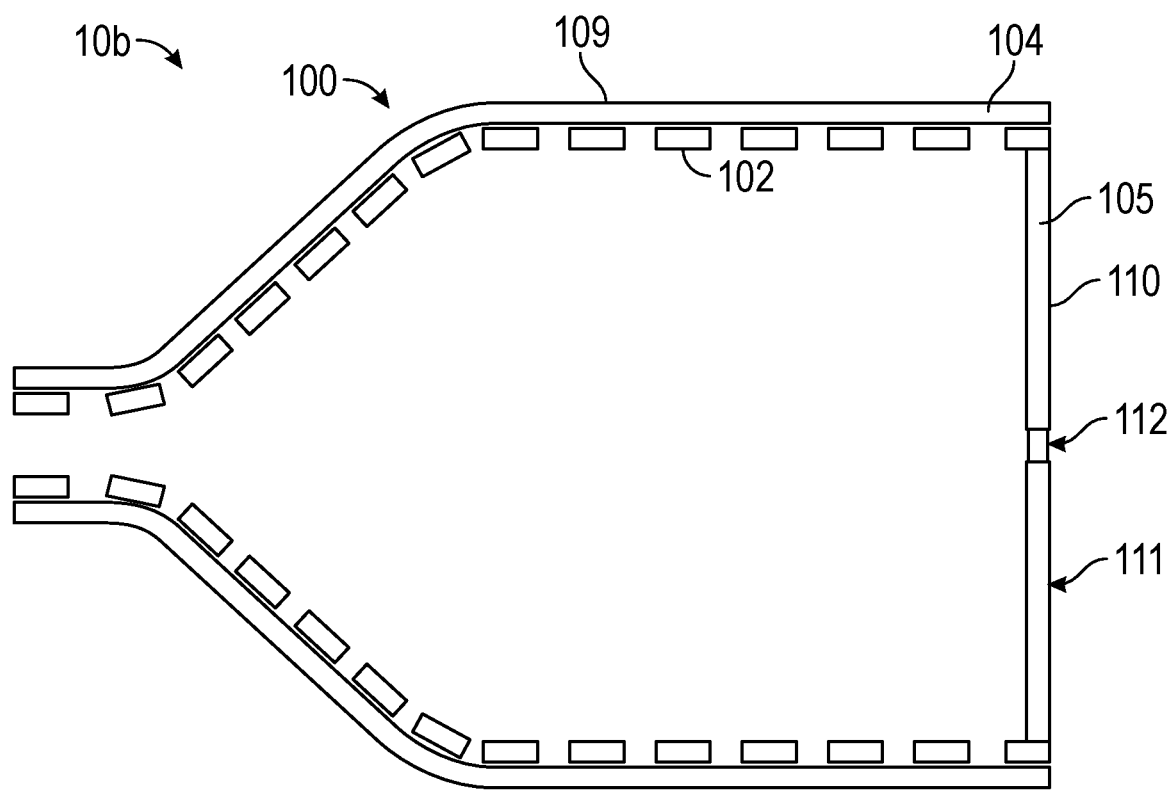
FIG. 3 is a partially schematic cross-sectional side view of a distal portion of a treatment system configured in accordance with several embodiments of the present technology.

Referring to FIGS. 2E and 2F, the cover 104 can be positioned within a lumen of the frame 102 (not shown), on an outer surface of the frame 102, and/or within a thickness of the frame 102 (e.g., extending between pores of the frame 102 at a radial location that does not extend beyond the abluminal and luminal surfaces of the frame 102) (not shown). In some embodiments, the portion of the cover 104 of the tubular sidewall 109 is monolithic and/or integral with the portion of the cover 104 of the engagement wall 110. For example, the cover 104 can have an open proximal end and a closed distal end such that, when the cover 104 is positioned over the frame of the tubular sidewall 109, the closed distal end of the cover 104 forms the engagement wall 110. In some embodiments, the engagement wall 110 can be formed separately from the frame and/or cover forming the tubular sidewall 109 (for example, as shown in FIG. 3).

The engagement wall 110 can comprise the same material as the frame 102 and/or cover 104 or can comprise a different material from the frame 102 and/or cover 104. In some embodiments, engagement wall 110 can be formed separately from the tubular sidewall 109 and secured to the sidewall 109 during assembly of the capture structure 100. The cover and/or the material forming the engagement wall 110, if distinct from the cover, can comprise at least one of a film, a coating, a foil, or a sheet. The cover and/or the material forming the engagement wall 110 can comprise a polymer, an elastomer, and/or a rubber. For example, the cover and/or the material forming the engagement wall 110 can comprise a latex or a silicone rubber. The cover and/or the material forming the engagement wall 110 can be configured to elongate, stretch, and/or expand between about 100% and about 1500%. In some embodiments, the cover and/or the material forming the engagement wall 110 can have a durometer of between about 10 on the Shore 00 hardness scale to about 60 on the Shore A hardness scale, about 0 on the Shore A hardness scale to about 40 on the Shore A hardness scale, or about 10 on the Shore A hardness scale to about 30 on the Shore A hardness scale. The cover and/or the material forming the engagement wall 110 can have a thickness of less than about 0.5 mm, less than about 0.4 mm, less than about 0.3 mm, less than about 0.2 mm, less than about 0.1 mm, less than about 0.05 mm, less than about 0.01 mm, less than about 5 µm, less than about 1 µm, less than about 0.5 µm, or less than about 0.1 µm.

The engagement wall 110 can comprise a portion of the cover 104 (discussed in greater detail below) or may be a separate component that is joined to the frame 102 and/or cover 104. For example, in the more detailed view shown in FIG. 2F, the cover 104 can extend across a break in the frame 102 and form the engagement wall 110. In some embodiments, the engagement wall 110 comprises a separate component from the cover 104 and the frame 102. FIG. 3, for example, shows a capture structure 100 having a frame 102, a cover 104, and an engagement wall 110 comprising a separate material 105 coupled to the distal portions of the frame 102 and cover 104. In some embodiments the engagement wall 110 includes a portion of the frame 102, and in some embodiments the engagement wall 110 comprises only the cover 104. In some embodiments, substantially all of the wall includes both the frame 102 and the cover 104. According to several embodiments, the frame 102 is only positioned at the sidewall 109 and/or neck portion 107 and not along the engagement wall 110. Said another way, in such embodiments the engagement wall 110 comprises only the cover 104 and does not include the frame 102. In some embodiments, the wall of the capture structure 100 comprises a single structure that provides both the structural support and the fluid impermeable cover. For example, in some embodiments the capture structure 100 comprises a resilient polymer structure.

The frame 102 can have any suitable shape or cross-sectional dimension. In some embodiments, the shape of the capture structure 100 substantially follows the shape of the frame 102. The frame 102 can comprise a single continuous structure, or may comprise a plurality of separate structures. In some embodiments, the frame 102 comprises a mesh structure formed of a resilient and/or superelastic material configured to self-expand when released from the sheath 22 or other radially constraining structure of the system. According to several embodiments, the mesh structure comprises a laser-cut tube or sheet of material. The material, for example, can comprise a resilient, elastic, and/or superelastic metal alloy or polymer. In such embodiments, the frame 102 can comprise a plurality of interconnected struts defining a plurality of cells therebetween. In some embodiments, the mesh structure comprises a plurality of braided wires (e.g., filaments, threads, sutures, fibers or the like) that have been interwoven to form a structure having openings. In some embodiments, the mesh structure is formed of a single braided or woven wire. The mesh and/or braid can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate (PET), polylactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium, or alloys of any of these metals. In certain embodiments including at least metal, some or all of the surface of the frame 102 may be highly polished and/or surface treated to further improve its hemocompatibility. The frame 102 can be constructed solely from metallic materials without the inclusion of any polymer materials, solely from polymer materials without the inclusion of any metallic materials, or a combination of polymer and metallic materials.

In those embodiments where the frame 102 comprises a braided structure, some or all of the wires forming the braided structure can be drawn-filled tube ("DFT") wires having a radiopaque core (e.g., platinum, tantalum, gold, tungsten, etc.) surrounded by an elastic or superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires. Moreover, some or all of the wires may have a wire diameter of about 0.003 inches to about 0.015 inches (e.g., 0.008 inches, 0.009 inches, 0.01 inches, etc.). In some embodiments, all of the wires have the same diameter, and in other embodiments some of the wires have different diameters.

The cover 104 can comprise a polymeric coating, a thin film, a membrane, or other fluid impermeable material. Additionally or alternatively, the cover 204 can comprise a stretchable material such as a low durometer polymer or silicone. The cover 104 can be configured to deform during aspiration and/or in response to forces applied by the obstructive material. As used herein, "deform" can refer to stretching, bending, or both. In some embodiments, the engagement wall 110 comprises a separate material and/or component from the cover 104.

In order to optimize the volume of the interior region 114 of the capture structure 100, the capture structure 100 can have the lowest wall thickness required to withstand a desired negative pressure. For example, in some embodiments the capture structure 100 has a wall thickness that is from about 0.1 mm to about 0.5 mm, less than 0.3 mm, or less than 0.5 mm, and is configured to withstand a negative pressure of from about 0 mmHg to about 760 mmHg, about 100 mmHg to about 600 mmHg, about 100 mmHg to about 500 mmHg, about 100 mmHg to about 450 mmHg, about 0 mmHg to about 500 mmHg, about, about 0 mm Hg to about 200 mm Hg, about 10 mmHg to about 500 mmHg, about 100 mmHg to about 500 mmHg, at least 100 mmHg, at least 200 mmHg, at least 300 mmHg, or at least 400 mmHg. The wall of the capture structure 100 can have a substantially constant thickness or may have a varying thickness. For example, in some embodiments the wall of the capture structure 100 is thicker along the sidewall 109 and thinner along the engagement wall 110. According to several embodiments, the wall of the capture structure 100 is thinner along the sidewall 109 and thicker along the engagement wall 110.

The capture structure 100 may be configured to self-expand from the low-profile state to the expanded state upon release of a radial constraint (such as withdrawal of a sheath), or may be actively expandable by an operator, such as via a pull-wire or other expansion mechanism. In some embodiments, the capture structure 100 can be configured to be deployed via both self-expansion and actuation. In some embodiments the capture structure 100 can be expanded via one or more pull-wires, cinching elements, and/or other actuation mechanisms. In some embodiments, the capture structure 100 can be radially expanded and collapsed via axial elongation and compression. For example, in some embodiments the distal end portion of the capture structure 100 structure is coupled to a first elongated member and the proximal end portion of the capture structure 100 is coupled to a second elongated member. The proximal ends of the first and second elongated members can be moved axially relative to one another to expand and collapsed the capture structure 100 as desired. In some embodiments, the capture structure 100 is expandable using hydrostatic pressure via a balloon catheter. According to several embodiments, the capture structure 100 is an inflatable structure and can be expanded via fluid delivery. In any case, in the expanded state, the maximum cross-sectional dimension of the capture structure 100 can be 150% to 300% larger than the cross-sectional dimension of the capture structure 100 in its low-profile state.

In some embodiments, the capture structure 100 has an outer cross-sectional dimension no greater than the outer cross-sectional dimension of the elongated shaft 24. According to several embodiments, the capture structure 100 has an outer cross-sectional dimension in the collapsed state that is no greater than 24 Fr. In some embodiments, the capture element 100 has an outer cross-sectional dimension in the collapsed state that is no greater than 22 Fr, no greater than 20 Fr, no greater than 19 Fr, no greater than 18 Fr, no greater than 17 Fr, no greater than 16 Fr, no greater than 15 Fr, or no greater than 14 Fr. In other embodiments, the outer cross-sectional dimension of the capture structure 100 in the expanded state is three times that of outer cross-sectional dimension of the elongated shaft 24. In some embodiments, the outer cross-sectional dimension of the capture structure 100 in the expanded state is greater than 8 mm and the outer cross-sectional dimension in the collapsed state is less than 8 mm. In some embodiments, a cross-sectional area of the capture structure 100 in the expanded state is greater than or equal to 50% of the diameter of the main right or left pulmonary artery. In some embodiments, the capture structure 100 has additional cross-sectional dimensions.

In some embodiments, an outer cross-sectional dimension of the capture structure 100 in the expanded state is substantially the same as or slightly larger than a diameter of the blood vessel at the treatment site. In such embodiments, the capture structure 100 can be configured to expand into apposition with the blood vessel wall. Contact between the capture structure 100 and the blood vessel wall can help anchor the capture structure 100 in place during the procedure, and can help force the obstructive material into the capture structure 100.

The shape of the capture structure 100 can be configured to facilitate engagement, capture, and containment of the obstructive material. In some instances, the shape of the capture structure 100 can help in shaping, transitioning, forming, compressing, and/or guiding the clot material into the elongated shaft 24. The shape of the capture structure 100 is also configured to provide a therapeutic working space shielded from the surrounding anatomy. In some embodiments, for example as shown in FIGS. 2A-2D, the capture structure 100 has a tapered proximal portion 106 and substantially cylindrical distal portion 108. In some embodiments, the capture structure 100 has a tapered proximal portion, a substantially cylindrical mid-portion, and a distally-tapering distal portion. According to several embodiments, the capture structure 100 has an outer cross-sectional dimension D4 (see FIG. 2D) and/or an inner cross-sectional dimension D2 that remains substantially constant along its entire length. According to several embodiments, the capture structure 100 has an outer cross-sectional dimension D4 and/or an inner cross-sectional dimension D2 that varies along all or a portion of the entire length.

Figure 5F:
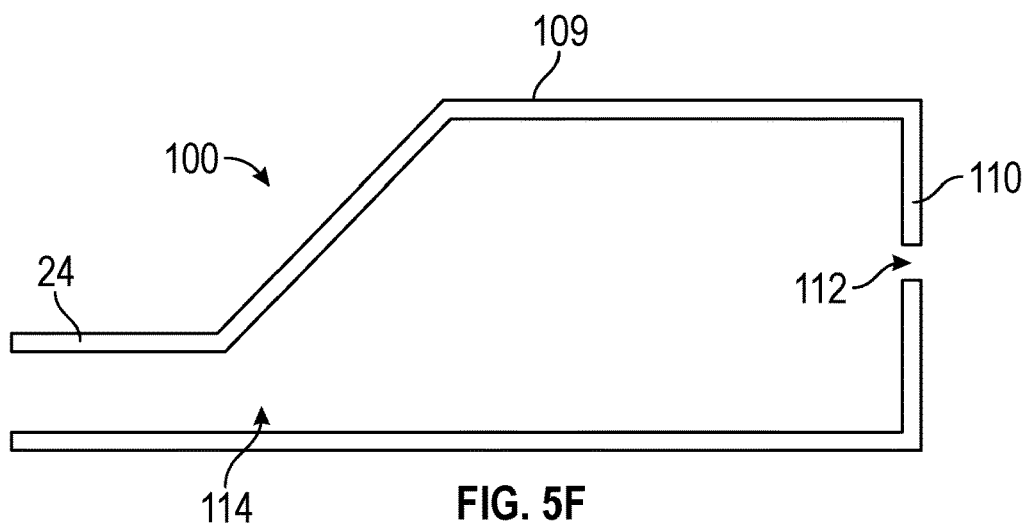

The capture structure 100 can be generally symmetric about its longitudinal axis, or it may be eccentric (for example, as shown in FIG. 5F). The capture structure 100 can have an overall length greater than about 1 cm and less than about 30 cm. In some embodiments the capture structure 100 has an overall length of from about 5 cm to about 20 cm.

Figure 4A:
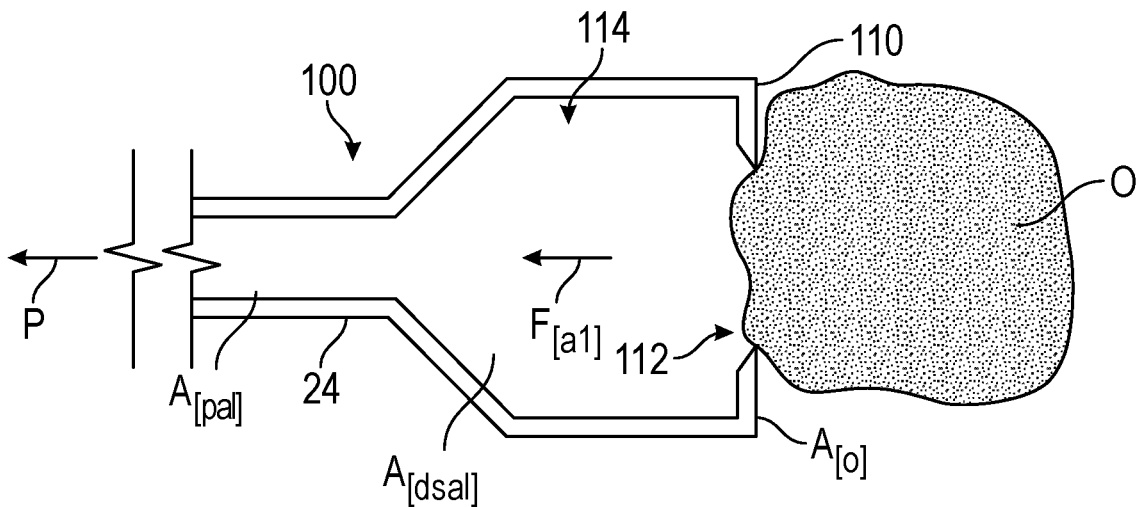
FIGS. 4A-4C show a method for engaging clot material
Figure 4B:
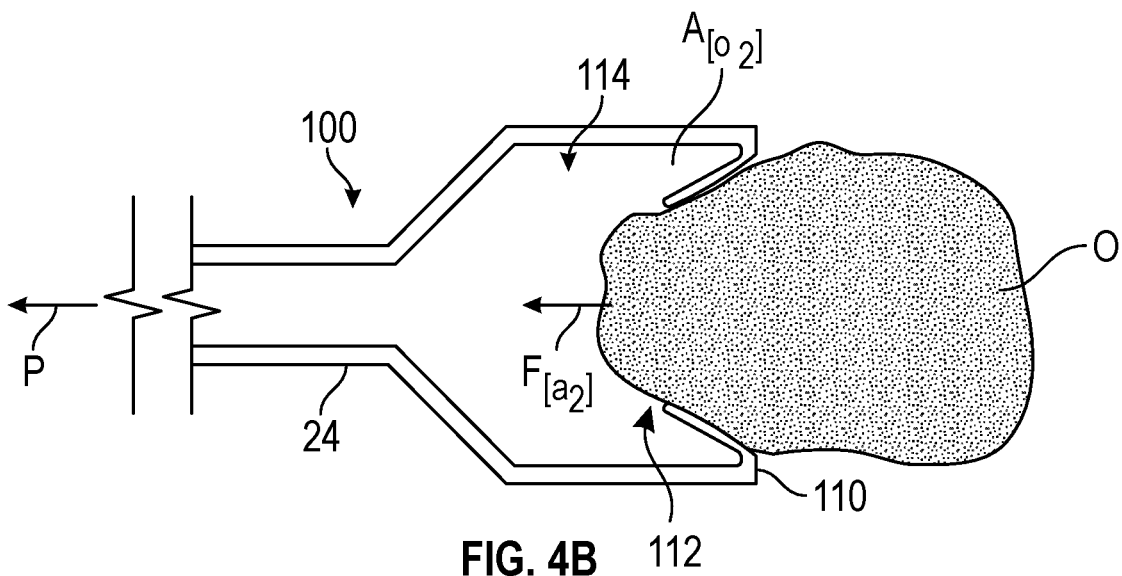
Figure 4C:
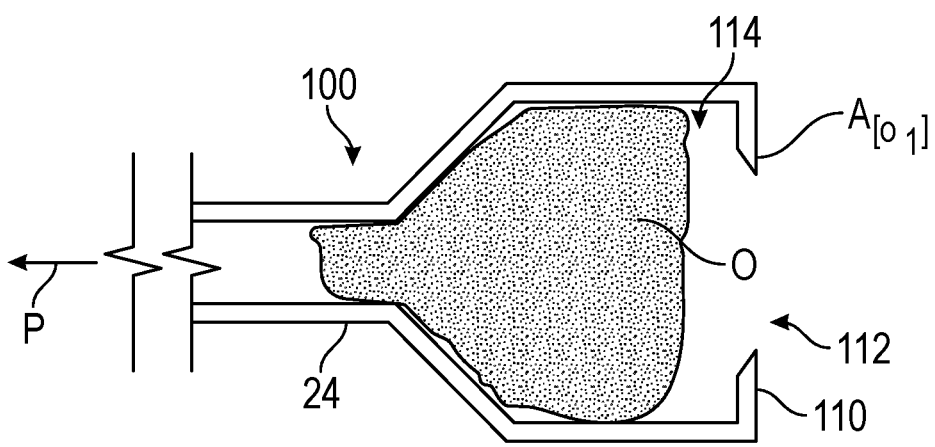

FIGS. 4A-4C illustrate how the deformable engagement wall 110 and orifice 112 can respond as an obstructive material (such as a thrombus) enters into the interior region of the capture structure 100. FIGS. 4A-4C show a distal portion of the system 10 having a proximal aspiration lumen area A[pal] (i.e., a cross-sectional area of an inner diameter of the elongated shaft 24), a capture structure aspiration lumen area A[dsal], and an orifice area adjacent to thrombus O. In this embodiment, the initial orifice area A[ol] is greater than the proximal aspiration lumen area A[pal] and less than the distal section aspiration lumen area A[dsal]. In some embodiments, the initial orifice area is less than or equal to the proximal aspiration lumen and can even have an initial orifice area close to zero when no forces are being applied on the orifice. Once the orifice 112 is adjacent to the thrombus O, a negative pressure P is applied to the lumen of the elongated shaft 24 and creates an initial aspiration force F[a1], as shown in FIG. 4A. As the thrombus O engages with the portion of the engagement wall 110 surrounding the orifice 112, the engagement wall 110 deforms such that the orifice 112 increases to a second orifice area which increases the aspiration force on the thrombus as the negative pressure stays constant, as shown in FIG. 4B. In FIG. 4B, the second orifice area and aspiration force are depicted as A[o2] and F[a2], respectively. This increase in force continues until the orifice area A[o] reaches the size of the capture structure aspiration lumen area A[dsal] or the thrombus passes through the orifice at which point the orifice area will return to the initial orifice area as shown FIG. 4C. By way of example for this embodiment, the initial orifice area A[ol] is 0.02-in2 and a negative pressure of 2-psi is applied to the central lumen of the flexible body generating an initial aspiration force F[a1] of 0.04-lbs. As the thrombus enters the distal section, the new orifice area A[o2] is 0.08 applying an increased aspiration force F[a2] of 0.16-lbs.

Figure 5G:
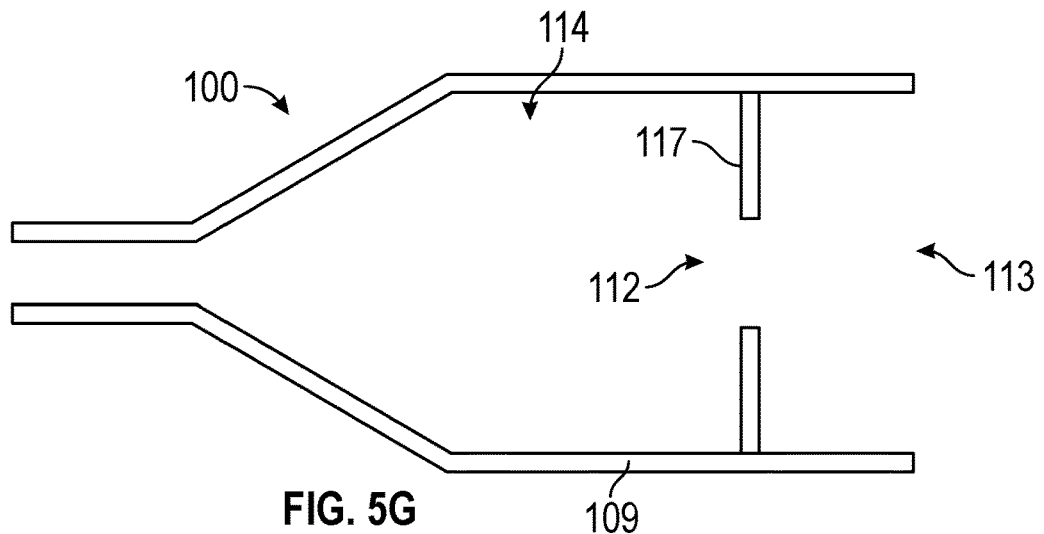
Figure 5H:
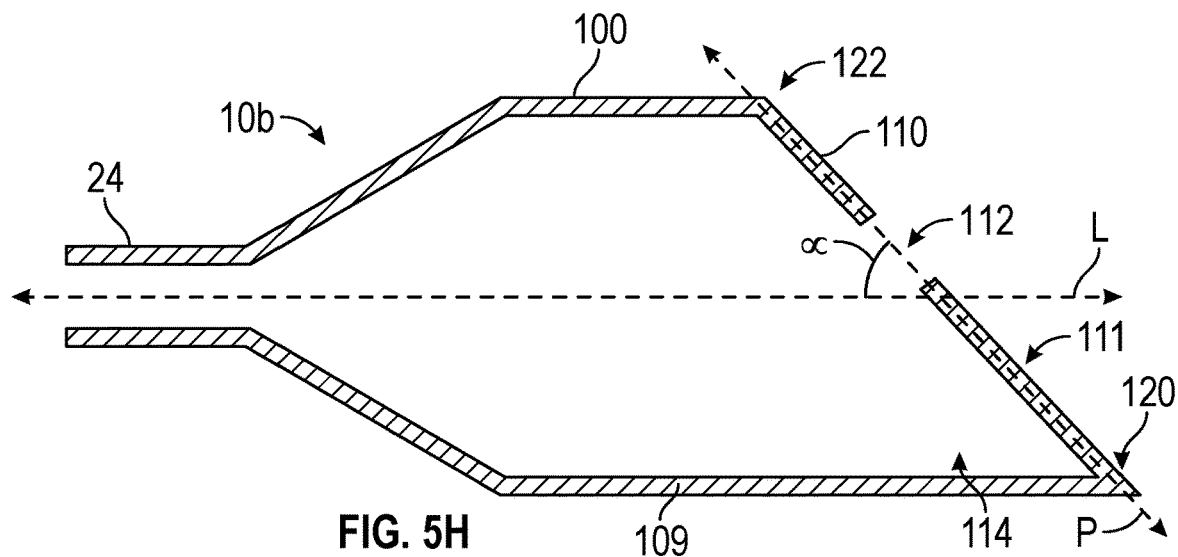
Figure 5I:
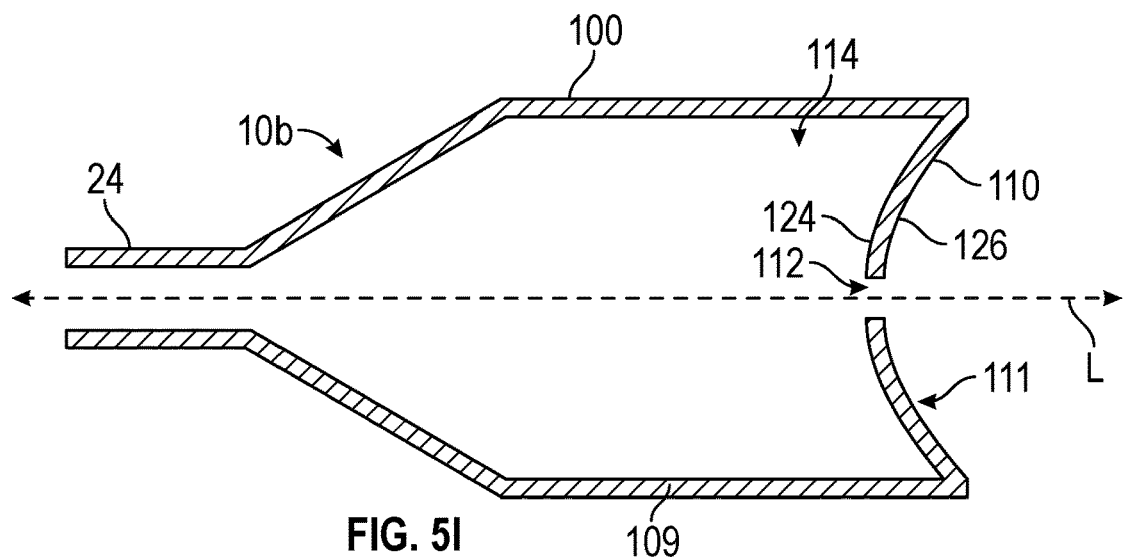

FIGS. 5A-5G illustrate different capture structure 100 configurations in accordance with the present technology. For example, as shown in FIG. 5A, in some embodiments the engagement wall 110 of the capture structure 100 can be angled inwardly, towards an interior region 114 of the capture structure 100. As shown in FIG. 5B, in some embodiments the engagement wall 110 of the capture structure 100 can be angled outwardly, away from an interior region 114 of the capture structure 100. As shown in FIGS. 5C and 5D, in some embodiments the orifice 112 and deformable wall can be disposed along a distal portion of the sidewall 109 or a proximal portion of the sidewall, respectively. Placement of an orifice at the sidewall 109 can be advantageous when attempting to engage and/or capture obstructive material positioned laterally of the capture structure 100. As illustrated by the capture structure 100 shown in FIG. 5E, in some embodiments the capture structure 100 can have multiple orifices 112/deformable wall portions. In such embodiments, the orifices 112 can be positioned anywhere along the sidewall 109 and/or engagement wall 110. The capture structure 100 can include two, three, four, five, six or any number of orifices. As illustrated by the capture structure 100 shown in FIG. 5F, in some embodiments the capture structure 100 can be asymmetric and/or the orifice 112 can be offset from the lumen of the elongated shaft 24. As shown in FIG. 5G, in some embodiments the orifice 112 and supporting wall 117 can be inset from a distal end of the sidewall 109 such that the capture structure 100 has a distal opening 113 and the wall 117 is proximal of the distal opening 113. As shown in FIG. 5H, in some embodiments the engagement wall 110 is beveled. As shown in FIG. 5I, in some embodiments all or a portion of the engagement wall 110 is curved. In such embodiments, the engagement wall 110 can have (a) an inner surface 124 that is convex towards the interior region 114, at least when the engagement wall 110 is in a resting state, and (b) an outer surface 126 (or engagement surface 111) that is concave towards an exterior of the capture structure 100 and/or obstructive material, at least when the engagement wall 110 is in a resting state.

FIG. 6A is a cross-sectional side view of a capture structure 100 having an orifice 112 comprising a slit 115. An end view of the slit 115 is shown in FIG. 6B. The slit 115 can comprise an elongated break in the continuity of the engagement wall 110 and/or any wall of the capture structure 100. In some embodiments, the adjacent surfaces 119 of the wall defining the slit 115 abut and/or are in contact with one another when the wall 110 is in an unstretched state and/or only a nominal clearance exists between the surfaces 119. For example, the portions of the wall defining the slit 115 and/or opening can be in contact but moveable relative to one another. As such, the engagement wall 110 comprising a slit 115 presents a substantially closed, fluid impermeable surface when the engagement wall 110 is not being deformed by aspiration and/or engagement with obstructive material. The cross-sectional dimension of the slit 115 in this resting state is approximately zero. When aspiration is applied within the capture structure 100 and/or when the engagement wall 110 is pushed up against the obstructive material, the engagement wall 110 deforms, causing the distance between the abutting surfaces defining the slit 115 to move apart from one another, thereby increasing the cross-sectional dimension to a value greater than zero and enabling the obstructive material to move through the slit into the interior region 114 of the capture structure 100.

In some embodiments, the orifice 112 can comprise a plurality of intersecting slits 115, for example as shown in FIG. 6C. According to several embodiments, the orifice 112 can comprise a single puncture 121 and/or pinhole in the engagement wall 110 and/or any wall of the capture structure 100. In some embodiments, the orifice 112 can comprise multiple punctures in the engagement wall 110 and/or any wall of the capture structure 100.

For any of the treatment systems disclosed herein, the system and/or any component thereof (such as elongated shaft 24, sheath 22, a disrupting device, etc.) can have an overall length of 80 cm or greater. For example, when separate elongated members are used for control of the sheath, the capture structure, and the disrupting device, any one of the individual elongated members can have a length 80 cm or greater. Any of the elongated members and/or elongated shafts disclosed herein can have a length less than or greater than 80 cm. Moreover, any of the elongated member and/or members disclosed herein (such as the elongated shaft 24, the sheath 22, a disrupting device, etc.) can have a flexibility that progressively increases in a proximal to distal direction such that the proximal portion of the respective elongated member has a greater column strength (for improved pushability) and the distal portion has better maneuverability. In some embodiments, one, some, or all of the elongated members have a substantially constant flexibility along their respective lengths.

According to some embodiments, a method for treating a blood vessel of a human patient, such as a pulmonary blood vessel, comprises positioning a distal portion of a treatment device in the blood vessel at a treatment site proximate obstructive material, the treatment device comprising an elongate shaft and a capture structure (such as any of the capture structures disclosed herein) disposed at a distal portion of the elongate shaft and enclosing an interior region. In some embodiments, the capture structure and elongated shaft are delivered through a delivery sheath. In some embodiments, the capture structure and elongated shaft are not delivered through a delivery sheath. The method can include engaging the obstructive material with the distal face of the capture structure such that at least a portion of the obstructive material is positioned in and/or through the orifice, thereby increasing a cross-sectional dimension of the orifice. The method can further include removing at least the portion of the obstructive material from the patient's body.

Negative pressure can be applied to the interior region of the capture structure before, during, and/or after engaging the obstructive material, thereby pulling the obstructive material through the orifice and into the interior region. In some cases, negative pressure is only applied once the obstructive material is engaged and/or while the obstructive material is moving through the opening, thereby reducing the volume of blood aspirated during a typical procedure (as compared to conventional thrombectomy systems that utilize aspiration).

In some embodiments, the method comprises increasing a proximally-directed force on the obstructive material without increasing the negative pressure. For example, in some embodiments, engaging the obstructive material comprises pushing the engagement wall onto and/or over a portion of the obstructive material. Forcible contact between the engagement wall and the obstructive material can cause the engagement wall to deflect inwardly, toward the interior region. This inward deflection stretches the engagement wall, which enlarges the opening and enables a greater volume of obstructive material to enter the interior region of the capture structure. In those embodiments where aspiration is being applied while the obstructive material is engaged with the opening and/or engagement wall, enlarging the opening increases the aspiration force on the obstructive material. In several embodiments, engaging the obstructive material comprises creating a seal between the obstructive material and an edge of the engagement wall surrounding the orifice.

In some embodiments, the method comprises positioning a disruptor within the interior region of the capture structure before, during, and/or after engaging the obstructive material. The disruptor can break up the portion of the obstructive material positioned within the interior region of the capture structure to facilitate removal through the aspiration lumen. In some embodiments, the disruptor mechanically engages the obstructive material and pulls the obstructive material into the interior region of the capture structure 100. According to several methods, the disrupting device can be removed from the patient's body while holding the capture structure at the treatment site.

In some embodiments, the method comprises applying negative pressure to the interior region of the capture structure before, during, and/or after engaging the obstructive material, and breaking up the portion of the obstructive material positioned within the interior region with a disrupting element positioned within the interior region. In these and other embodiments, applying the negative pressure and breaking up the obstructive material occur at different times.

In some embodiments, the method comprises applying negative pressure to the interior region of the capture structure before, during, and/or after engaging the obstructive material, and breaking up the portion of the obstructive material positioned within the interior region with a disrupting element positioned within the interior region. In these and other embodiments, at least some of the application of negative pressure occurs while the disrupting element is breaking up the obstructive material, or vice versa.

In some embodiments, the method comprises engaging the obstructive material such that all or a portion of the obstructive material extends through the opening and is positioned within the interior region of the capture structure. During engagement, aspiration may or may not be applied. Once the obstructive material (or a portion thereof) is positioned within the interior region, the disrupting element can be activated to disrupt the obstructive material so that the obstructive material can be pulled (or more easily pulled) through the lumen of the elongated shaft. It may be beneficial to cease aspiration (if aspiration was being used prior to activation of the disrupting element) during the disrupting of the obstructive material by the disrupting element in order to limit the volume of blood pulled from the patient's body during the procedure. Once the obstructive material is sufficiently processed, aspiration can be started again to pull the processed obstructive material through the elongate shaft to a proximal portion of the system. The steps of pulling or otherwise forcing all or a portion of the obstructive material into the capture structure, disrupting the obstructive material that is within the capture structure with the disrupting element without any aspiration, then aspirating the processed obstructive material can be repeated as many times as necessary to remove the desired obstructive material.

III. Selected Embodiments of Capture Structures

FIGS. 7A-11E show and describe examples of capture structures configured for use with any of the treatment systems and/or disrupting devices disclosed herein. FIGS.

Figure 7A:
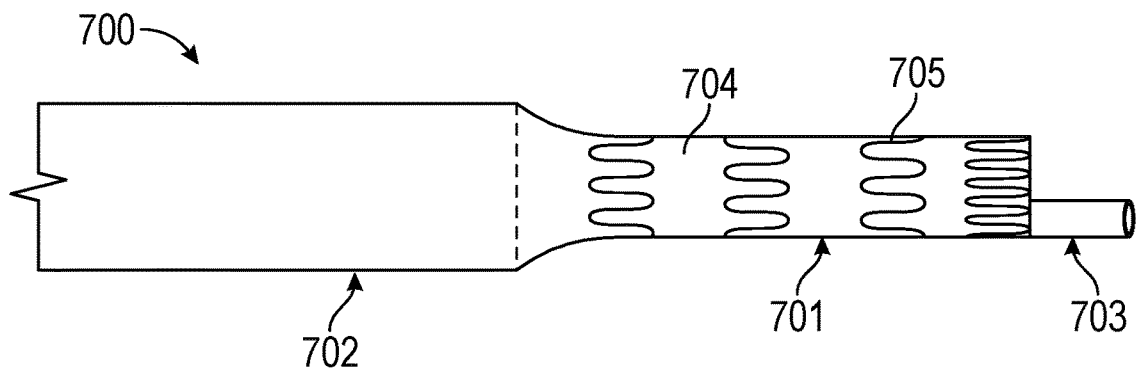
FIGS. 7A-7C show a capture structure configured in accordance with several embodiments of the present technology in different configurations.
Figure 7B:
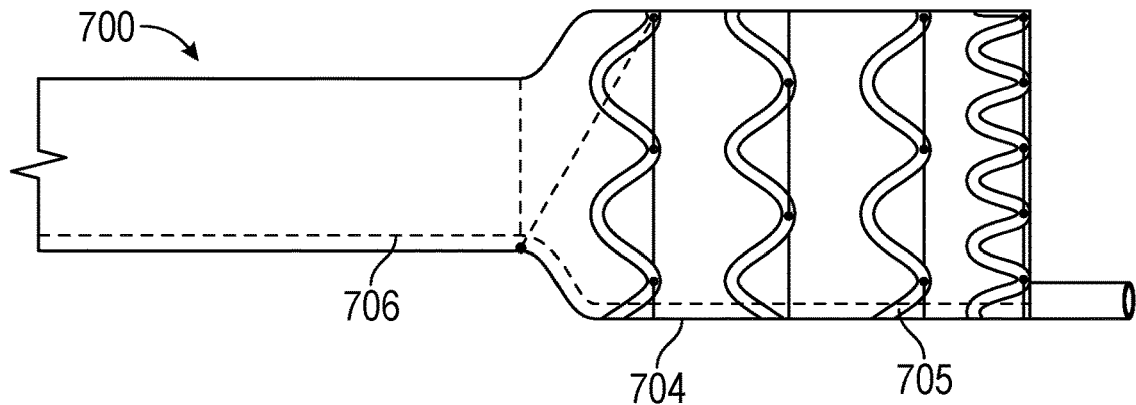
Figure 7C:
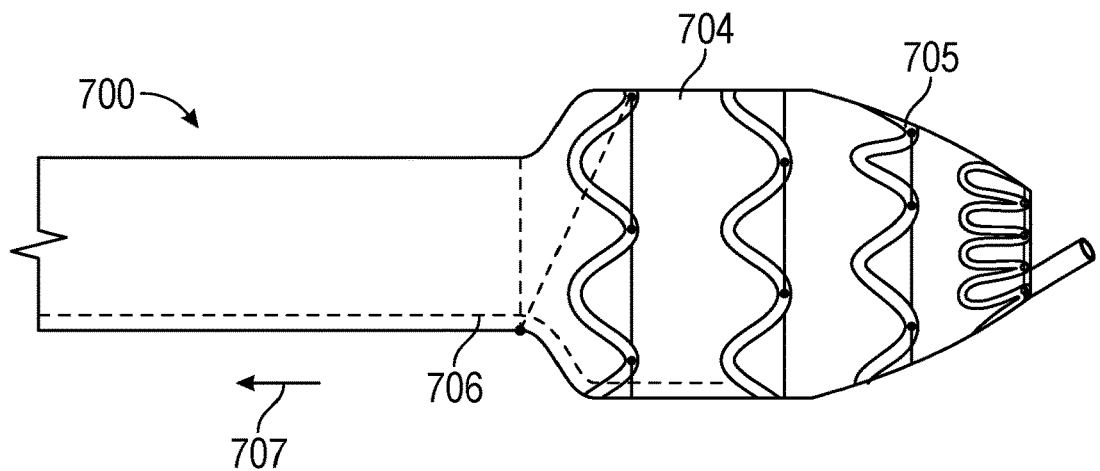

7A-7C, for example, show a distal portion of a treatment system 700 with a capture structure 701 in various configurations in accordance with several embodiments of the present technology. The system 700 can comprise an elongated shaft 702, a capture structure 701 carried by a distal region of the elongated shaft 702, and a guidewire shaft 703 radially offset from the central longitudinal axis of the shaft 702 and/or system 700. In some embodiments, the guidewire shaft 703 can be coupled to all or a portion of an inner surface of the sidewall of the elongated shaft 702 and/or capture structure 701. The system 700 can further include a deployment member 706 coupled to the capture structure 701 and configured to retain the capture structure 701 in a low-profile and/or constrained state, as shown in FIG. 7A. The deployment member 706 can be a wire, thread, suture, coil, and/or other flexible member.

Figure 8A:
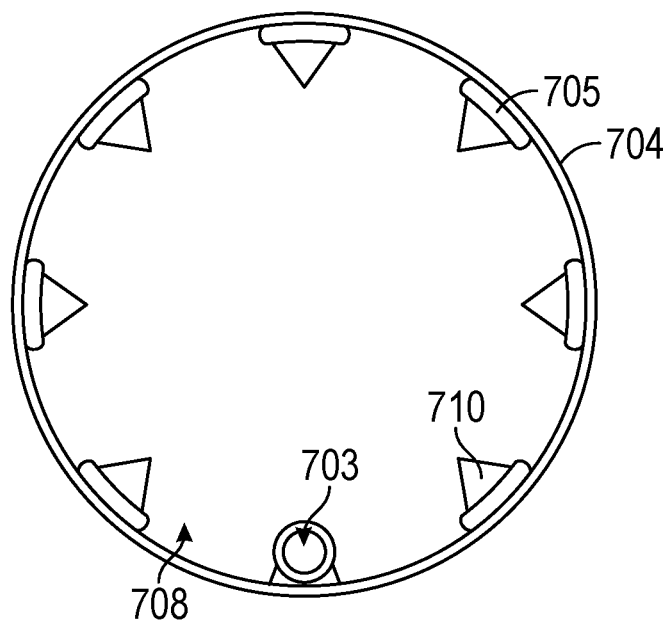
FIGS. 8A and 8B are cross-sectional end views taken of the capture structure as depicted in FIG. 7B and FIG. 7C, respectively.
Figure 8B:
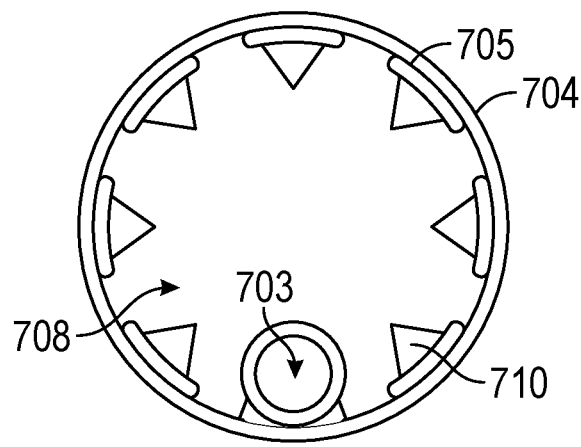

The system 700 is configured such that a user can manipulate the tension in the deployment member 706 to increase or decrease a diameter and/or length of the capture structure 701. For example, in some embodiments the capture structure 701 can be expanded to a radial profile greater than the elongated shaft 702 by releasing the deployment member 706. When the deployment member 706 is released, the frame 705 of the capture structure 701 expands and the capture structure film 704 stretches and expands with the scaffolding rings. The scaffolding rings 705 are axially held in place with metallic connector shafts (not shown) positioned on the top and bottom sides of the capture structure. The scaffolding rings are thermally bonded or sutured to the film 704 creating a fluid tight central lumen that runs throughout the elongated system 700. The scaffolding rings 705 can be made out of cobalt-chromium, shaped memory alloy that has a transition temperature near body temperature, or super elastic nitinol material. The film 704 is made from a thermoplastic elastomer or polyurethane. The guidewire lumen 703 has a lubricious inner liner that accommodates guidewires between 0.020-0.038 in. The guidewire lumen also has the cross section area sufficient to allow the user to inject contrast media through the lumen to perform an angiography image to confirm location of the device and the thrombus. The guidewire lumen 703 is positioned axially to the system 700 but off the centerline to not obstruct the aspiration lumen during the digesting of large thrombus also having a guidewire lumen integrated into the central lumen provides the guidewire more support and helps the system follow the guidewire because of the inner diameter of the guidewire lumen 703 and the outer diameter of the guidewire. When the system 700 needs to be repositioned or has started to ingest a large volume of thrombus, the deployment wire 706 is pulled using an axial force 707 causing the capture structure to collapse distal to proximal. If this collapsing is performed when thrombus is present, the collapsing movement assists in advancing the thrombus through the central lumen 708 proximally. Also as shown in FIGS. 8A and 8B, the frame 705 can have sharp barbs or blades 710 pointing radially inwardly (toward the lumen 708) to assist in morcellating the thrombus to ease in digesting the thrombus.

Figure 10B:
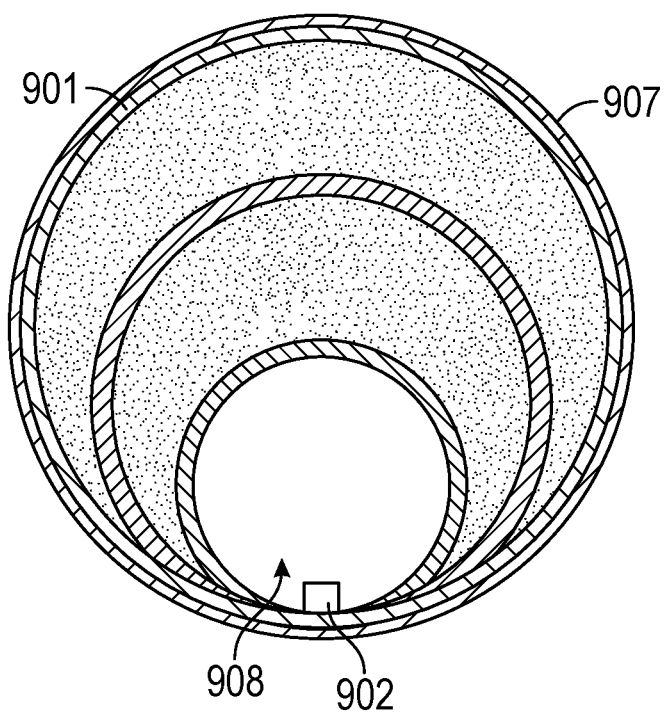
FIG. 10B is a cross-sectional end view taken along line 10B-10B in FIG. 10A.
Figure 11A:
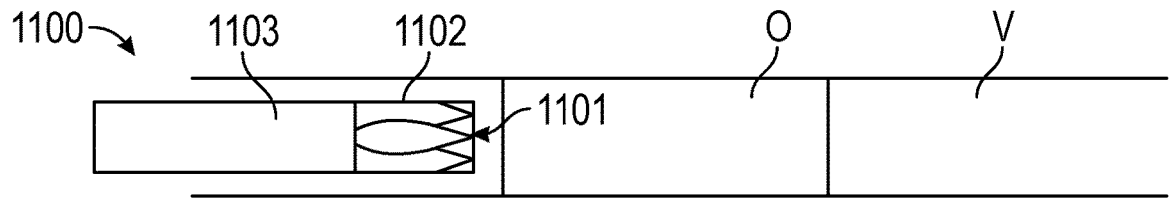
FIGS. 11A-11E show a method for disrupting and/or removing obstructive material using a treatment system configured in accordance with the present technology.
Figure 11B:
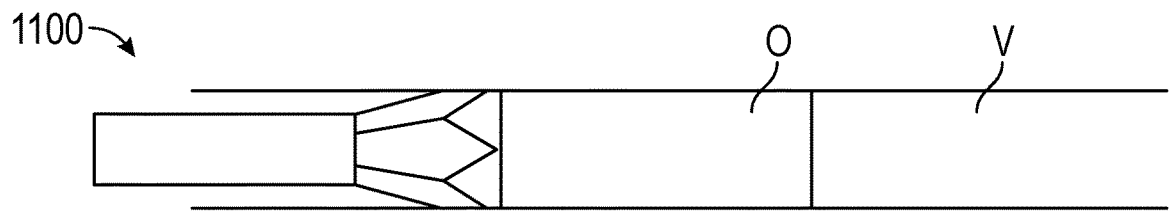
Figure 11C:
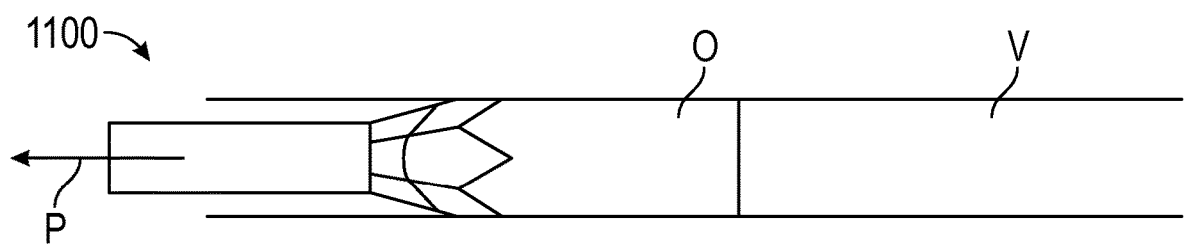
Figure 11D:
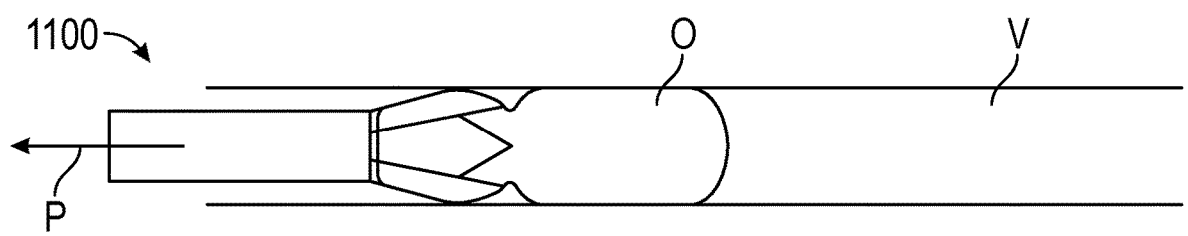
Figure 11E:
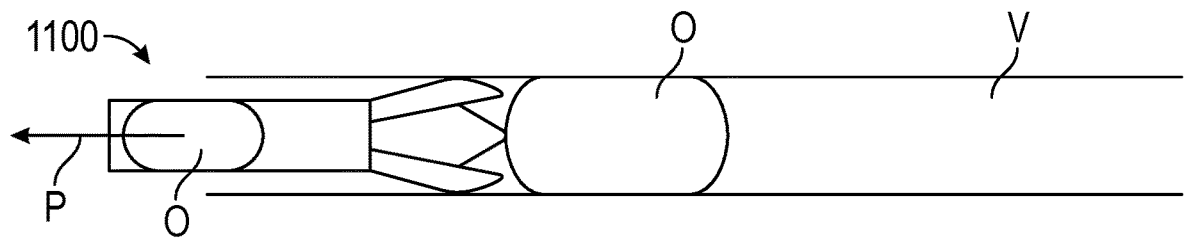

FIGS. 9, 10A, and 10B show a capture structure 900 configured in accordance with several embodiments of the present technology. the system has a funnel scaffolding 901, funnel film 907, an off-axis guidewire lumen 902 throughout the central lumen 908 of the system 900 that returns to the centerline axis of the system through the atraumatic distal tip 903. The system 900 also has a flexible neck 904, an outer sheath 905 and a proximal member 906. The expandable capture structure is deployed by advancing the proximal member 906 or by retracting the outer sheath 905. The expandable capture structure of the system 900 created by one heat shaped filament. The funnel scaffolding is optimally wound and heat set into the funnel shape and flexible neck that is desired and then the scaffolding 901 is covered with a film 907. The funnel is then collapsed by using an outer sheath 905. When collapsed the scaffolding funnel loops that are larger than the inner diameter of the outer sheath 905 are angled distally when collapsed to make repositioning easier.

FIGS. 11A-11E illustrate an example method of use of a treatment system 1100 configured in accordance with the present technology. The treatment system 1100 can comprise an elongated shaft 24, a capture structure 100 carried by the distal portion of the elongated shaft 24, and an orifice 112 extending through the capture structure 100. The capture structure 100 can be advanced distally through the vasculature V until it is positioned proximal to the thrombus O. Once in location, the capture structure 100 can be expanded (FIG. 11B) and negative pressure P can be applied (FIG. 11C) to draw a portion of the thrombus O into the capture structure 100. Once the thrombus O stops advancing into the capture structure 100, the operator can pull a biting wire (as described elsewhere herein) to cause the orifice 112 to collapse and pinch off a portion of thrombus O. The system 1100 digests that portion of the thrombus and an operator can repeat these steps until the thrombus is removed and blood flow within the lumen is increased.

IV. Selected Embodiments of Disrupting Devices

Figure 12:
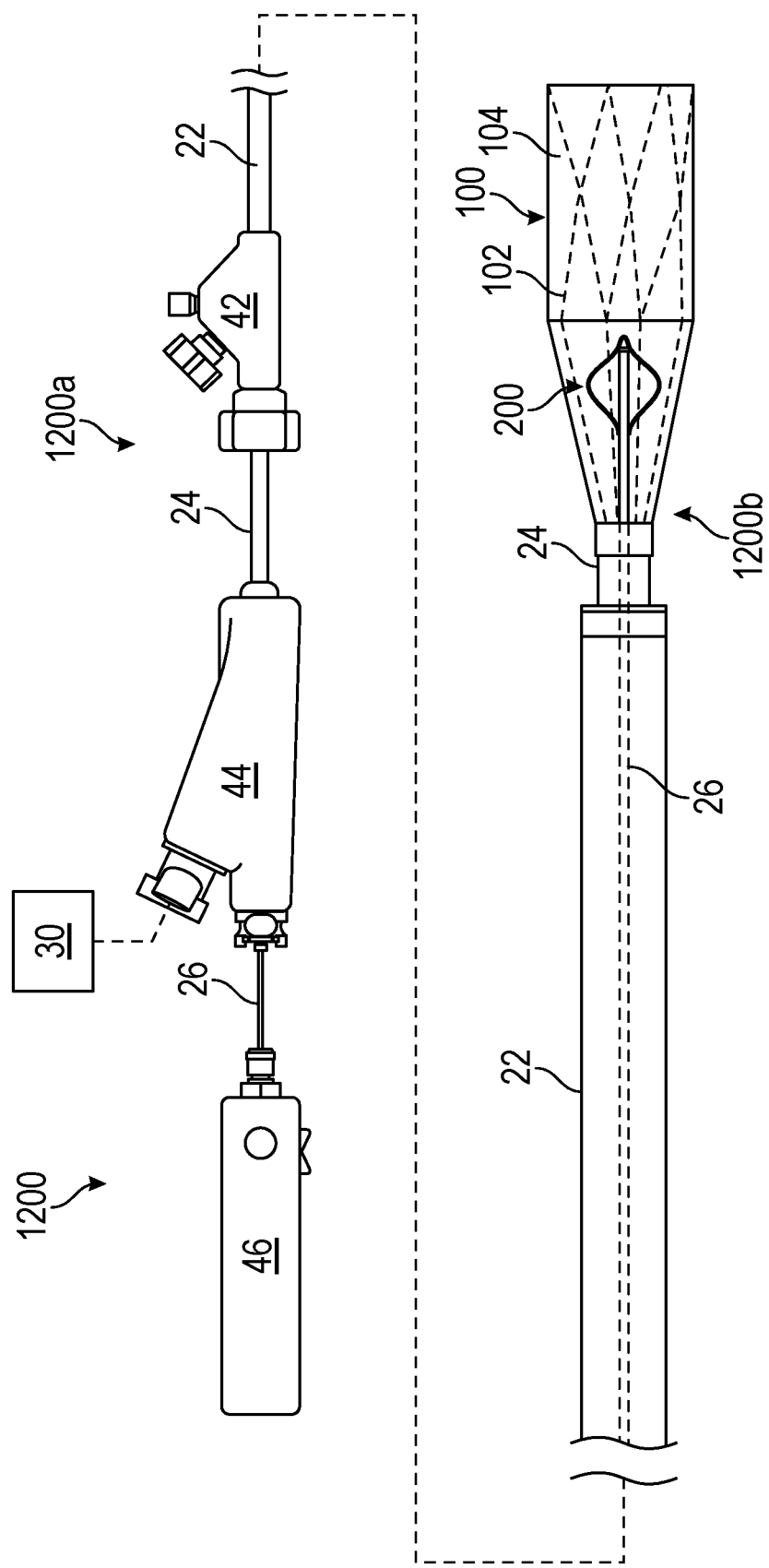
FIG. 12 shows a treatment system configured in accordance with several embodiments of the present technology.

FIG. 12 shows a treatment system 1200 configured in accordance with several embodiments of the present technology. Treatment system 1200 can be generally similar to treatment system 10, except treatment system 1200 further includes a removable disrupting device. "Disrupting device," "disruptor," and "disrupting element" can be used synonymously throughout the present application. The treatment system 1200 can include a proximal portion 1200a configured to be extracorporeally positioned during a procedure and a distal portion 1200b configured to be intravascularly delivered to a treatment site within a blood vessel. The distal portion 1200b can comprise a capture structure 100 and a disruptor 200 removably positioned within an interior region of the capture structure 100. The capture structure 100 and disruptor 200 can be configured to work synergistically to capture and process obstructive material so that the obstructive material can be removed from the patient through the system 1200.

As shown in FIG. 12, the treatment system 1200 can further include a sheath 22, an elongated shaft 24, and an elongated member 26 extending between the proximal and distal portions 1200a, 1200b of the system 1200. The sheath 22 can be a generally tubular member having a proximal end portion, a distal end portion, and a lumen extending therethrough. The elongated shaft 24 can also be a generally tubular member having a proximal end portion, a distal end portion, and a lumen extending therethrough. The elongated member 26 can be a generally tubular member or a solid member having a proximal end portion and a distal end portion. The elongated shaft 24 can be configured to be slidably positioned through the lumen of the sheath 22, and the elongated member 26 can be configured to be slidably positioned within the lumen of the elongated shaft 24.

In some embodiments, the capture structure 100 is carried by a distal end portion 24b of the elongated shaft 24, and both the elongated shaft 24 and the capture structure 100 are configured to be slidably disposed within the sheath's lumen. In those embodiments where the capture structure

100 is self-expanding, the sheath 22 can be configured to radially constrain the capture structure 100 during delivery of the distal portion 10b and release the capture structure 100 to self-expand into the expanded state upon proximal withdrawal of the sheath 22. Moreover, the disruptor 200 can be carried by a distal portion of the elongated member 26.

The proximal portion 1200a of the system 1200 can include a first hub 42, a second hub 44, and a third hub 46 configured to be positioned external to the patient. A distal region of the first hub 42 can be secured to the proximal end portion of the sheath 22, and a proximal region of the first hub 42 can include an opening configured to slidably receive the elongated shaft 24 therethrough. A distal region of the second hub 44 can be secured to the proximal end portion of the elongated shaft 24, and a proximal region of the second hub 44 can include an opening configured to receive the elongated member 26 of the interventional device therethrough. A distal region of the third hub 46 can be secured to the proximal end portion of the elongated member 26.

The first and/or second hubs 42, 44 can include a hemostatic adaptor, a Tuohy Borst adaptor, and/or other suitable connectors, valves and/or sealing devices. For example, in some embodiments, the second hub 44 includes a connector configured to be coupled to a negative pressure source 30 (shown schematically), such as a syringe or a vacuum pump, for applying a negative pressure through a lumen of the elongated shaft 24. Additionally or alternatively, the first hub 42 can include a connector configured to be coupled to a negative pressure source 30 for applying a negative pressure through a lumen of the sheath 22. In some embodiments, the first and/or second hub 42, 44 can include a port configured to be coupled to a fluid source for delivering one or more fluids to the treatment site before, during and/or after the procedure (e.g., contrast, saline, etc.). Additionally or alternatively, the first and/or second hubs 42, 44 can include one or more ports configured to be coupled to a collection chamber for receiving and containing aspirated material from the treatment site.

In some embodiments, the first, second, and/or third hubs 42, 44, 46 include one or more actuators that enable the operator to manipulate the distal portion 1200b of the system 1200. The third hub 46, for example, can comprise a motor coupled to the elongated member 26 and configured to translate, rotate, and/or otherwise agitate the disruptor 200 (via the elongated member 26) when activated. The third hub 26 can include an actuator, such as one or more levers, switches, knobs, buttons, etc., that, when actuated by the operator, turn on the motor and cause the disruptor 200 to begin engaging and/or disrupting obstructive material within the capture structure 100.

FIGS. 13A-30 show and describe examples of disruptors and/or disrupting devices configured for use with any of the treatment systems and/or any of the capture structures disclosed herein. Whether the system is engaging obstructive material by aspiration, mechanical means, or both, there is a possibility that the obstructive material is too large and/or too firm, fibrous, and/or organized to enter into and/or move through the lumen of the elongated shaft and/or aspiration lumen of the system. Accessory tools, such as the disrupting devices of the present technology and others, can be used in conjunction with the capture structure 100 to assist in the withdrawal of the obstructive material via aspiration and/or mechanical means. For example, in some cases, all or a portion of the obstructive material may become immovable or otherwise stuck within the capture structure and/or aspiration lumen. The disrupting devices of the present technology can be used to help release and/or dislodge such blockages of obstructive material. In some embodiments, the disrupting devices can be pre-positioned in the elongated shaft and/or sheath. In some embodiments, the disrupting devices can be integral with the elongated shaft and/or sheath. According to several embodiments, the disrupting devices can be inserted as needed into the elongated shaft and/or sheath. The disrupting devices of the present technology are configured to be advanced into and/or through lodged obstructive material and manipulated by translation, rotation, or both to disrupt lodged obstructive material. Such disruption can be conducted simultaneously with aspiration and/or without aspiration. The disruptor could be used intermittently with aspiration.

The disrupting devices of the present technology can disrupt the obstructive material in a variety of ways. In some embodiments, the disrupting device provides a break-away force to free up stuck obstructive material held in an equilibrium condition. In some embodiments, the disrupting device engages the obstructive material for forward or back translation and/or rotation to free stuck obstructive material held in an equilibrium condition. In some embodiments, the disrupting device breaks a stuck obstructive material into finer pieces or segments that can fit through the sheath lumen without becoming lodged. The breaking of obstructive material can be mechanical disruption (blunt dissection) or it could be slicing. The motion of the disrupting device can be generated by a user applying motion to an elongated member of the disrupting device that extends to an extracorporeal location. In some embodiments, a proximal end portion of the disrupting device extends through a seal that maintains hemostasis and vacuum pressures even during motion of the disrupting device. The motion of the disrupting device can be imparted through a mechanical means, such as a handle with linkages or rack and pinions to cause movement of the disrupting device through the squeeze, push, and/or pull of a handle comprising a housing and an actuator. In these and other embodiments, the motion of the disrupting device could be imparted through an electro-mechanical or pneumatic counsel.

Any of the embodiments of disrupting devices herein can be configured to engage with a guidewire coaxially or as rapid exchange. Any of the disruptors could have atraumatic filiform tips. Any of the disruptors could be configured to dispense contrast fluid through the elongated shaft. Certain embodiments of the disruptors could be used to help deploy and/or maintain the vacuum patency of the expandable capture structure.

In some embodiments, the disrupting device mechanically modulates the negative pressure within the central lumen of the catheter. In some embodiments, the disrupting element mechanically macerates the thrombus as it enters the central lumen. In some embodiments, the disrupting element mechanically engages and pulls the thrombus through the central lumen. In some embodiments, the thrombus is advanced within the central lumen of the distal section through the distal orifice prior to the negative pressure being applied.

Figure 13A:
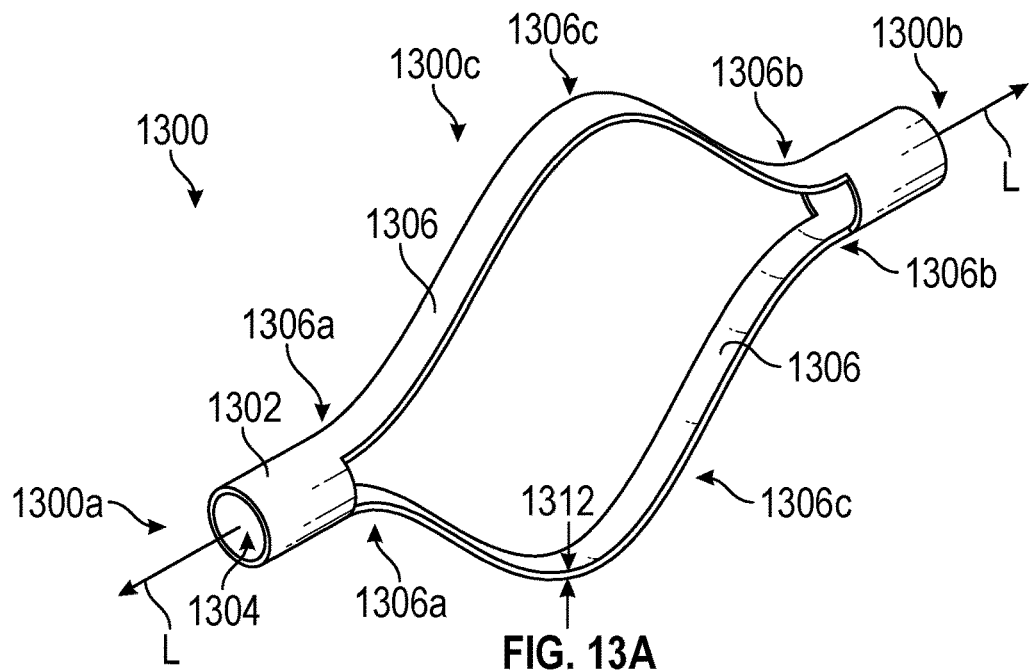
FIGS. 13A-13E are various views of a disrupting element configured in accordance with several embodiments of the present technology.
Figure 13B:
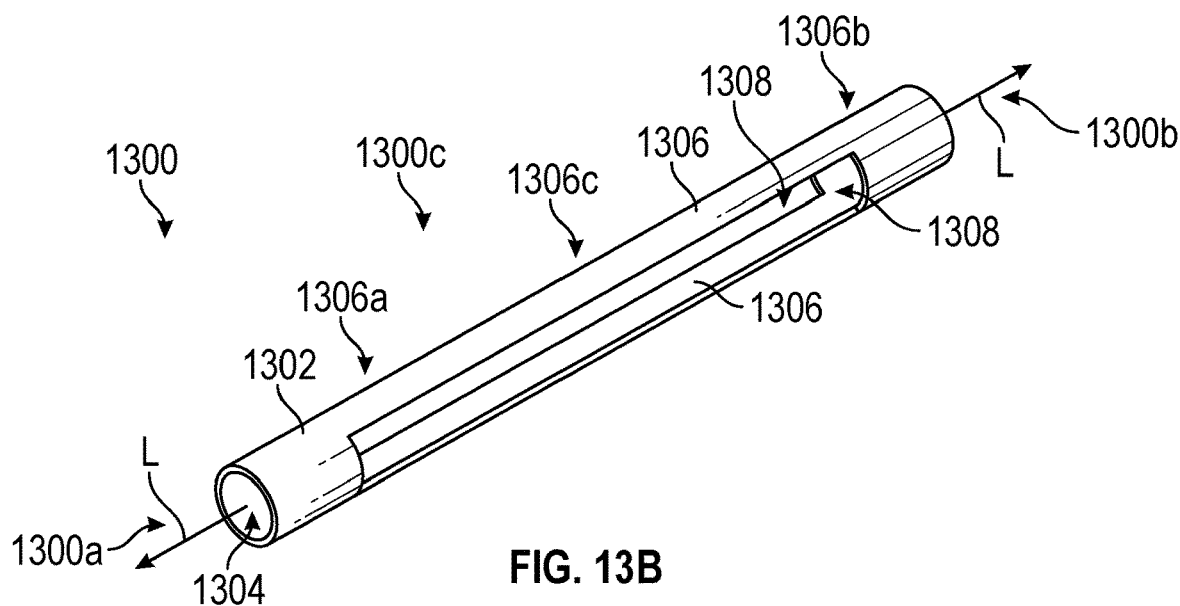
Figure 13C:
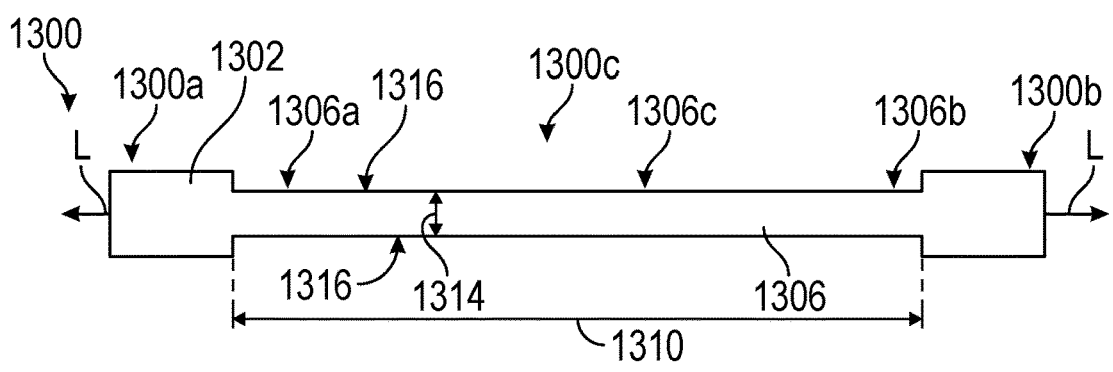

FIGS. 13A-13C depict a disruptor 1300 in accordance with several embodiments of the present technology. FIG. 13A is an isometric view of the disruptor 1300 in an expanded state and FIGS. 13B and 13C are isometric and top views, respectively, of the disruptor 1300 in a collapsed state. As shown in FIG. 13B, in the collapsed state the disruptor 1300 can have a substantially tubular shape. The disruptor 1300 can have a first end portion 1300a, a second end portion 1300b opposite the first end portion 1300a along a longitudinal axis L of the disruptor 1300, an intermediate portion 1300c between the first and second end portions 1300a, 1300b. The disruptor 1300 can have a sidewall 1302 defining a lumen 1304 extending from the first end portion 1300a to the second end portion 1300b. The disruptor 1300 can have a first cross-sectional dimension (e.g., a diameter, a radius, etc.) in the collapsed state and a second cross-sectional dimension in the expanded state. According to various embodiments, the second cross-sectional dimension of one or more portions of the disruptor 1300 can be larger than the first cross-sectional dimension of a corresponding portion of the disruptor 1300. In some embodiments, a maximum cross-sectional dimension of the disruptor 1300 can be less than, greater than, or substantially equivalent to a corresponding cross-sectional dimension of a lumen of an elongated shaft configured to receive the disruptor 1300 for delivery of the disruptor 1300. The disruptor 1300 can be heat set such that the disruptor 1300 is configured to self-expand from the collapsed state to the expanded state.

In some embodiments, for example as shown in FIGS. 13A-13C, the first end portion 1300a and/or the second end portion 1300b of the disruptor 1300 are circumferentially continuous. Additionally or alternatively, the intermediate portion 1300c of the disruptor 1300 can be circumferentially discontinuous. For example, as shown in FIGS. 13A and 13B, the intermediate portion 1300c can comprise one or more struts 1306. In some embodiments, the disruptor 1300 comprises a tube defining one or more openings 1308. For example, the disruptor 1300 can comprise a tube defining two openings 1308 comprising longitudinal slots such that the portions of the sidewall 1302 between the openings 1308 form the longitudinal struts 1306 (see, for example, FIGS. 13A-13C). As described herein, the tube can comprise a metal such as, for example, any superelastic or resilient metal (e.g., nitinol, a cobalt-chromium alloy, etc.).

Each of the struts 1306 can have a first end portion 1306a, a second end portion 1306b opposite the first end portion 1306b along the longitudinal axis L of the disruptor 1300, and an intermediate portion 1306c between the first and second end portions 1306a, 1306b. In the expanded state, one or more of the struts 1306 can extend radially outwardly from the first end portion 1306a to the intermediate portion 1306c and/or radially inwardly from the intermediate portion 1306c to the second end portion 1306b. Accordingly, the intermediate portion 1306c of the strut 1306 can comprise a radial peak and the first and second end portion 1306a, 1306b of the strut 1306 can converge towards the longitudinal axis L of the disruptor 1300.

1011.01 Each of the struts 1306 of the disruptor 1300 can have a length 1310 defined along the longitudinal axis L of the disruptor 1300, a thickness 1312 defined between an abluminal surface of the disruptor 1300 and a luminal surface of the disruptor 1310, and a width 1314 defined as a circumferential distance between two edges 1316 of a strut 1306 of the disruptor 1300. In some embodiments, the length 1310 of one or more of the struts 1306 can be less than an overall length of the disruptor 1300. It may be advantageous for the width 1314 of each of the struts 1306 to be above a predetermined threshold and/or maximized in order to enhance durability of the struts 1306. However, it may also be desirable for a cross-sectional dimension of the disruptor 1300 to be below a predetermined threshold and/or minimized to prevent or limit obstruction of a lumen of an elongated shaft that the disruptor 1300 is positioned within. Accordingly, it may be advantageous for a disruptor 1300 to comprise fewer struts 1306 having larger widths 1314. For example, as shown in FIGS. 13A-13C, the disruptor 1300 can comprise two struts 1306. In these and other embodiments, each strut 1306 can have a width 1314 spanning a circumferential distance of no more than 180 degrees, no more than 150 degrees, no more than 120 degrees, no more than 90 degrees, no more than 60 degrees, no more than 30 degrees, about 170 degrees, about 160 degrees, about 150 degrees, about 140 degrees, about 130 degrees, about 120 degrees, about 110 degrees, about 100 degrees, about 90 degrees, about 80 degrees, about 70 degrees, about 60 degrees, about 50 degrees, about 40 degrees, about 30 degrees, about 20 degrees, about 10 degrees, or about 5 degrees.

In some embodiments, the disruptor 1300 is configured to rotate such that edges 1316 of the struts 1306 engage obstructive material and mechanically disrupt the obstructive material. The edges 1316 of the struts 1306 can be blunt or sharp. When the disruptor 1300 is rotated in a first direction (e.g., clockwise, counterclockwise, etc.) to disrupt obstructive material, a first one of the edges 1316 of each strut 1306 can be a leading edge that contacts the obstructive material before a second one of the edges 1316 of the strut 1306 contacts the obstructive material. In some embodiments, for example when the disruptor 1300 is configured to be rotated in a single direction, only the leading edges 1316 of the struts 1306 are sharpened. Additionally or alternatively, both edges 1316 of the struts 1306 can be sharpened, which may be advantageous if the disruptor 1300 is configured to be rotated in two opposing directions.

Figure 13D:
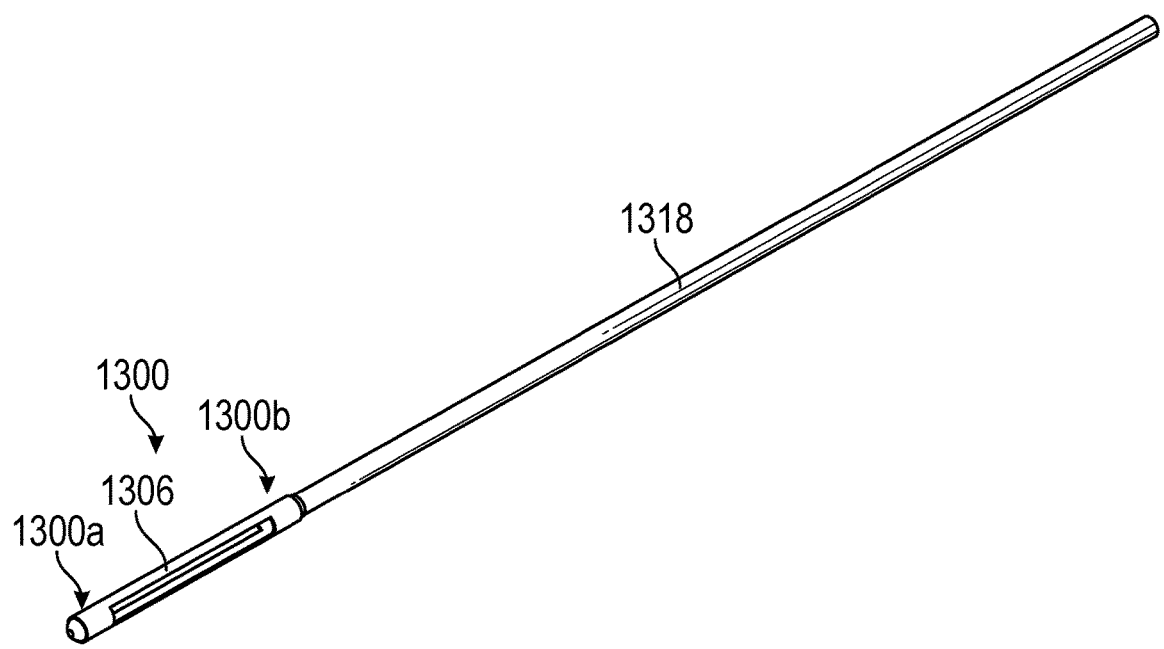
Figure 13E:
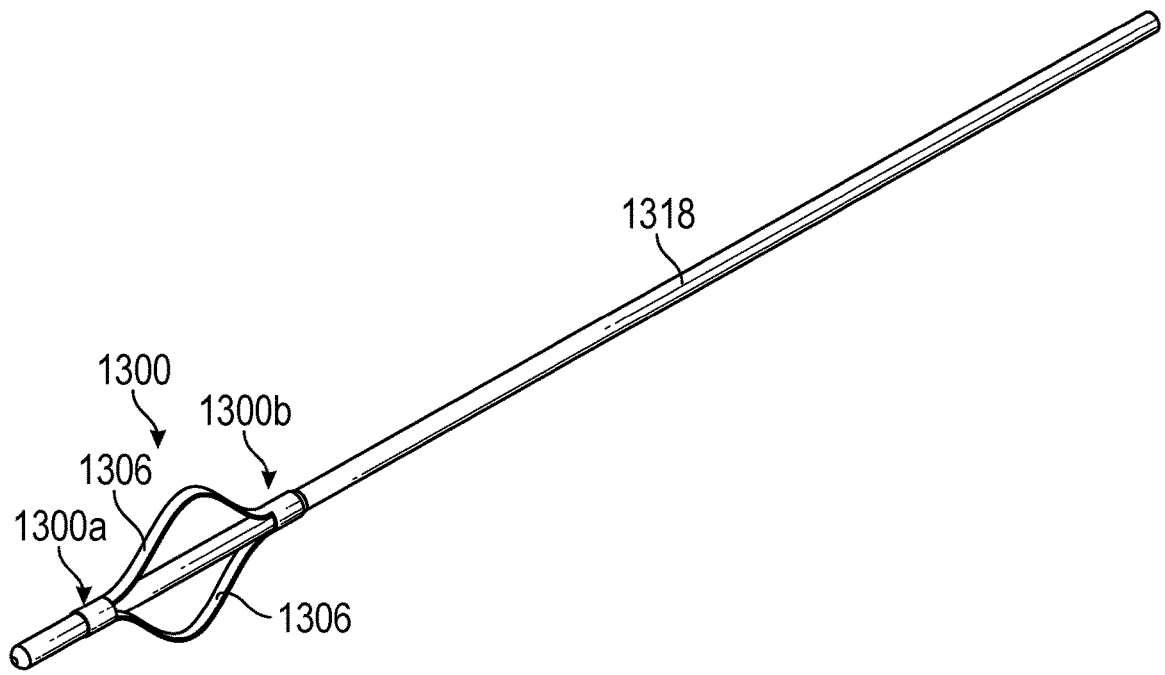

FIGS. 13D and 13E depict the disruptor 1300 of FIGS. 13A-13C in the collapsed configuration and the expanded configuration, respectively. As shown in FIGS. 13D and 13E, the disruptor 1300 can be positioned on, carried by, or otherwise secured to an elongated member 1318. The elongated member 1318 can be similar to any other elongated members disclosed herein (e.g., elongated member 26, etc.). In some embodiments the elongated member 1318 is positioned within the lumen 1304 of the disruptor 1300. The elongated member 1318 can have superelastic and/or shape memory properties. In some embodiments, the elongated member 1318 comprises a wire and/or a hypotube formed from Nitinol or another suitable metal. The elongated member 1318 can have a length between about 50 cm and about 200 cm, between about 60 cm and about 190 cm, between about 70 cm and about 180 cm, between about 80 cm and about 170 cm, between about 90 cm and about 160 cm, between about 100 cm and about 150 cm, between about 110 cm and about 140 cm, between about 120 cm and about 130 cm, less than 50 cm, about 50 cm, about 50 cm, about 60 cm, about 70 cm, about 80 cm, about 90 cm, about 100 cm, about 110 cm, about 120 cm, about 130 cm, about 140 cm, about 150 cm, about 160 cm, about 170 cm, about 180 cm, about 190 cm, about 200 cm, or greater than 200 cm. The elongated member 1318 can have a greatest cross-sectional diameter of between about 0.01 in and about 0.05 in, between about 0.015 in and about 0.045 in, between about 0.02 in and about 0.04 in, between about 0.025 in and about 0.035 in, less than 0.01 in, about 0.01 in, about 0.015 in, about 0.02 in, about 0.025 in, about 0.03 in, about 0.035 in, about 0.04 in, about 0.045 in, about 0.05 in, or greater than 0.05 in. In some embodiments, the elongated member 1318 has an outer diameter substantially equivalent to an inner diameter of a sleeve configured to receive the elongated member 1318 (e.g., elongated shaft 24).

In some embodiments, the first end portion 1300a of the disruptor 1300 is configured to be fixedly secured to the elongated member 1318 while the second end 1300b portion of the disruptor 1300 is configured to be slidably positioned over the elongated member 1318. The second end portion 1300b can be moved over the elongated member 1318 and away from the first end portion 1300a along the longitudinal axis L of the disruptor 1300 such that the disruptor 1300 elongates and radially compresses to assume the collapsed configuration. Conversely, the second end portion 1300b can be moved over the elongated member 1318 and towards the first end portion 1300a along the longitudinal axis L of the disruptor 1300 such that the disruptor 1300 shortens and radially expands to assume the expanded configuration. Additionally or alternatively, the second end portion 1300b of the disruptor 1300 can be configured to be fixedly secured to the elongated member 1318 while the first end 1300a portion of the disruptor 1300 is configured to be slidably positioned over the elongated member 1318 such that movement of the first end portion 1300a relative to the second end portion 1300b causes radial expansion or radial compression of the disruptor 1300. In some embodiments, the first end portion 1300a and/or the second end portion 1300b can be configured to move relative to the elongated member 1318 by a predetermined amount.

Figure 14A:
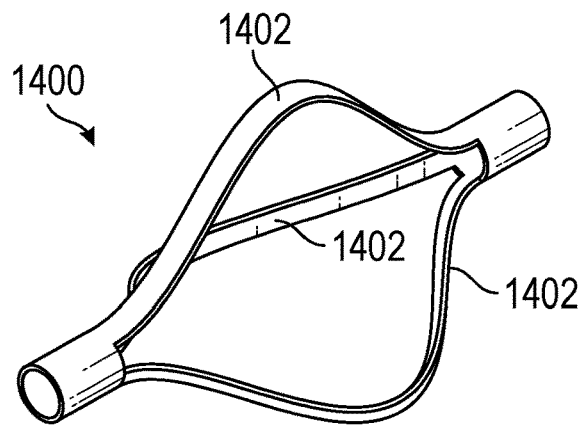
FIGS. 14A-14C are various views of a disrupting element configured in accordance with several embodiments of the present technology.
Figure 14B:
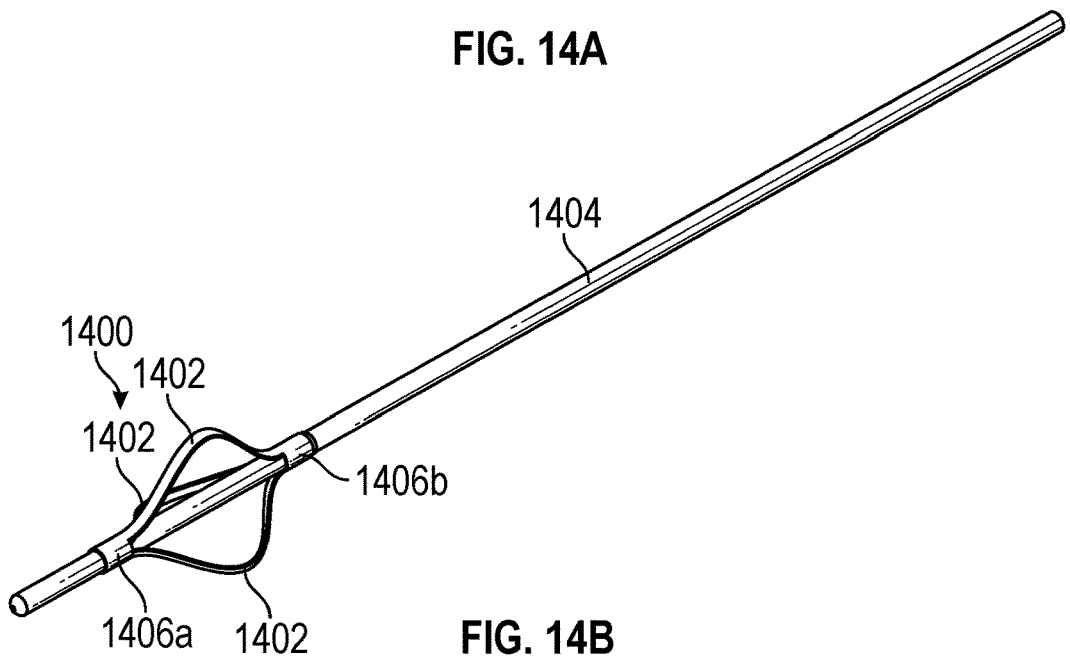
Figure 14C:
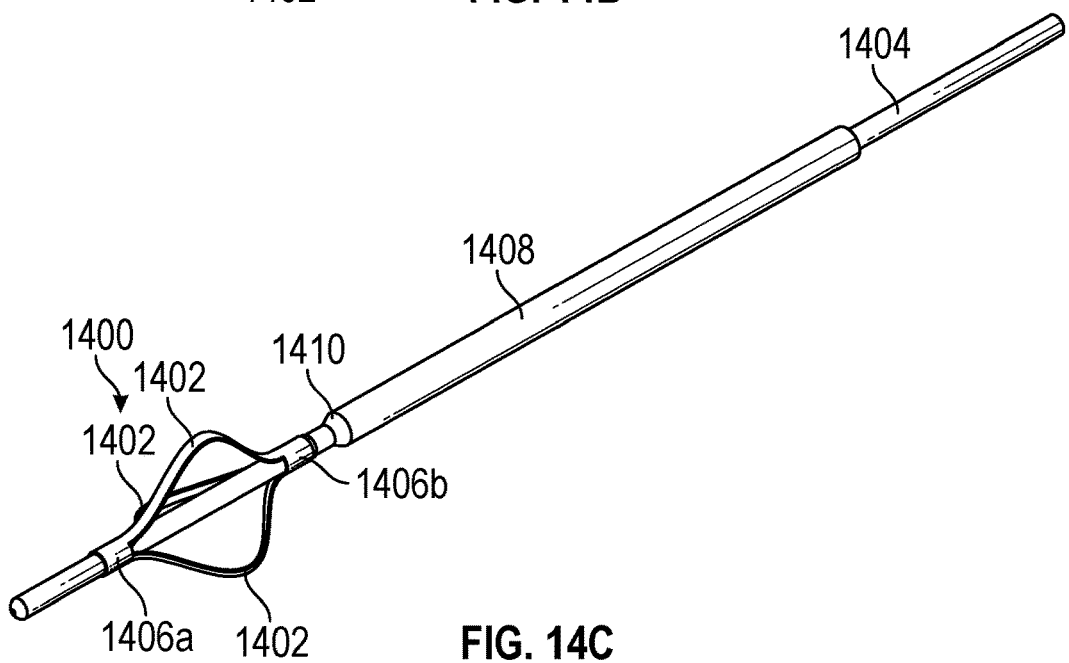

Although FIGS. 13A-13E depict the disruptor 1300 having two struts 1306, other numbers of struts 1306 are possible. As previously described, it may be advantageous for a disruptor to comprise a small number of wide struts. In some embodiments, it may be advantageous for a disruptor to have a specific number of struts and/or to maximize the number of struts. For example, as previously described, a disruptor can be configured to rotate such that edges of struts of the disruptor engage and disrupt obstructive material. In these and other embodiments, a disruptor with more struts has more edges to engage the obstructive material upon each rotation of the disruptor relative to a disruptor with fewer struts. As but one example, FIGS. 14A-14C show a disruptor 1400 having three struts 1402. A disruptor in accordance with the present technology can have one strut, two struts, three struts, four struts, five struts, six struts, seven struts, eight struts, nine struts, ten struts, or more than ten struts.

In some embodiments, the struts 1402 can be evenly distributed about a circumference of the disruptor 1400 such that an angular spacing between a pair of adjacent struts 1402 is substantially the same as angular spacing between one or more other pairs of adjacent struts 1402. For example, adjacent ones of the three struts 1402 shown in FIGS. 14A-14C can be spaced apart by about 120 degrees. In some embodiments, the struts 1402 can be unevenly spaced about a circumference of the disruptor 1400. For example, a first angular spacing between a first pair of adjacent struts 1402 can be different than a second angular spacing between a second pair of adjacent struts 1402.

As shown in FIG. 14B, the disruptor 1400 can be configured to be positioned on, carried by, or otherwise secured to an elongated member 1404. The disruptor 1400 can comprise a proximal collar 1406a and a distal collar 1406b, which can be movable relative to one another to transform the disruptor from a collapsed state to an expanded state. As shown in FIG. 14C, a system in accordance with several embodiments of the present technology can comprise an elongated shaft 1408 configured to be positioned over the elongated member 1404 and/or the disruptor 1400. The elongated shaft 1408 can have a generally tubular shape, and/or the elongated shaft 1408 can comprise one or more suitable metals or polymers, for example, polyimide. In some embodiments, the elongated shaft 1408 can have one or more flexibility-enhancing cuts.

In some embodiments, the elongated shaft 1408 can be configured to prevent or limit accumulation of obstructive material within a lumen of the elongated shaft 1408, which could hinder aspiration of the obstructive material. For example, as shown in FIG. 14C, the elongated shaft 1408 can comprise a cutting portion 1410 located at a distal end of the elongated shaft 1408. The cutting portion 1410 can comprise a sharpened edge, a coring edge, a bevel edge, etc.

Figure 15A:
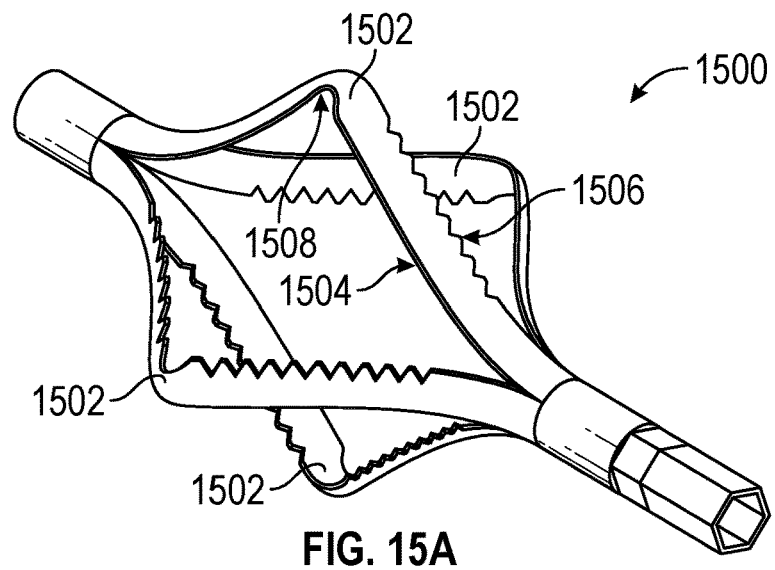
FIGS. 15A-15C are various views of a disrupting element configured in accordance with several embodiments of the present technology.
Figure 15B:
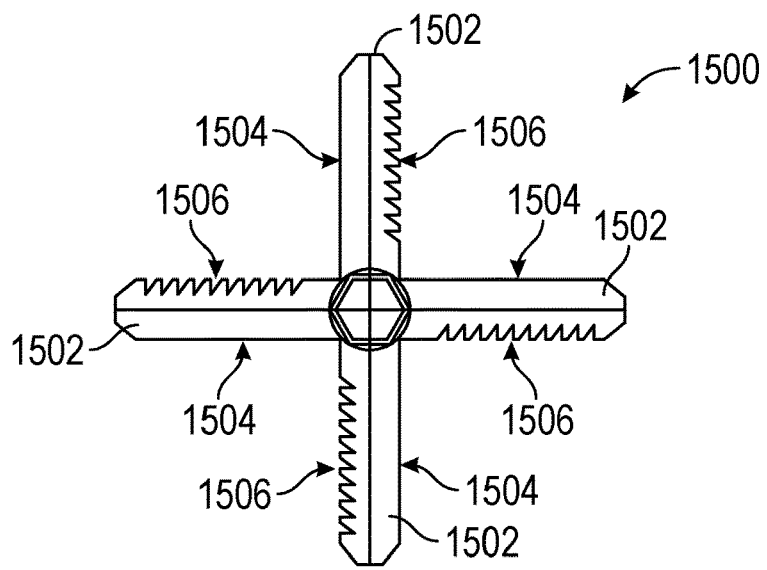
Figure 15C:
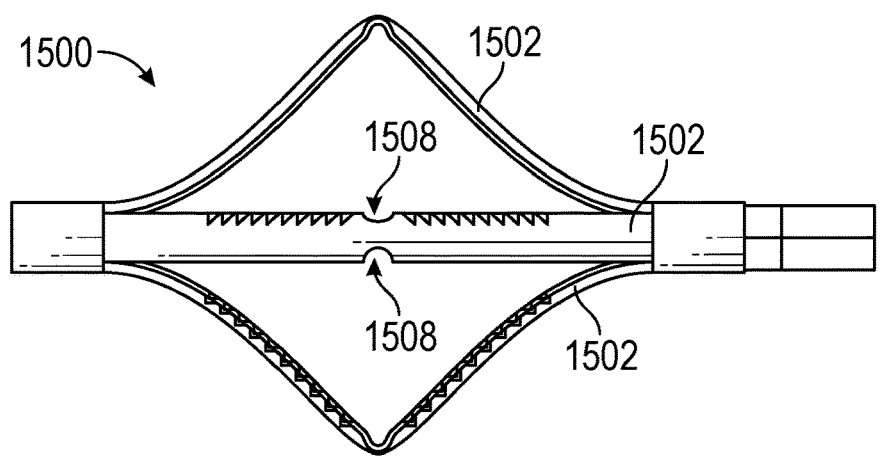

FIGS. 15A-15C show isometric, end, and side views, respectively, of a disruptor 1500 in accordance with several embodiments of the present technology. The disruptor 1500 can have one or more struts 1502, for example four struts 1502 as shown in FIGS. 15A-15C. Each strut 1502 can comprise a first edge 1504 and a second edge 1506. The first edge 1504 and/or the second edge 1506 can comprise one or more features configured to facilitate disruption of obstructive material engaged by the struts 1502. For example, as shown in FIGS. 15A-15C, the second edge 1506 can be serrated. In these and other embodiments, the second edge 1506 can be a leading edge (e.g., during a rotation of the disruptor 1500, the second edge 1506 can contact the obstructive material before the first edge 1506 contacts the obstructive material). Although not shown in FIGS. 15A-15C, in some embodiments the first edge 1504 is also serrated and/or sharpened. Such configurations may be advantageous for a disruptor 1500 configured to be rotated in two opposing directions.

In some embodiments, the struts 1502 can comprise one or more features configured to facilitate collapse and/or expansion of the disruptor 1500. For example, as shown in FIGS. 15A-15C, the struts 1502 can comprise one or more weakened portions 1508 that facilitate elongation of the struts 1502 as the disruptor 1500 transforms to the collapsed state. The weakened portion 1508 can comprise a recess, an opening, an aperture, a slot, a thinned region, etc.

Figure 16A:
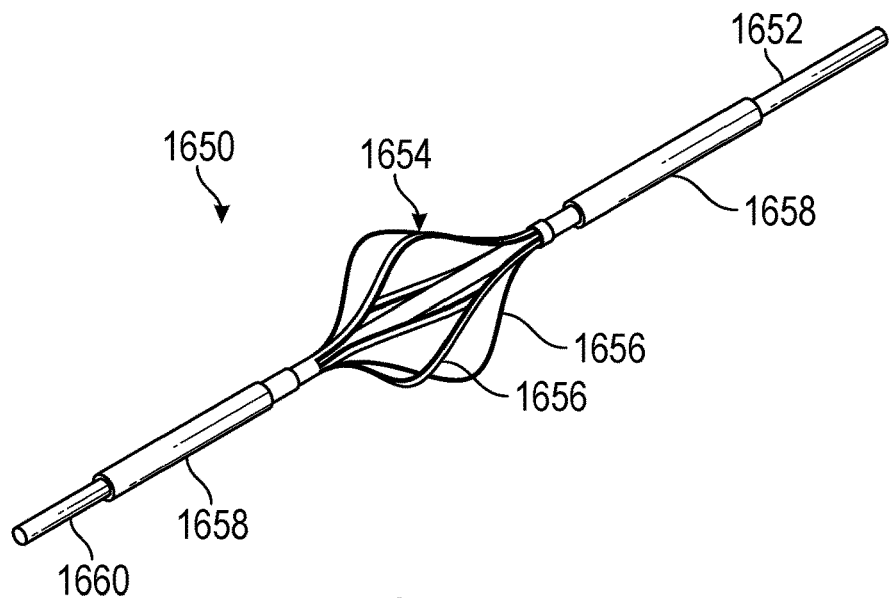
FIGS. 16A-16C are various views of a disrupting element configured in accordance with several embodiments of the present technology.
Figure 16B:
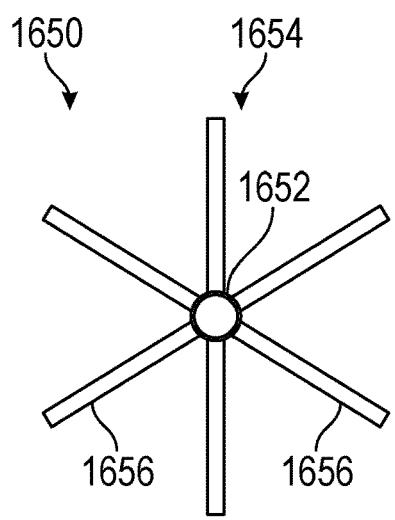
Figure 16C:
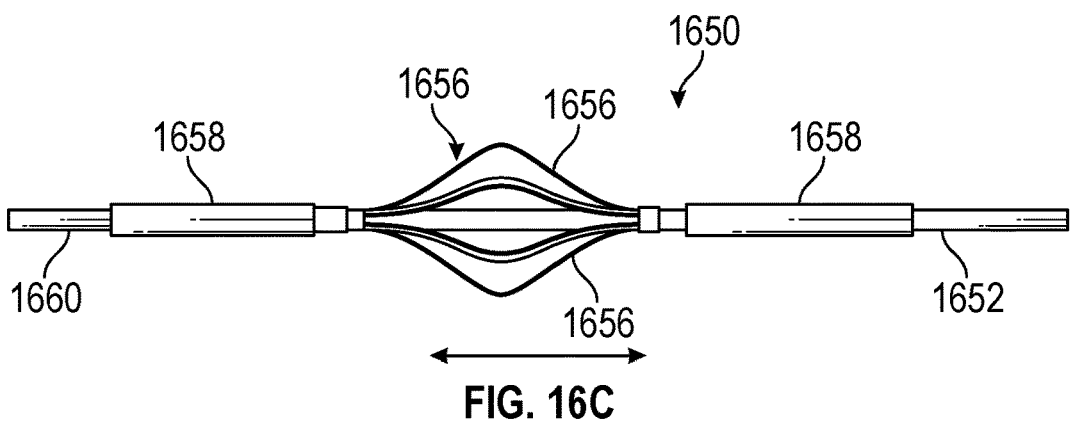

FIGS. 16A-16C show a disruptor 1650 comprising an elongated member 1652 and a basket 1654 carried by the distal end of the elongated member 1652. The elongated member 1652 can be a tube defining a lumen therethrough or can be a solid member. The basket 1654 may comprise a plurality of expandable struts 1656 (only a few labeled). In some embodiments, the basket 1654 can have an expanded state diameter smaller than the elongated shaft 24 inner diameter (the main lumen and/or a sub-lumen) or even larger since it can actively or passively transform its profile. In some embodiments, such as that shown in FIGS. 16A-16C, the basket 1654 is formed of a tube. The tube may comprise a metal such as, for example, any superelastic or resilient metal (e.g., nitinol, a cobalt-chromium alloy, etc.). In some embodiments the tube has a length of about 0.5 inches. The tube may comprise a plurality of longitudinal slots that create the struts therebetween. The distal and proximal end portions of the tube can remain continuous around their circumference, for example to attach to opposing collars. The tube can be heat set such that the tube self-expands to form a basket when released from a constrained state.

The basket 1654 structure has advantages over the hook embodiments as it has forward and rear edges that will not catch on the elongated shaft 24 (or any constraining structure), while still providing a disrupting and or cutting set of struts 1654. The basket 1654 could be fixed at its distal end while its proximal end is left to slide over the elongated member 24. In this way it could be elongated and compressed for insertion into the elongated shaft 24 lumen and expand to its intended profile in the lumen or in the expanded structure of the elongated shaft 24 at the distal end. In this particular embodiment shown in the figure, the basket 1654 is slidable on the elongated member 1652 in both directions and maintained between two crimped bushings 1658 that govern a finite zone of its sliding. This would allow the basket 1654 to compress as needed while introducing into the elongated shaft 24 or retracting it out of the elongated shaft 24. This embodiment also shows an elongated tip 1660 of about 1 cm length that would be more flexible than the elongated member 1652 to provide an atraumatic, filiform distal end to help guide the device around the clot prior to its retraction and clot agitation.

FIGS. 17A-17C show a disruptor 1700 configured in accordance with several embodiments of the present technology. The disruptor 1700 comprises an elongated shaft 1702 having a hook 1704 at its distal end. The shaft 1702 can be long enough to extend the length of the elongated shaft 22 and/or 24 and the capture structure (such as capture structure 100) and still have enough extra length at the proximal end for holding and imparting motion. The elongated shaft 1702 can be optimized for translation and or rotation but simultaneously minimized to occupy minimal space in the sheath. In some embodiments, the shaft 1702 comprises a nitinol wire having a diameter of from about 0.020 inches to about 0.040 inches. The distal-most tip of the disruptor 1700 can comprise a hook 1704 that extends back proximally. The hook 1704 can have a smaller cross-sectional dimension than the smallest inner diameter of the sheath. The disruptor 1700 can be used to pass through and retract clot material, and in some cases can be rotated to disrupt clot material. In some embodiments, the hook 1704 bends back beyond 180 degrees to reduce the chances of the hook 1704 catching on a portion of an inner surface of the sheath or proximal seal.

FIGS. 18A-18C show a disruptor 1800 configured in accordance with several embodiments of the present technology. The disruptor 1800 includes a shaft 1802 and a plurality of hooks 1804 at the end of the shaft 1802. The hooks 1804 can be arranged in an annular array, similar to a grapple hook. Such an arrangement beneficially provides more surface area for engagement and in more directions, and less rotational direction dependency on engagement.

Figures 19A, 19B, 19C:
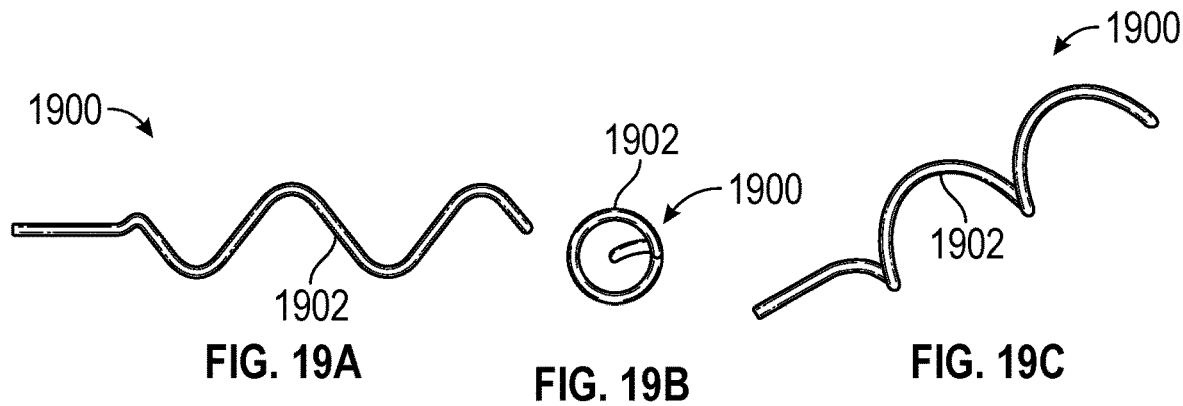
FIGS. 19A-19C are various views of a disrupting element configured in accordance with several embodiments of the present technology.

FIGS. 19A-19C show a disruptor 1900 configured in accordance with several embodiments of the present technology. The disruptor 1900 can comprise an elongated shaft 1902 in the form of a coil. The disruptor 1900 can be configured such that its maximum cross-sectional dimension is approximately the inner diameter of the sheath. Such a configuration can be beneficial for stripping lodged clot off the inner diameter of the sheath lumen. In some embodiments, the elongated shaft 1902 can be rotated about its longitudinal axis to bore into and grab a clot, or to release from the clot in a screw-like fashion. As shown in the end view of FIG. 19B, the projection of the coil can be a hoop with relatively large cross section for engagement. In some embodiments, the loops of the coil can be configured to radially constrict the clot.

Figures 20A, 20B:
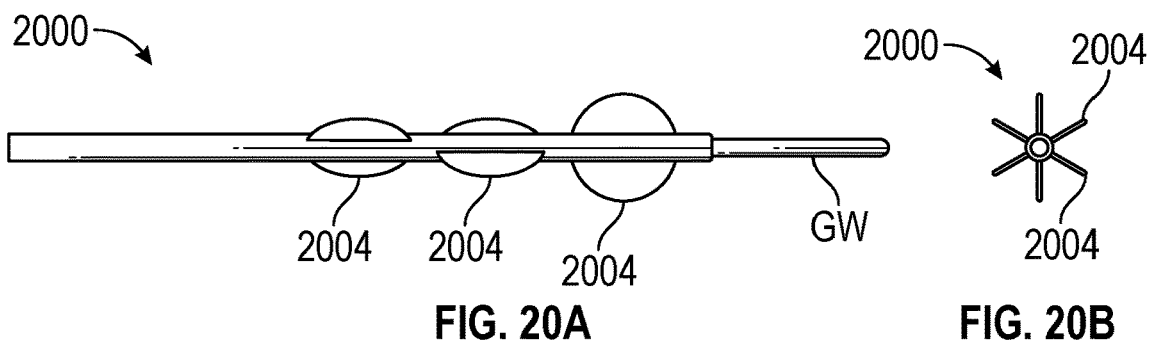
FIGS. 20A-20C are various views of a disrupting element configured in accordance with several embodiments of the present technology.
Figure 20C:
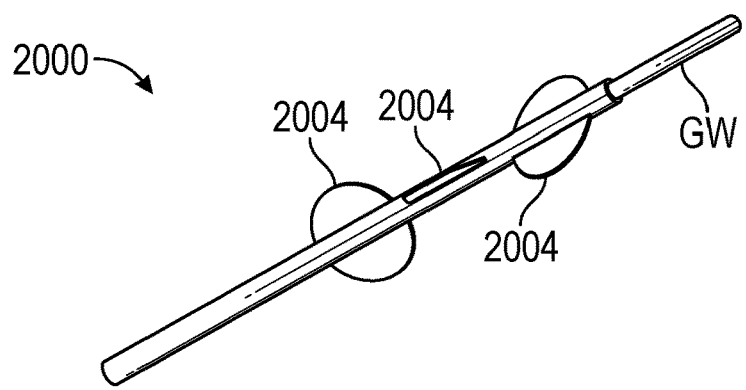

FIGS. 20A-20C show a disruptor 2000 comprising an elongated shaft 2002 and a plurality of curved fins 2004 spaced apart along a distal portion of the shaft 2002. The shaft 2002 can be a solid rod or have a lumen therethrough. In the illustrated embodiment, for example, the shaft 2002 is tubular member defining a lumen and is configured to slidably receive a guidewire GW therethrough. Each of the fins 2004 can have a curved radial surface that presents an atraumatic surface with a low likelihood of catching on the sheath. The shape of the fins 2004 can also be configured to facilitate passage into or through the clot. In some embodiments, all or a portion of the edges of one, some, or all of the fins 2004 are blunt, and in some embodiments, all or a portion of the edges of one, some, or all of the fins 2004 are sharpened. According to several embodiments, a distal-facing edge and/or surface 2008 of one, some, or all of the fins 2004 is a cutting element. In some embodiments, a proximal-facing edge and/or surface 2008 of one, some, or all of the fins 2004 is a cutting element. The individual fins 2004 can have a thickness of from about 0.010 inches to about 0.005 inches and may have a crossing profile just smaller than the inner diameter of the sheath.

In use, the fins 2004 can be translated into or out of a clot via axial movement of the shaft 2002 to provide blunt or cutting clot disruption. In some embodiments, the shaft 2002 and/or fins 2004 can be rotated to bluntly dissect the clot material. Each of the fins 2004 can extend from a different circumferential location about the shaft 2002 such that cumulatively the edges of the fins 2004 are disposed in an annular array about a circumference of the disruptor 2000, as shown in FIG. 20B. In some embodiments, the fins 2004 are positioned at substantially the same longitudinal location on the shaft 2002 but in different orientations, thereby achieving the profile shown in FIG. 20B but without being spaced apart longitudinally along the elongated shaft 2002. The foregoing embodiment reduces a section of maximum material in a discrete location relative to the sheath. This allows an array but minimizes a mechanical "pinch" point that could impede aspiration or physical clot passage.

Figure 21A:
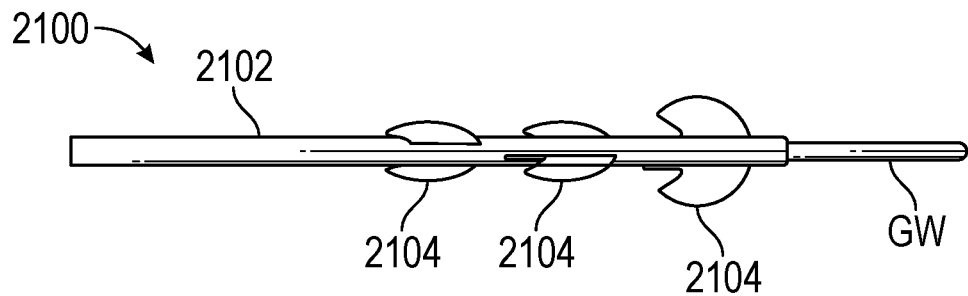
FIGS. 21A-21C are various views of a disrupting element configured in accordance with several embodiments of the present technology.
Figure 21B:
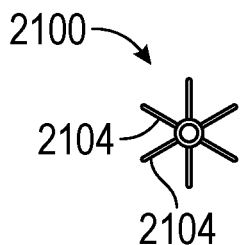
Figure 21C:
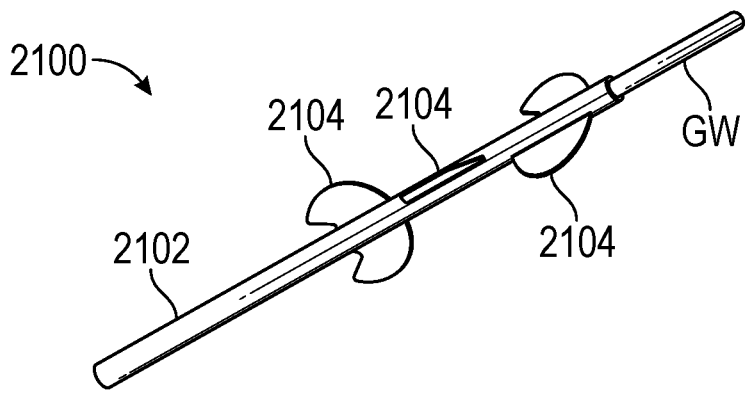

FIGS. 21A-21C show a disruptor 2100 comprising an elongated shaft 2102 and a plurality of curved fins 2104 spaced apart along the shaft 2102. The shaft 2102 can be a solid rod or have a lumen therethrough. In some embodiments, for example, the shaft 2102 defines a lumen and is configured to slidably receive a guidewire GW therethrough. The curvature of the fins 2104 creates an atraumatic surface with a low likelihood of catching on the sheath. The shape of the fins 2104 can also be configured to facilitate passage into or through the clot. In contrast to the fins 1604 of disruptor 1600, the fins 2100 have an arched or curved shape. In some embodiments, all or a portion of the edges of one, some, or all of the fins 2104 are blunt, and in some embodiments, all or a portion of the edges of one, some, or all of the fins 2104 are sharpened. According to several embodiments, a distal-facing edge and/or surface 2108 of one, some, or all of the fins 2104 is a cutting element. In some embodiments, a proximal-facing edge and/or surface 2108 of one, some, or all of the fins 2104 is a cutting element. The individual fins 2104 can have a thickness of from about 0.010 inches to about 0.005 inches and may have a crossing profile just smaller than the inner diameter of the sheath.

In use, the fins 2104 can be translated into or out of a clot to provide blunt or cutting clot disruption. In some embodiments, the shaft 2102 and/or fins 2104 can be rotated to bluntly dissect the clot material. The orientation of the fins 2104 relative to the shaft 2102 can be offset from one another such that cumulatively the edges of the fins 2104 are spaced apart about a circumference of the disruptor 2100, as shown in FIG. 21B. In some embodiments, the fins 2104 are positioned at substantially the same longitudinal location on the shaft 2102 but in different orientations, thereby achieving the profile shown in FIG. 21B but without being spaced apart longitudinally along the elongated shaft 2102. The foregoing embodiment reduces a section of maximum material in a discrete location relative to the sheath. This allows an array but minimizes a mechanical "pinch" point that could impede aspiration or physical clot passage.

Figure 22A:
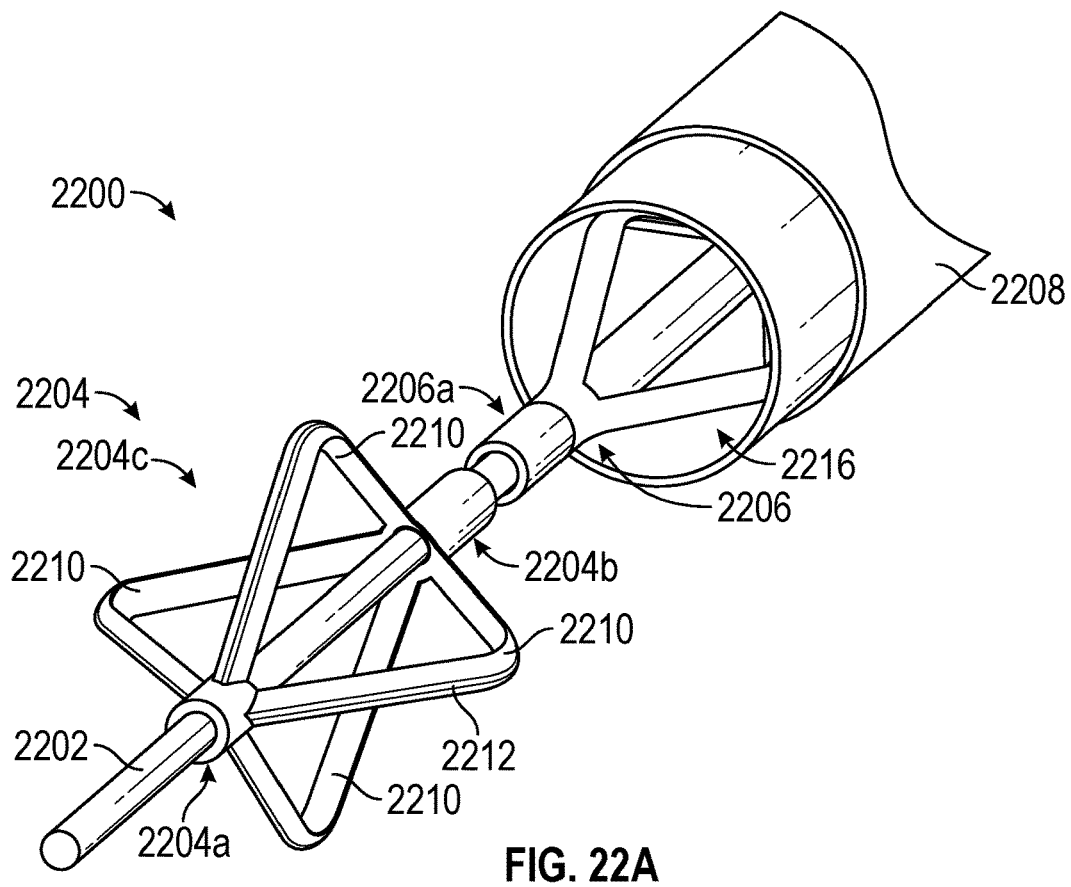
FIGS. 22A and 22B are various views of a disrupting element configured in accordance with several embodiments of the present technology.
Figure 22B:
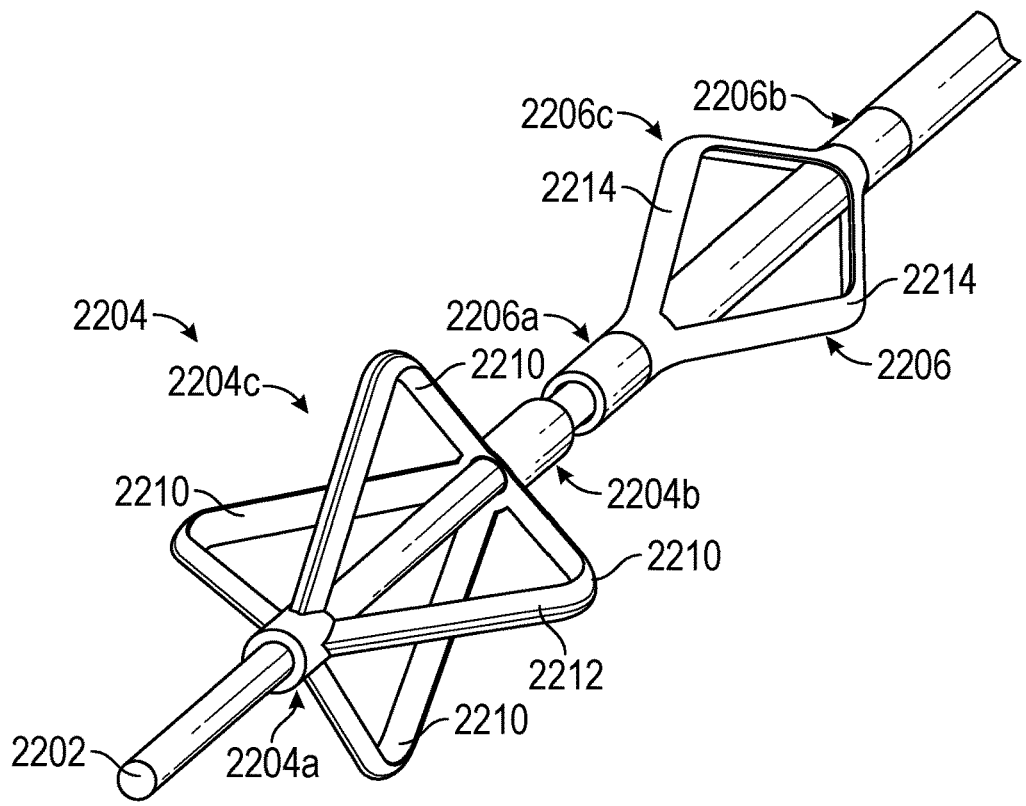

In any of the embodiments described herein, a system in accordance with the present technology can include a centering element configured to facilitate alignment of an elongated member carrying a disruptor with a lumen of an elongated shaft configured to receive the elongated member and/or precise and accurate positioning of the disruptor within a distal housing. For example, FIG. 22A depicts a system 2200 comprising an elongated member 2202, a disruptor 2204 carried by the elongated member 2202, a centering element 2206 carried by the elongated member 2202, and an elongated shaft 2208. FIG. 22B depicts the system 2200 without the elongated shaft 2208. As shown in FIGS. 22A and 22B, the disruptor 2204 can have a first end portion 2204a, a second end portion 2204b, and an intermediate portion 2204c. The first and second end portions 2204a, 2204b can be circumferentially continuous while the intermediate portion 2204c is circumferentially discontinuous and comprises a plurality of struts 2210. For example, as shown in FIGS. 22A and 22B, the intermediate portion 2204c of the disruptor 2204 can comprise four struts 2210. In some embodiments, one or more of the struts 2210 can include a cutting feature 2212 (e.g., a blade, a protrusion, etc.) configured to facilitate disruption of the obstructive material. The disruptor 2204 and/or any portion thereof can be similar to any of the disruptors disclosed herein. For example, the disruptor 2204 can comprise a laser cut tube.

In some embodiments, for example as shown in FIGS. 22A and 22B, the centering element 2206 comprises a first end portion 2206a, a second end portion 2206b opposite the first end portion 2206a, and an intermediate portion 2206c between the first and second end portions 2206a, 2206b. The first and second end portions 2206a, 2206b can be circumferentially continuous while the intermediate portion 2206c is circumferentially discontinuous and comprises a plurality of struts 2214. Additionally or alternatively, the intermediate portion 2206c can be circumferentially continuous. A cross-sectional dimension of the centering element 2206 at the intermediate portion 2206c can be greater than a cross-sectional dimension of the centering element 2206 at the first end portion 2206a and/or the second end portion 2206b. In some embodiments, a maximum cross-sectional dimension of the centering element 2206 substantially corresponds to, is slightly less than, or is slightly more than a cross-sectional dimension of a lumen 2216 of the elongated shaft 2208. Accordingly, when the elongated member 2202 carrying the centering element 2206 is positioned within the lumen 2216 of the elongated shaft 2208, the centering element 2206 can contact wall of the elongated shaft 2208, either continuously or intermittently, such that the elongated member 2202 is substantially centered within the lumen 2216.

In certain cases where the obstructive material is harder and/or more difficult to separate, it may be beneficial to utilize a disrupting device configured to shave the obstructive material. Thrombus, for example, can undergo several phases of maturation in which the initial fibrin mesh is infiltrated by inflammatory and mesenchymal cells that gradually lead to a thickening of extant fibrin fibers or replacement with other structural proteins, including collagen. Such remodeling and replacement of structural constituents within a thrombus alters its biomechanical properties and renders certain disruption methods less effective (as compared to these same methods on softer and/or less organized clot). For instance, the disrupting device shown in FIGS. 13A-13E may be less effective when attempting to break apart more organized and/or mature clot material, as the rotational force of the arms may not be sufficient to break apart and/or separate the clot material. As a result, the clot material may simply rotate with the arms (without breaking up) and little (if any) clot material is removed through the aspiration lumen.

Several disrupting devices of the present technology address the foregoing challenges by providing an opposing force to the rotational and/or axial motion of the disrupting elements, thereby trapping the obstructive material and enabling the disrupting elements to apply a greater cutting and/or separation force to the obstructive material. FIG. 23, for example, shows such a disrupting device 2300. The disrupting device 2300 comprises a supporting element 2302 and a disrupting element 2304 positioned within a lumen of the supporting element 2302. In some embodiments, the disrupting element 2304 is slidably positioned within the supporting element 2302 such that the disrupting element 2304 can move axially relative to the supporting element 2302, and in some cases the disrupting element 2304 can be completely removed from the lumen of the supporting element 2302. The lumen of the supporting element 2302, for example, can be configured to receive other interventional tools therethrough, such as other types of disruptors and/or disrupting devices.

The supporting element 2302 can comprise a tubular portion 2306 and an open distal end portion 2308 along which the sidewall extends less than 360 degrees, thereby exposing lateral supporting edges 2310. The supporting edges 2310 can be blunt or sharpened. In some embodiments, the supporting element 2302 is a separate piece that is coupled to a distal end of an elongated shaft, such as elongated shaft 24 and/or an aspiration catheter. In some embodiments, the supporting element 2302 is integral with an elongated shaft, such as elongated shaft 24 and/or an aspiration catheter. In several of such embodiments, the elongated shaft and supporting element 2302 can be formed of a hypotube. The hypotube can be laser cut at the distal end to form the open distal end portion 2308. According to several embodiments, the hypotube can also have one or more circumferential slits and/or cuts along the portion of its length coinciding with all or a portion of the supporting element 2302 to increase the flexibility of the supporting element 2302. In any case, the lumen of the supporting element 2302 can be configured to be fluidly coupled to a negative pressure source. In some embodiments, the supporting element 2302 comprises a separate shaft slidably disposed within the elongated shaft 24 and/or sheath.

As shown in FIG. 23, the disrupting element 2304 can comprise an elongated shaft 2311 defining a lumen therethrough 2312. The disrupting element 2304 can have an opening 2314 at its distal end portion that faces away from a longitudinal axis of the device in a radial direction. The opening 2314 can be defined by a surface 2318, at least a portion of which comprises a disrupting edge 2316 having one or more features configured to penetrate, cut, or otherwise disrupt obstructive material. For example, in some embodiments the disrupting edge 2316 can be sharpened and/or serrated. In several embodiments, such as that shown in FIG. 23, the disrupting edge 2316 extends along only a portion of the surface 2318 defining the opening 2314. In some embodiments, the disrupting edge 2316 extends along the entire surface 2318. In some embodiments, the disrupting element 2304 has a proximal end portion configured to be coupled to a negative pressure source to draw captured obstructive material towards and through the opening 2314. In some embodiments, one or both of the supporting element 2302 or disrupting element 2304 is not configured to be fluidly coupled to a negative pressure source.

As shown schematically in FIGS. 24A and 24B, the disrupting element 2304 can be configured to rotate relative to the supporting element 2302, thereby bringing the disrupting surface 2316 towards a supporting edge 2310 of the supporting element 2302. In so doing, obstructive material becomes trapped between the disrupting edge 2316 and the supporting edge 2310 such that the supporting edge 2310 provides resistance to rotation of the obstructive material with the disrupting edge 2316 and enables the disrupting edge 2316 to cut through the obstructive material. In some embodiments, both the supporting edge 2310 and disrupting edge 2316 are configured to cut and/or penetrate obstructive material. The separated portions of the obstructive material can then be drawn through the lumen 2312 of the disrupting element 2304 and removed from the body.

Figure 25:
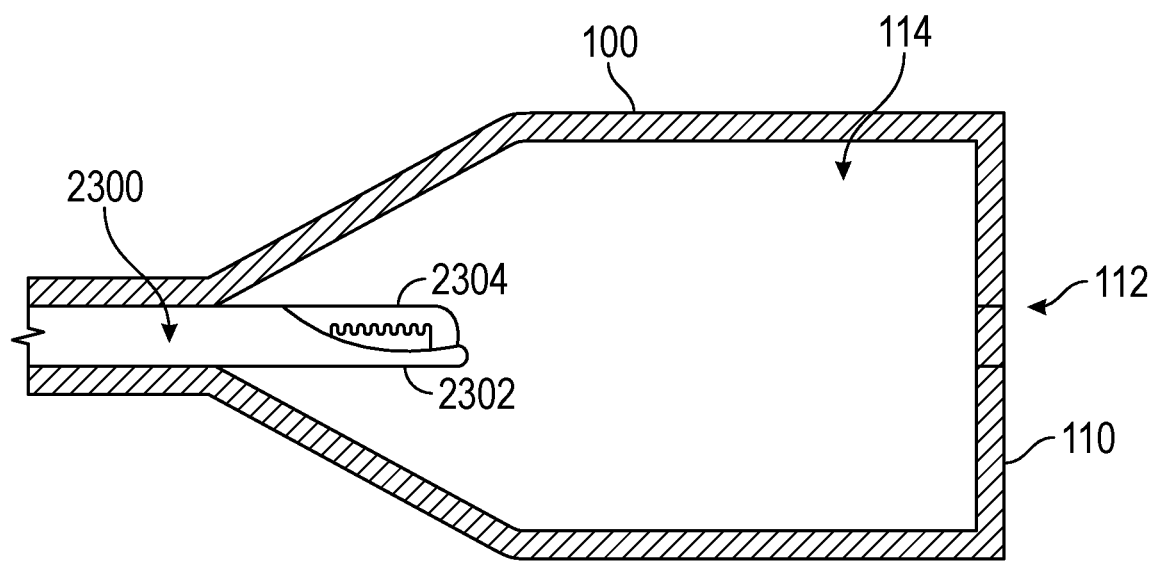

FIG. 25 shows a distal end portion of a treatment system configured in accordance with several embodiments of the present technology, showing the disrupting device 2300 positioned within the capture structure 100. The supporting element 2302 can be positioned within the interior region 114 of the capture structure 100 such that the open distal end region can fully access capture clot (not shown) within the capture structure 100.

Figure 26:
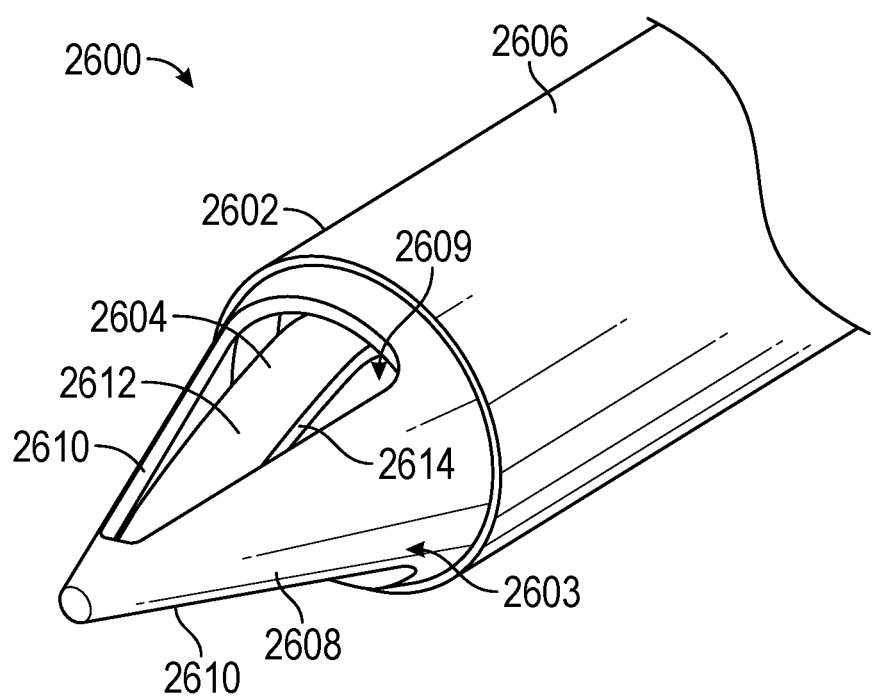
FIGS. 26 and 27 show a disrupting device configured in accordance with several embodiments of the present technology.

FIG. 26 shows a distal portion of a disrupting device 2600 configured in accordance with several embodiments of the present technology. The disrupting device 2600 can comprise a supporting element 2602 and a disrupting element 2604 positioned within a lumen of the supporting element 2602. In some embodiments, the disrupting element 2604 is slidably positioned within the supporting element 2602 such that the disrupting element 2604 can move axially relative to the supporting element 2602, and in some cases the disrupting element 2604 can be completely removed from the lumen of the supporting element 2602. The lumen of the supporting element 2602, for example, can be configured to receive other interventional tools therethrough, such as other types of disruptors and/or disrupting devices.

The supporting element 2602 can comprise a tubular portion 2606 and a conical distal end portion 2603 comprising a plurality of arms 2608 and openings 2609 between the arms 2608. Each of the arms 2608 can extend distally and radially inwardly from the tubular portion 2606. In some embodiments, the distal end portion 2603 can have other shapes and/or may not taper distally. Each of the arms 2608 can have supporting edges 2610 which can be blunt or sharpened.

The supporting element 2602 can be arranged in a variety of ways relative to an elongated shaft (e.g., elongated shaft 24, aspiration catheter, etc.). For example, the supporting element 2602 may comprise only the distal end portion 2603, which may be coupled to the distal end portion of an elongated shaft and/or aspiration catheter. In some embodiments, the supporting element 2602 comprises both the tubular portion 2606 and the distal end portion 2603, but is still a separate piece from the elongated shaft. According to several aspects of the present technology, the tubular portion 2606 extends all the way proximally to the user (i.e., the tubular portion 2606 comprises the elongated shaft), and is slidably disposed within an aspiration catheter (such as elongated shaft 24). In some embodiments, the lumen of the tubular portion 2606 is configured to be coupled to a negative pressure source.

As shown in FIG. 26, the disrupting element 2604 can comprise a plurality of arms 2612 (only one shown) and an elongated member (not visible) extending proximally to the user. The elongated member can be a solid elongated member, or may be an elongated shaft. The arms 2612 can have disrupting edges 2614, at least a portion of which comprises one or more features configured to penetrate, cut, or otherwise disrupt obstructive material. For example, in some embodiments the disrupting edges 2614 can be sharpened and/or serrated. In some embodiments, the disrupting element 2604 has a proximal end portion configured to be coupled to a negative pressure source to draw captured obstructive material towards and through gaps between the arms 2612. In some embodiments, one or both of the supporting element 2602 or disrupting element 2604 is not configured to be fluidly coupled to a negative pressure source.

The arms 2612 of the disrupting element 2604 can be configured to rotate relative to the arms 2608 of the supporting element 2602, thereby bringing the disrupting edges 2614 towards an edge 2610 of the supporting element 2602. In so doing, obstructive material becomes trapped between the disrupting edge 2614 and the supporting edge 2610 such that the supporting edge 2610 provides resistance to rotation of the obstructive material with the disrupting edge 2614 and enables the disrupting edge 2614 to cut through the obstructive material. In some embodiments, both the supporting edge 2610 and disrupting edge 2614 are configured to cut and/or penetrate obstructive material. The separated portions of the obstructive material can then be drawn through the lumen of the supporting element 2602 and/or disrupting element 2604 and removed from the body.

Figure 27:
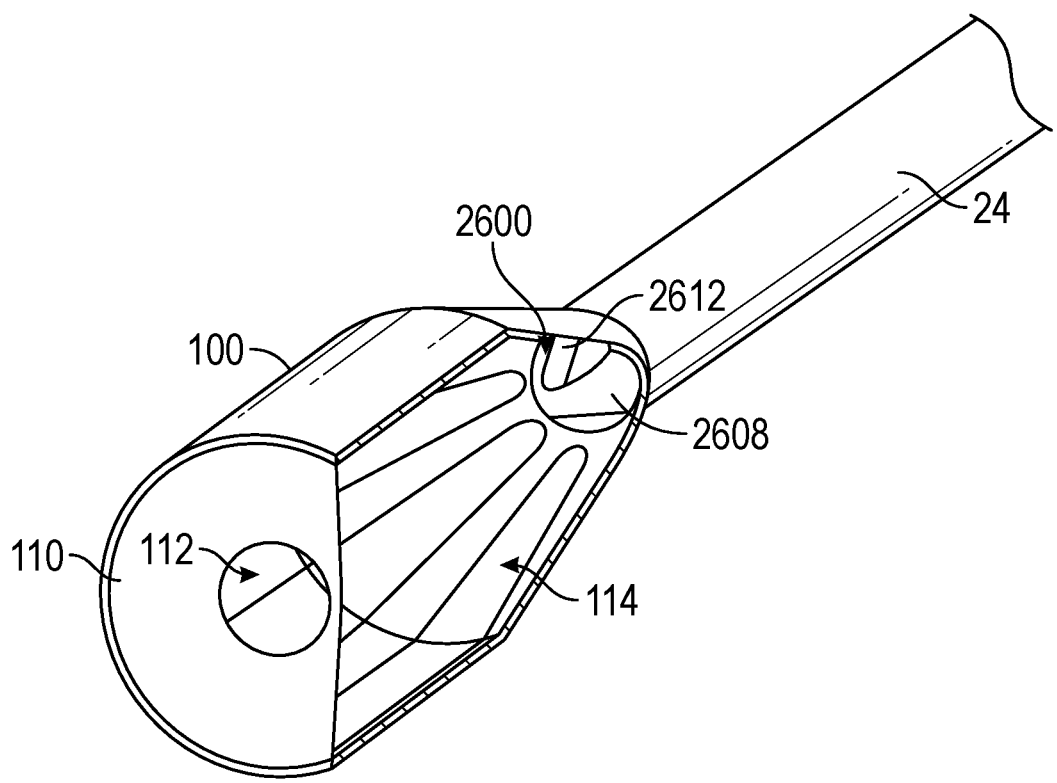

FIG. 27 shows a distal end portion of a treatment system configured in accordance with several embodiments of the present technology, showing the disrupting device 2600 positioned within the capture structure 100. At least a portion of the disrupting device 2600 can be positioned within the interior region 114 of the capture structure 100 such that the arms 2608, 2612 of one or both of the supporting element 2602 and disrupting element 2604 can fully access capture obstructive material (not shown) within the capture structure 100.

Figure 28:
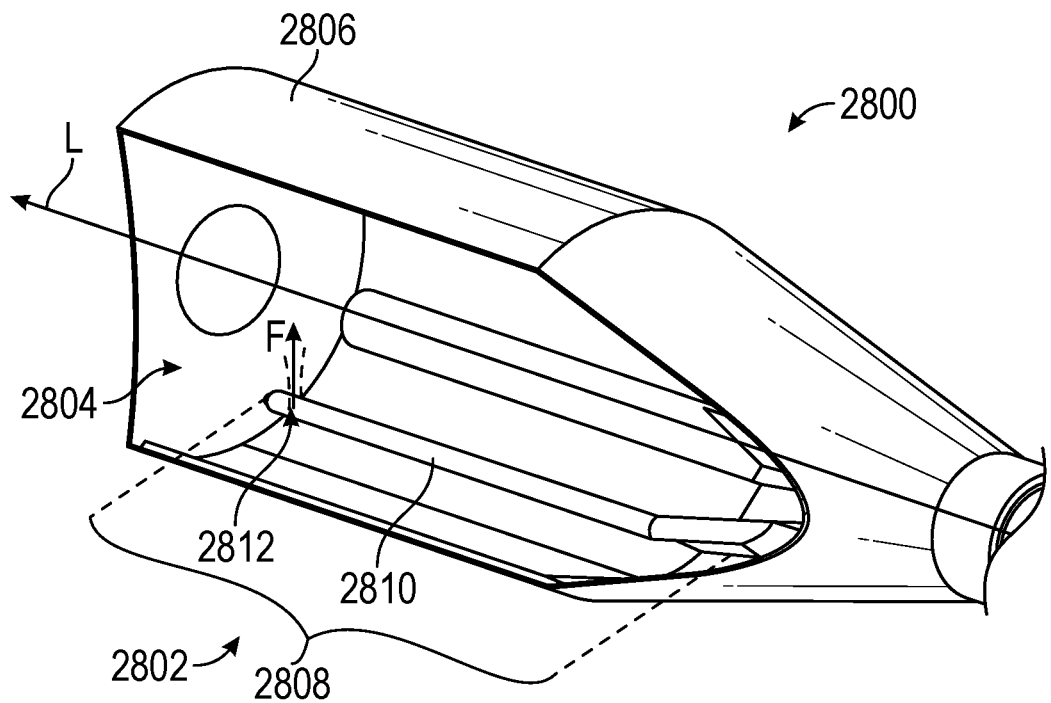
FIG. 28 shows a disrupting device configured in accordance with several embodiments of the present technology.

According to various aspects of the present technology, the treatment system can include a disrupting device configured to hydraulically disrupt obstructive material, rather than (or in addition to) mechanically disrupting the obstructive material. FIG. 28 shows an example distal end of a system 2800 comprising a disruptor 2802 configured to hydraulically disrupt obstructive material. In some embodiments, for example as shown in FIG. 28, a distal region of the disruptor 2802 can be positioned within an interior region 2804 of a capture structure (such as capture structure 100) to deliver fluid to the interior region 2804 and any obstructive material contained therein. The disruptor 2802 can be configured to rotate and/or slide axially relative to the capture structure 100. In some embodiments, an axial and/or rotational position of the disruptor 2802 is fixed relative to the capture structure 100. According to several embodiments, the distal region of the disruptor 2802 can be configured to be positioned within a lumen of the elongated shaft 24 and deliver fluid to the lumen of the elongated shaft 24. In any case, the elongated element 2808 of the disruptor 2802 can be positioned near a sidewall of the capture structure 100 (as shown in FIG. 28) or may extend through the capture structure 100 at a location that is spaced apart from the sidewall.

As shown in FIG. 28, the disruptor 2802 can comprise a hollow elongated element 2808 having a sidewall 2810 defining a lumen and one or more apertures 2812 extending through the sidewall. A proximal portion of the elongated element 2808 can be configured to be coupled to an extracorporeal fluid source, and a distal end of the elongated element 2808 can be closed. In some embodiments, the distal end comprises one or more openings (not shown). In use, fluid flows through the lumen of the elongated element 2808 and into the interior region 2804 through the apertures 2812, thereby disrupting obstructive material within the interior region 2804. The fluid can comprise saline, a lysing agent, a contrast agent, and/or other suitable fluids.

Disruption of obstructive material with fluid can be advantageous in that fewer and/or smaller structural components may be required of the disruptor, thus freeing up more space within the capture structure. Additionally, delivery of pressurized fluid to the interior region 2804 can increase the total pressure acting on obstructive material within the interior region 2804. In some embodiments, the system is configured such that fluid can be delivered to the interior region 2804 of the capture structure 100 while negative pressure is applied to the interior region 2804 to prevent or limit accumulation of the fluid within the interior region 2804. Fluid delivery and aspiration can occur simultaneously and/or independently.

The lumen of the elongated element 2808 can have a diameter of between about 0.01 in and about 0.05 in, between about 0.015 in and about 0.045 in, between about 0.02 in and about 0.04 in, between about 0.025 in and about 0.035 in, less than 0.01 in, about 0.01 in, about 0.015 in, about 0.02 in, about 0.025 in, about 0.03 in, about 0.035 in, about 0.04 in, about 0.045 in, about 0.05 in, or greater than 0.05 in. A thickness of the sidewall of the elongated element 2808 can be between about 0.001 in and about 0.005 in, between about 0.002 in and about 0.004 in, less than 0.001 in, about 0.001 in, about 0.002 in, about 0.003 in, about 0.004 in, about 0.005 in, about 0.003 in or more, or about 0.005 in or more. The elongated element 2808 can comprise a polymer (e.g., polyimide, etc.), a metal, or another suitable material. In some embodiments, the sidewall of the elongated element 2808 can include a reinforcing element such as a braid, a coil, etc.

Fluid can be delivered to the lumen of the elongated element 2808 at a pressure between about 100 psi and about 2000 psi, between about 150 psi and about 1500 psi, between about 200 psi and about 1000 psi, between about 250 psi and about 950 psi, between about 300 psi and about 900 psi, between about 350 psi and about 850 psi, between about 400 psi and about 800 psi, between about 450 psi and about 750 psi, between about 500 psi and about 700 psi, or between about 550 psi and about 650 psi.

The one or more apertures 2812 can have a diameter between about 0.01 in and about 0.05 in, between about 0.015 in and about 0.045 in, between about 0.02 in and about 0.04 in, between about, between about 0.025 in and about 0.035 in, less than 0.01 in, about 0.0.1 in, about 0.02 in, about 0.03 in, about 0.04 in, about 0.05 in, or greater than 0.05 in. Additionally or alternatively, the apertures 2812 can comprise one or more slots and/or slits. The apertures 2812 can have any suitable cross-sectional shape such as, but not limited to, circular, rectangular, triangular, polygonal, etc. In embodiments in which the elongated element 2808 comprises multiple apertures 2812, the apertures 2812 can be separated by a spacing of about 0.01 in, about 0.02 in, about 0.03 in, about 0.04 in, about 0.05 in, or more than 0.05 in.

The longitudinal and circumferential positions of the apertures 2812 along the elongated element 2808 and the angle of the elongated element 2808 relative to the longitudinal axis of the capture structure 100 can be adjusted to direct fluid flow in a desired direction. For example, as shown in FIG. 28, the elongated element 2808 can extend substantially parallel to a longitudinal axis L of the capture structure 100 with at least one aperture 2812 positioned at a circumferential location such that the aperture 2812 faces towards the interior region 2804 of the capture structure 100. Thus, fluid flows away from the aperture 2812 in a direction that is substantially perpendicular to the longitudinal axis L of the capture structure 100. In some embodiments, a distal portion of the elongated element 2808 can be angled relative to the longitudinal axis of the capture structure 100 such that at least some of the fluid flows away from the elongated element 2808 at a non-90 degree angle relative to the longitudinal axis of the capture structure 100. According to several embodiments, the disrupting device 2800 can be configured to deliver fluid into the capture structure 100 and/or elongated shaft 24 along multiple fluid flow paths (see, for example, first fluid flow path F1, second fluid flow path F2, and third fluid flow path F3 in FIG. 29). The fluid flow paths can be spaced apart and/or angled with respect to one another. In some embodiments, the first fluid flow path F1 is angled with respect to the second fluid flow path F2 by about 45 degrees and/or the second fluid flow path F2 is angled with respect to the third fluid flow path F3 by about 45 degrees. In some embodiments, one or more fluid flow paths are directed proximally to facilitate aspiration of obstructive material proximally through the system and out of a patient's body.

Although FIG. 28 depicts one elongated element 2808 with one aperture 2812, the treatment systems of the present technology can comprise any number of elongated elements 2808 (e.g., two elongated elements, three elongated elements, four elongated elements, etc.) or apertures 2812 (e.g., two apertures, three apertures, four apertures, five apertures, six apertures, etc.).

Figure 29:
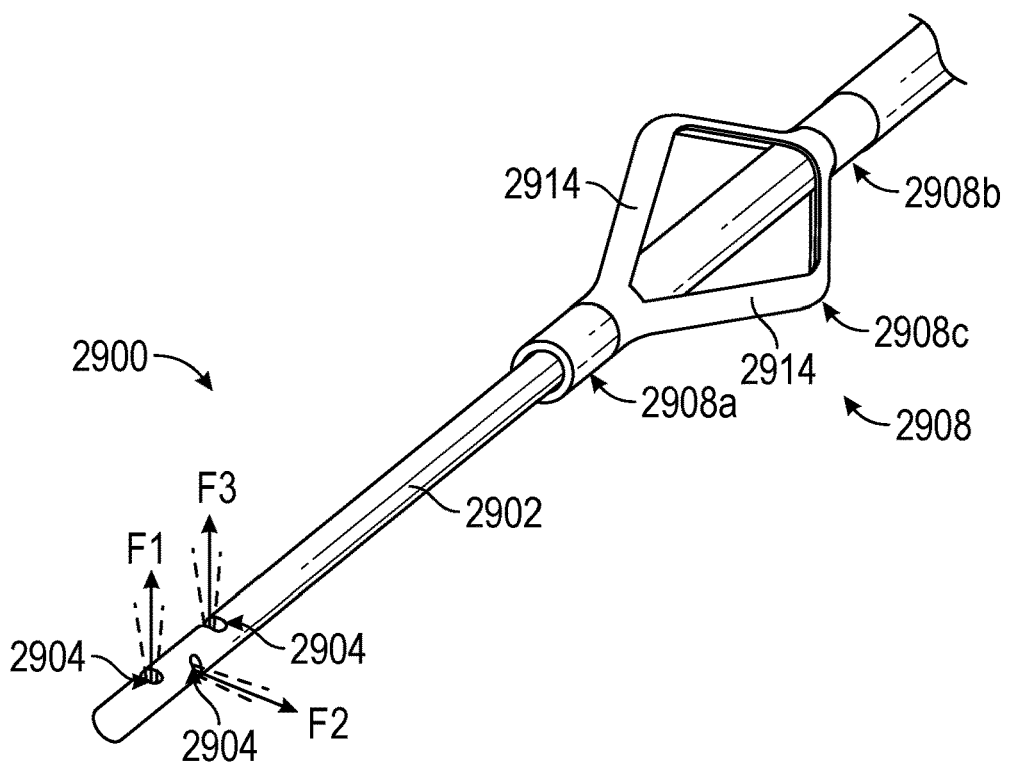
FIGS. 29 and 30 are various views of a disrupting device configured in accordance with several embodiments of the present technology.
Figure 30:
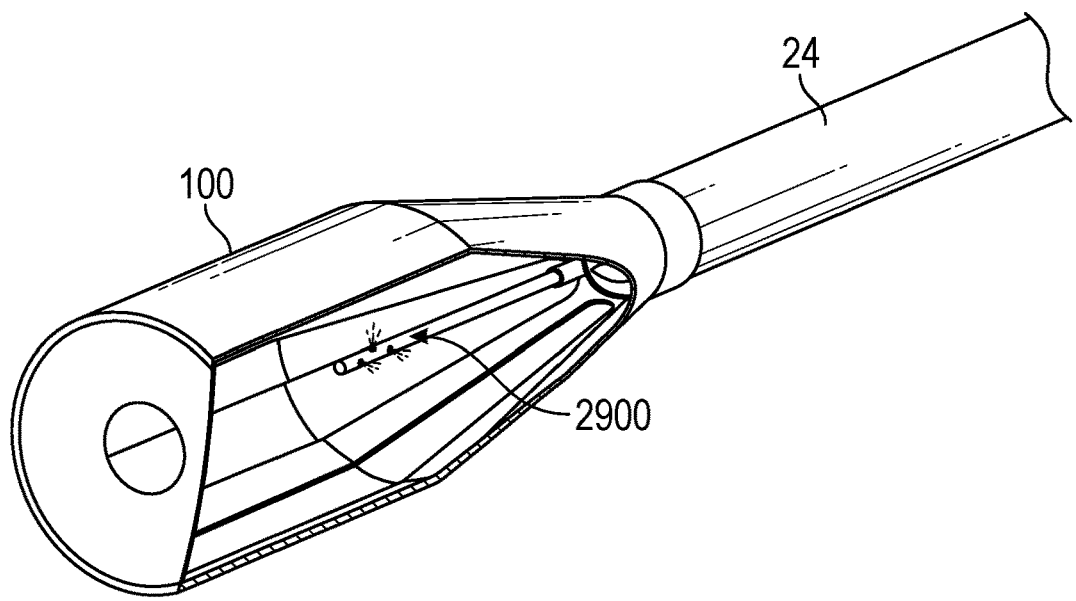

FIG. 29 shows a disrupting device 2900 configured in accordance with the present technology, and FIG. 30 shows the disrupting device 2900 positioned within a capture structure 100. The disrupting device 2900 can comprise an elongated element 2902 having one or more apertures 2904 extending through its sidewall and configured to receive disruptive fluid therethrough. In some embodiments the disrupting device 2900 can include a centering element 2908 slidably or fixedly coupled to the elongated element 2902 of the disrupting device 2900. The centering element 2908 can be configured to facilitate alignment of the disrupting device 2900 with a lumen of the elongated shaft 24 and/or an interior region of the capture structure 100. The centering element 2908 can be similar to any of the centering elements disclosed herein. For example, as shown in FIG. 29, the centering element 2908 can comprise a first end portion 2908a, a second end portion 2908b opposite the first end portion 2908a, and an intermediate portion 2908c, between the first and second end portions 2908a, 2908b. The first and second end portions 2908a, 2908b can be circumferentially continuous while the intermediate portion 2908c can be circumferentially discontinuous such that the intermediate portion 2908c comprises a plurality of struts 2914. Additionally or alternatively, the intermediate portion 2908c can be circumferentially continuous. A cross-sectional dimension of the centering element 2908 at the intermediate portion 2908c can be greater than a cross-sectional dimension of the centering element 2908 at the first end portion 2908a and/or the second end portion 2908b. In some embodiments, a maximum cross-sectional dimension of the centering element 2908 is substantially equivalent to a cross-sectional dimension of the elongated shaft 24. Accordingly, when the centering element 2908 is positioned within the lumen of the elongated shaft 24, the centering element 2908 contacts an inner surface of the elongated shaft 24 such that the disrupting device 2900 is substantially centered within the lumen of the elongated shaft 24 and/or an interior region of the capture structure 100.

It will be appreciated that the centering elements of the present technology can be used with any of the disrupting devices disclosed herein.

Figure 31A:
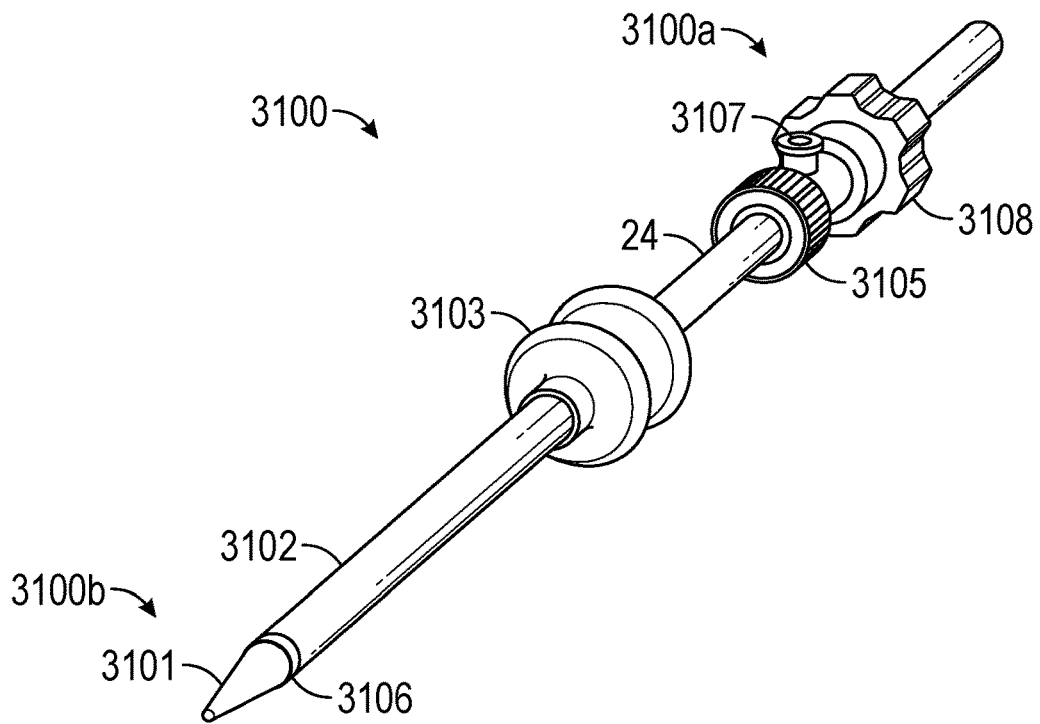
FIG. 31A is an isometric view of a treatment system in a low-profile delivery state configured in accordance with several embodiments of the present technology.

FIGS. 31A-31D show a treatment system 3100 configured in accordance with the present technology. FIG. 31A shows the system 3100 in a low-profile delivery state. The system 3100 has a proximal end portion 3100a and a distal end portion 3100b. The system 3100 can comprise an outer sheath 3102 and an elongated shaft 24 (see FIG. 31B) slidably disposed within a lumen of the sheath 3102. The outer sheath 3102 can have a proximal end region coupled to a slider 3103 and a distal end region. The elongated shaft 3104 can have a proximal end region coupled to a hub or handle 3105 having an aspiration port 3107, a hemostasis valve 3108, and/or other connectors. The system 3100 can further optionally include a dilator 3101, a disrupting device 200 (see FIG. 31C), and a guidewire (not shown). Any of the treatment systems disclosed herein, including treatment systems 1 and 1200, can include a guidewire, a guidewire lumen, and/or a dilator.

In some embodiments, the sheath 3102 comprises a reinforced polymeric shaft. As previously mentioned, the proximal end region of the sheath 3102 can be coupled to a slider 3103 (e.g., thermally or adhesively bonded), and a distal end region of the sheath 3102 can comprise a radiopaque portion 3106. For example, the radiopaque portion 3106 can comprise a radiopaque marker that is coupled (e.g., thermally or adhesively bonded) to an outer surface of the sheath 3102.

Figure 31B:
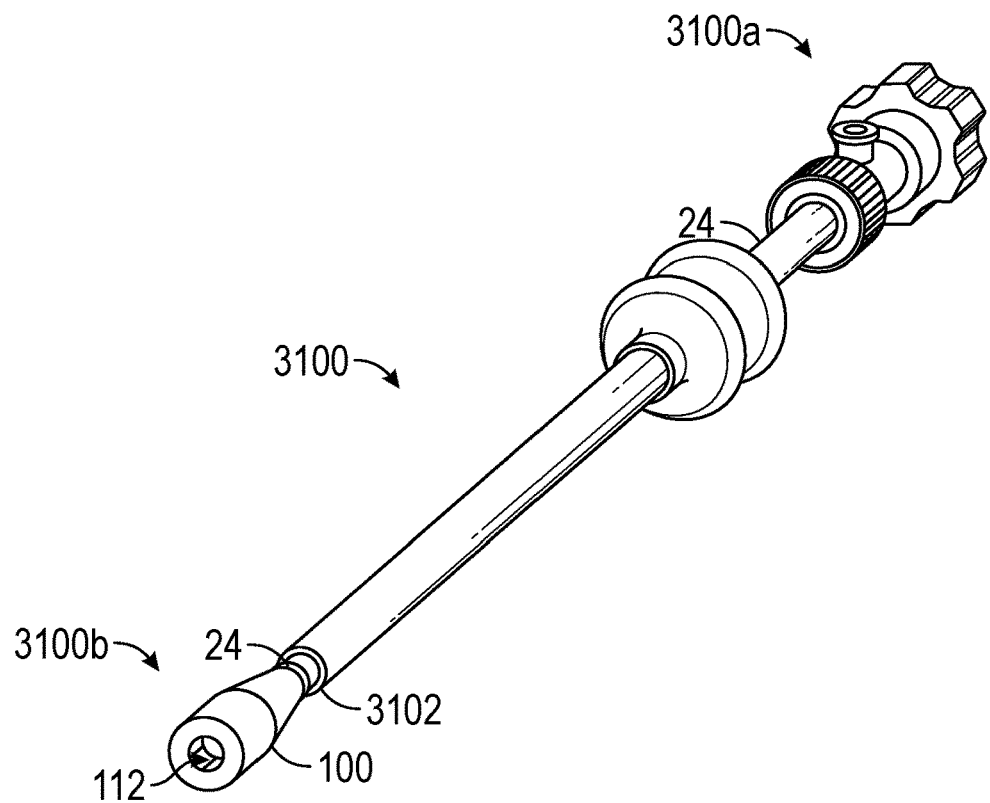
FIG. 31B is an isometric view of the treatment system of FIG. 31A in an expanded state configured in accordance with several embodiments of the present technology.
Figure 31C:
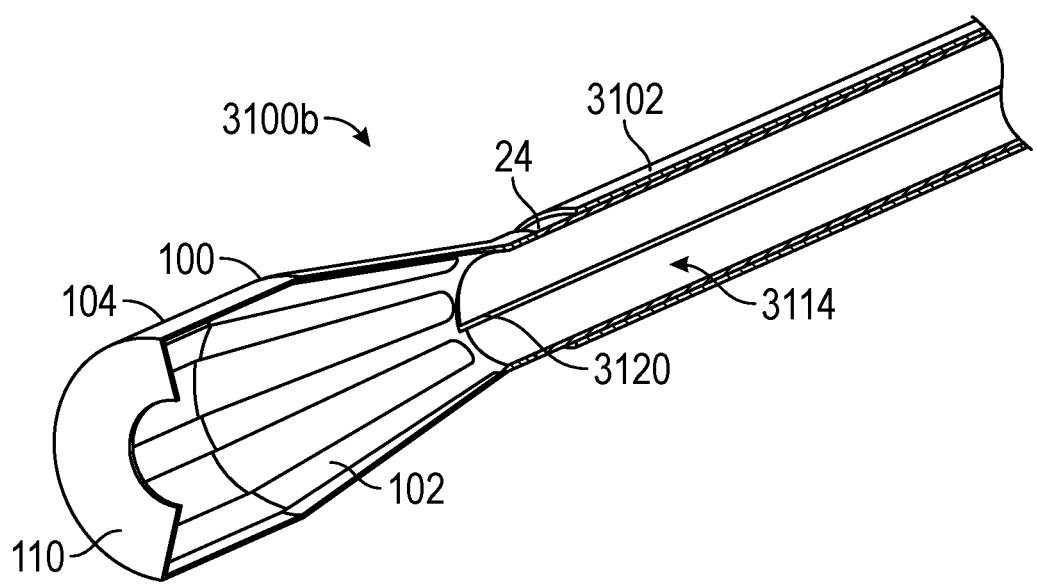
FIG. 31C is an enlarged, cross-sectional view of a distal portion of the treatment system shown in FIG. 31B.

FIG. 31B shows the system 3100 with the dilator 3101 removed and the sheath 3102 withdrawn such that the capture structure 100 is in an expanded state. FIG. 31C shows the orifice 112, the expandable frame 102, the cover 104 comprising the capture structure 100. As is true for any of the expandable frames disclosed herein, the expandable frame 102 can be made from a hypotube (superelastic and/or resilient, or not). In some embodiments, the frame 102 can be made of polymeric or metallic weave or other expandable elements as described herein. As is true for any of the covers disclosed herein, the cover 104 can be a highly conformable material with a wall thickness of less than 0.50 mm, less than 0.40 mm, less than 0.38 mm, less than 0.30 mm, less than 0.20 mm, and others. In some embodiments, the cover 104 is made from a thermal plastic elastomer, such as a thermal plastic polyurethane having a hardness less than 65 Shore D.

FIG. 31C shows an example of a disrupting device 200 having an elongated portion and a disruptor 3120 at the distal end of the elongated portion. The disrupting device 200 can be positioned relative to the elongated shaft 24 such that the disruptor 3120 is located within the interior region of the capture structure 100. Any of the disrupting devices disclosed herein can be used with the system 3100. Moreover, any of the capture structures disclosed herein can be used with the system 3100.

Figure 31D:
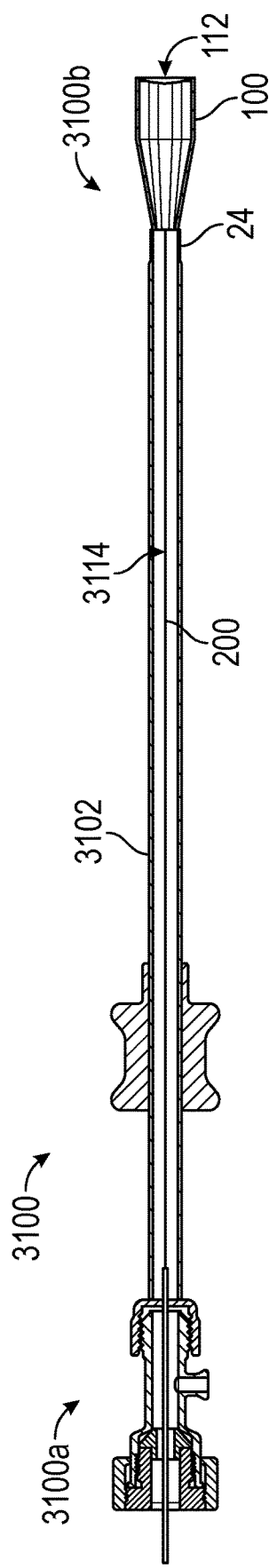
FIG. 31D is a side cross-sectional view of the treatment system shown in FIG. 31B.

FIG. 31D provides a cross-sectional view of the system 3100 and shows the lumen 3114 of the elongated shaft 3102. As previously discussed, the lumen 3114 fluidly connects the stretchable orifice 112 to the channels within the handle.

According to several aspects of the present technology, the elongated shaft 24 and/or sheath 22 can together or separately be configured for directional steering. Such a feature can be beneficial for navigating the tortuous anatomy and/or directing the capture structure 100, engagement wall 110, and/or opening 112 to engage obstructive material in the vessel lumen. The distal portion of any of the elongated shafts disclosed herein, including elongated shaft 24, can be configured to bend, flex, or otherwise articulate in a predetermined manner. For example, in some embodiments the elongated shaft 24 and/or sheath 22 includes a manipulation member having a first end coupled to an actuator at a corresponding handle and a second end coupled to a distal portion of the corresponding elongated shaft 24 and/or sheath 22. The articulation enables the operator to actively steer the distal portion of the elongated shaft 24 and/or sheath 22 through the vascular anatomy as well as span the entire vessel wall of larger vessels, such as the main pulmonary artery. The articulation directs the centerline of at least a portion of the distal section and or orifice at least 5 degrees from the centerline of the proximal section of the central lumen. In some embodiments, a portion of the distal region of the elongated shaft 24 and/or sheath 22 has a preset curve of a desired radius so that, at rest, the centerline of the portion is at least 5 degrees from the centerline of the proximal portion of the corresponding elongated member and less than 270 degrees from the proximal centerline. In such embodiments, the curved distal portion is then covered with an outer sheath to align the centerline of the distal portion with the centerline of the proximal portion. The outer sheath is then retracted axially to expose a portion of the curved distal portion, causing the centerline of the distal portion to angle away from the centerline of the proximal portion of the corresponding elongated shaft 24 and/or sheath 22.

Figure 32:
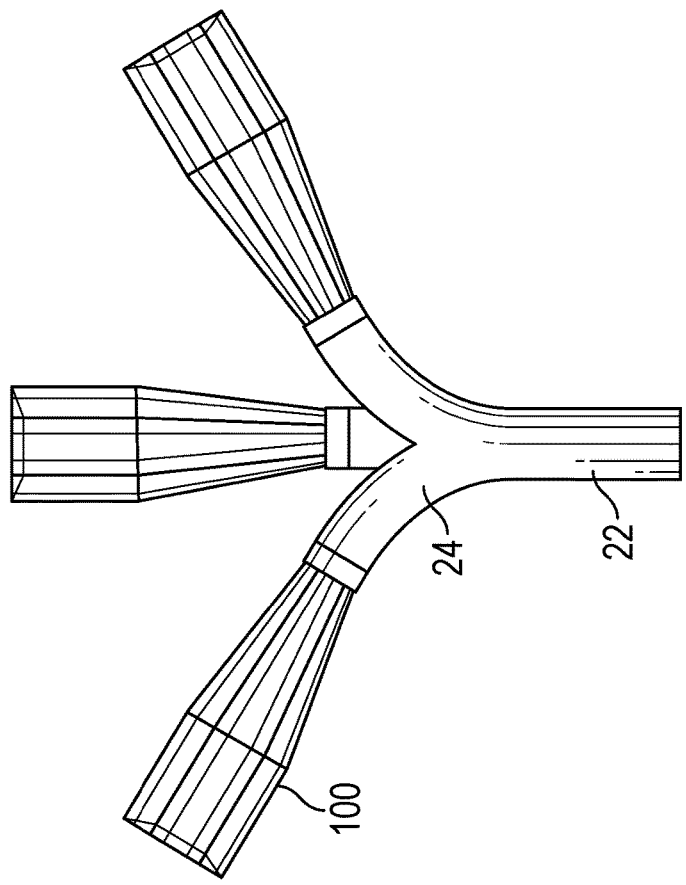
FIG. 32 shows an articulating distal portion of a treatment system configured in accordance with several embodiments of the present technology.

In some embodiments, the elongated shaft 24 and/or sheath 22 is configured to bend at its distal portion. The elongated shaft 24 and/or sheath 22 can be configured to automatically assume a desired bending angle upon release from a restraint, such as a release wire or outer sheath. Such a preset bend in the elongated shaft 24 and/or sheath 22 can be achieved by coldworking, heat treatment, selective etching, and/or selective removal of material from the elongated shaft 24 and/or sheath 22 to impart preferential bending towards the desired angle. In some embodiments, the system can comprise an outer sheath (such as sheath 2602) configured to be translated relative to the elongated shaft 24 and/or sheath 22 to axially to expose more or less of the bendable portion to achieve more or less of a preset bending angle. The sheath 22, for example, can be used to selectively expose portions of the elongated shaft 24 to achieve a desired bending of the elongated shaft 25. In these and other embodiments, the elongated shaft 24 and/or sheath 22 can be configured to be manually manipulated and/or activated into a bent configuration. FIG. 32 depicts an example treatment system having an elongated shaft 24 configured to bend at its distal portion. The bending location is positioned proximal to the capture structure 100, thereby allowing the system to direct the entire capture structure 100 towards the intended target (such as obstructive material).

Figure 33A:
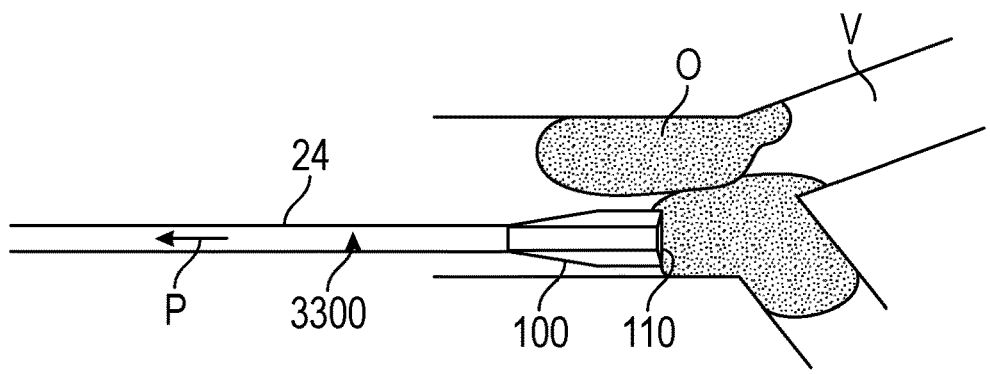
FIGS. 33A-33C illustrates a method for disrupting and/or extracting obstructive material from a vessel lumen using the treatment system shown in FIGS. 31A-31D.
Figure 33B:
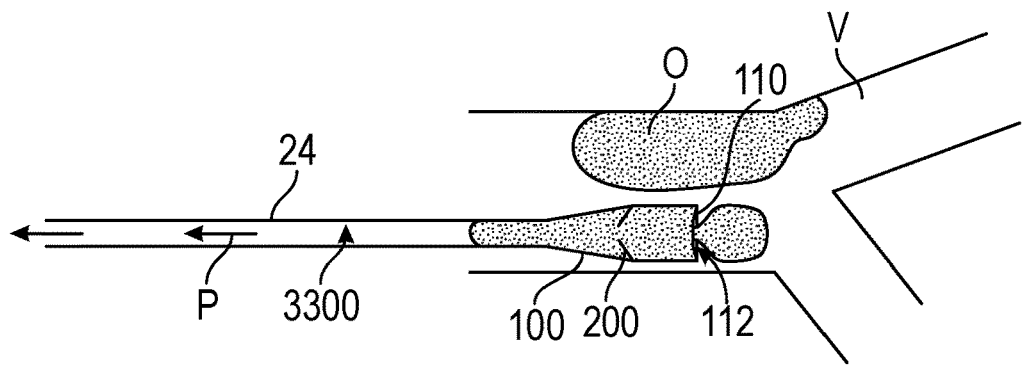
Figure 33C:
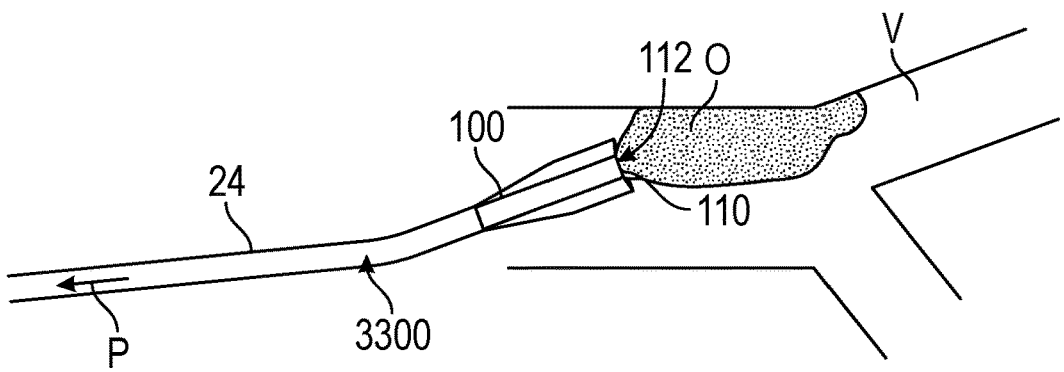

An example method for using a treatment system comprising distal bending is illustrated in FIGS. 33A-33C. The system can be advanced into the vascular anatomy V and positioned proximal to obstructive material, such as obstructive material O. As shown in FIG. 33A, the capture structure 100 can be expanded at the treatment site and engage the thrombus O by (a) advancement of the engagement surface 110 on and over the obstructive material O, by (b) applying negative pressure through the opening 112, or both (a) and (b). In any case, engagement with the obstructive material O causes at least a portion of the obstructive material O to extend through the opening 112 and into the interior region of the capture structure 100, as shown in FIG. 33B. The engagement surface 110 surrounding the opening 112 can apply a radially inward force on the obstructive material O positioned within the opening 112 to retain the obstructive material O within the interior region of the capture structure 100. As shown in FIG. 33B, in some embodiments the system includes a disrupting device comprising a disruptive element and/or disruptor 200 that engages with the obstructive material O. The disrupting device can be configured to disrupt the obstructive material via axial translation of the obstructive material O relative to the disruptor 200 and/or the disruptor 200 relative to the capture structure 100, or both, or by another disruption means and/or using another disrupting device, such as any of the disrupting devices described herein. Such disruption can occur as negative pressure P is applied through a lumen of the elongated shaft 24, thereby urging the obstructive material O proximally through the lumen 3300 and out of the body.

In some methods of use, for example as shown in FIG. 33C, the distal portion of the system, including capture structure 100, can be steered towards additional obstructive material O within the same vascular anatomy V. Once the capture structure 100, engagement surface 110, and/or opening 112 is aligned with the obstructive material O, a negative pressure P can be applied and the process of digesting the obstructive material O and passing it through the lumen 3300 of the elongated shaft 24 of the system can be repeated. The system (and any component thereof) can be repositioned as many times as required.

In any of the embodiments disclosed herein, a proximal portion of the elongated shaft 24 and/or sheath 22 can be stiffer than the distal portion and can have a crossing profile of less than 8 mm. The wall construction can be optimized to withstand a negative pressure of at least 200 mmHg and have a wall thickness of less than 0.5 mm. The proximal portion of the elongated shaft can be constructed from metallic hypotubes, multi-filament braids, and/or flat ribbon and round wire coils encapsulated by polymeric material. The inner layer that surrounds and defines the central lumen can comprise a lubricious material and/or be coated with a hydrophilic or other lubricious coating. The proximal end of the proximal portion is designed to be affixed to a handle. The proximal end can be fluidly connected to at least one port within the handle. In some embodiments, the proximal portion has an additional opening on the side wall and the central lumen is fluidically connected to the central lumen.

Any of the second hubs 44 disclosed herein can include at least two channels that are configured to be fluidically connected to the lumen of the elongated shaft.

In some aspects of the technology, the system includes a vascular access and therapy catheter. It has an outer diameter of less than 30 Fr during insertion and placement to the therapeutic site in the vascular anatomy. It has a length of between 50 and 200 cm. In an initial configuration in maintains an atraumatic insertion profile to minimize/eliminate vascular damage to vessels, vessel walls, valves of the veins, valves and chambers of the heart. A tapered atraumatic removable dilator may be used during placement to augment creating a streamlined insertion profile. The catheter and/or catheter/dilator can accommodate in a slidable and removable fashion guidewires of diameters of 0.020 to 0.038 in. The catheter can accommodate accessory instrumentation in its lumen and to or beyond its distal section during insertion, navigation, or in its therapeutic position. The accessory instrumentation may be for various therapeutic needs. This may include catheters for the delivery of fluids such as saline, lysing agents, and radiological contrast into the sheath, through the sheath, and beyond the catheter. This may include accessories to extend beyond the sheath to help the pushability and or directability of guidewires: for example, an angled tip catheter over and coaxial to the guidewire that would direct the trajectory of the guidewire due to the amount of angled length extended and or twisting of the angled tip catheter, or active angulation or steering. The instrumentation may include accessories to help clear blockages from the sheath lumen or sheath distal tip features. These instruments may be configured to mechanically break up obstructive material, like instruments such as thrombectomy balloons, elongated shafts with bulbous tips that disrupt the clot or de-clog the sheath lumen, elongated shafts with brush-like distal structures, elongated shafts with expanding engagement tips, elongated shafts with cutting or slicing tips, elongated shafts with grasping tips, elongated shafts with suction engagement tips, elongate shafts that supply therapeutic or diagnostic energy such as cryo, ultrasound, radiofrequency, vibration, visualization, heat, electrical sensing, magnetic sensing, impedance sensing, thermal sensing, chemical sensing, and/or other instrumentation. The accessory catheter-like instruments may be disposed coaxially on a guidewire, rapid exchange on a guidewire, or parallel to a guidewire in the sheath lumen. Additionally they may be placed into and/or through the sheath in the absence of a guidewire.

According to some embodiments, one, some, or all of the proximal hubs can have a variable orifice fluid tight seal to maintain hemostasis in the absence of accessories in the sheath lumen and to seal against accessories in the sheath lumen.

The elongated shaft, sheath, and/or dilator (together or individually) can be optimized for pushability, torquability, flexibility, kink/crush resistance to track/navigate from a femoral or jugular percutaneous site, across the vena cava, through the right atrium, through the tricuspid valve, across the right ventricle, through the pulmonary valve, into the pulmonary artery, and into the right and left branches of the pulmonary vasculature from the first and preferably to the secondary and tertiary branches. The elongated shaft, sheath, and/or dilator (together or individually) can be configured resist collapse against internal vacuum pressures of at least 200 mmHg. This can be accomplished by, for example, composite tubular structures such as polymers encapsulating braids, coils, metallic tubes cut with material removal patterns that allow flexibility.

Figure 34A:
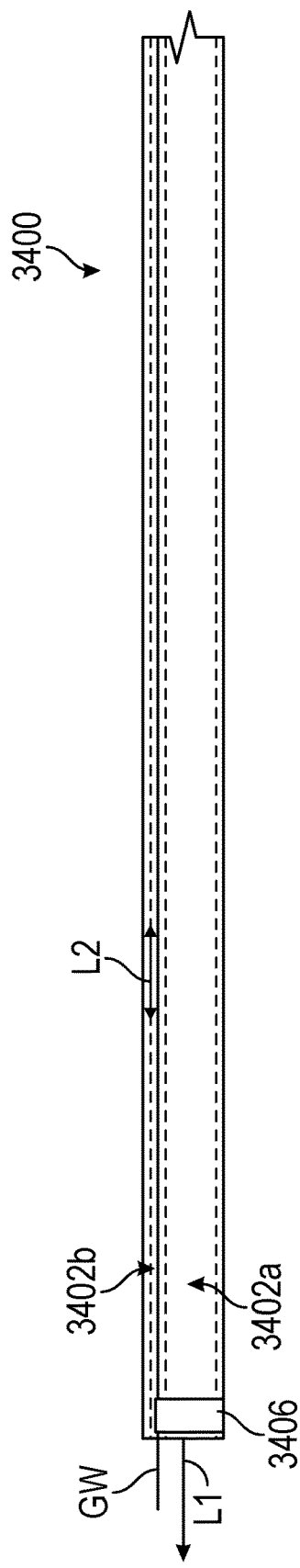
FIGS. 34A and 34B show a treatment system configured in accordance with several embodiments of the present technology.
Figure 34B:
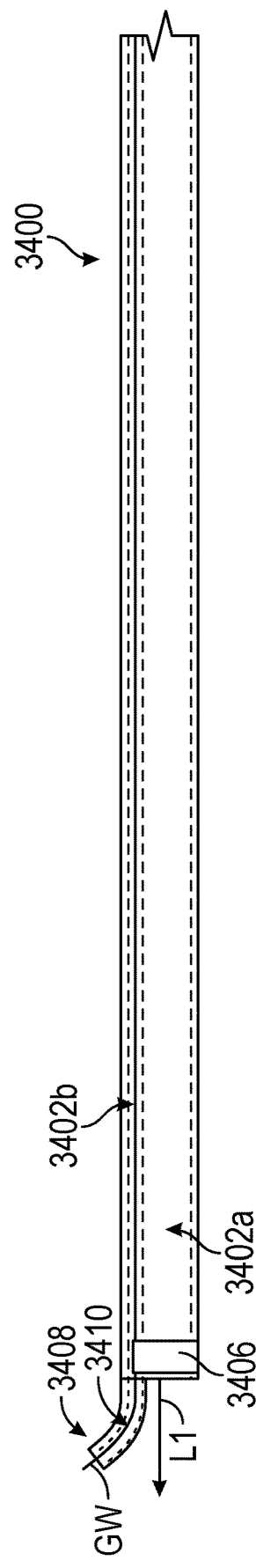

The capture structure 100, elongated shaft 24, sheath 22, and/or dilator (together or individually) can be passively tracked on a guidewire into position. In some embodiments, the capture structure, elongated shaft, sheath, and/or dilator can have one or more lumens configured to receive the guidewire. For example, FIGS. 34A and 34B show a sheath 3400 having a first lumen 3402a and a second lumen 3402b (collectively "lumens 3402"). The sheath 3400 can have a first end portion, a second end portion, and a longitudinal axis L1 extending between the first and second end portions. The first lumen 3402a can be configured to receive one or more components of the system (e.g., the elongated shaft 24, the sheath 22, an aspiration catheter, a disrupting device, etc.) therethrough, while the second lumen 3402b can be configured to receive a guidewire GW therethrough. In some embodiments, a longitudinal axis L2 of the second lumen 3402b can be substantially parallel to the longitudinal axis L1 of the sheath 3400 (see FIG. 34A). In some embodiments, the sheath 3400 can include a marker 3406 configured to facilitate visualization of the sheath 3400 once intravascularly positioned.

As shown in FIG. 34B, the first end portion of the sheath 3400 can include a protrusion 3408 having a lumen 3410 extending therethrough that is aligned with and open to the second lumen 3402b. Accordingly, the guidewire GW can be inserted into the second lumen 3402b and advanced into and through the lumen 3410 of the protrusion 3408 such that the lumen 3410 of the protrusion 3408 guides the guidewire GW along a desired path, thereby enhancing navigability of the system.

Figure 35:
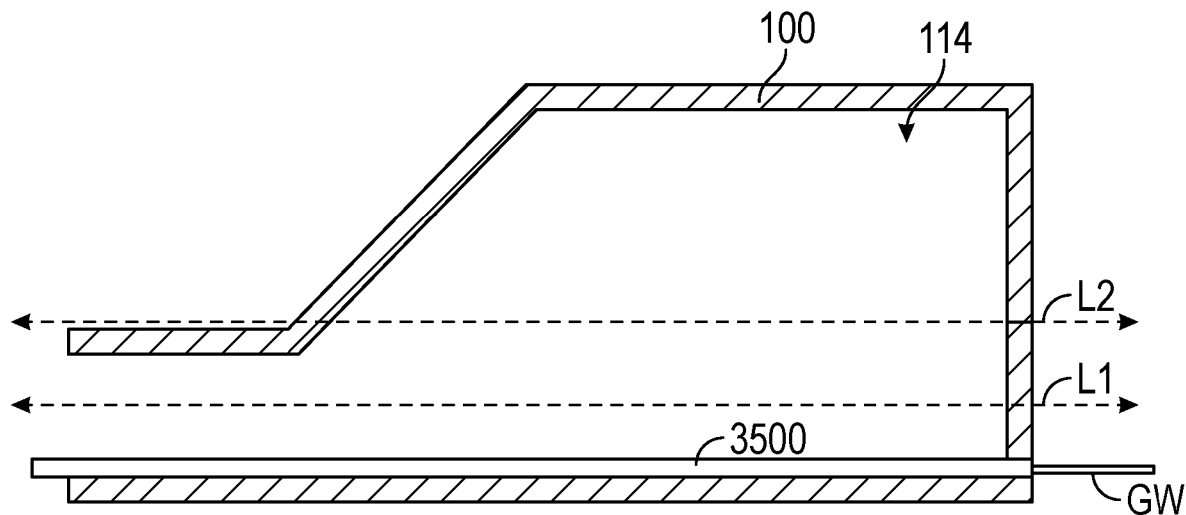
FIG. 35 shows the distal portion of a treatment system configured in accordance with several embodiments of the present technology.
Figure 36:
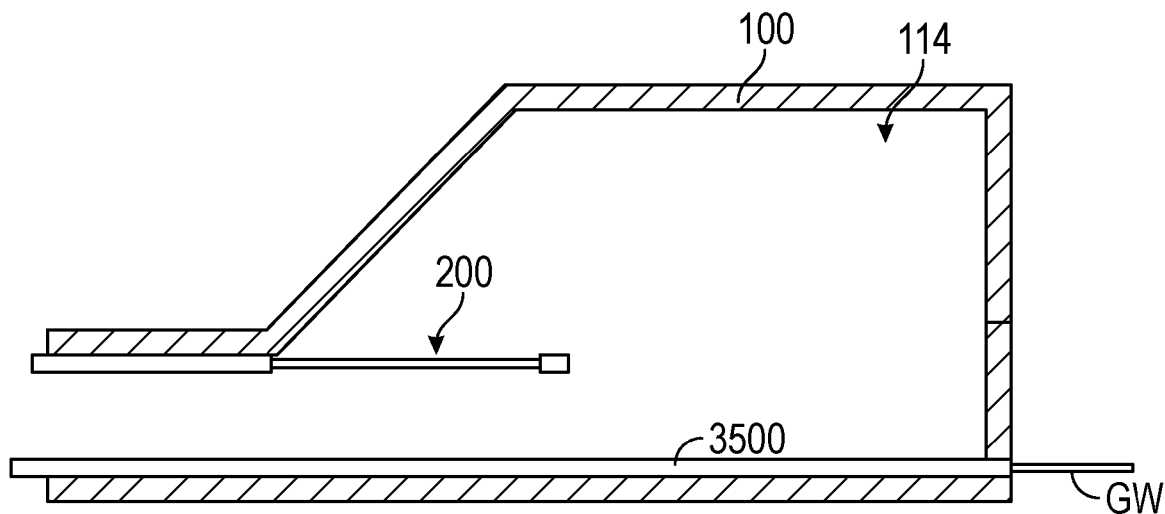
FIG. 36 shows the distal portion of a treatment system configured in accordance with several embodiments of the present technology.

FIG. 35 shows a distal portion of a treatment system including a guidewire channel 3500 extending through the elongated shaft (not shown) and capture structure 100. The guidewire channel 3500 can be positioned within the lumen 114 of the capture structure 100 such that the channel 3500 is offset from the central longitudinal axis L1 of the elongated shaft 24 and the central longitudinal axis L2 of the capture structure 100. In some embodiments, the guidewire channel can extend through the central longitudinal axis of the elongated shaft 24 and/or capture structure 100. In any of the foregoing embodiments, the disrupting device (if used) can be configured to track over the guidewire and/or through the guidewire channel and/or lumen. In some embodiments, for example as shown in FIG. 36, the system includes a separate channel 3600 and/or lumen for the disrupting device 200 (i.e., the disruptive device 200 is not configured to be slidably positioned in the guidewire channel and/or lumen).

Any of the foregoing embodiments, including those with preferential bending and/or directional steering, can be configured for use with a guidewire.

According to several embodiments, the treatment systems of the present technology are configured to extract large thrombi from a pulmonary artery in a patient suffering from pulmonary embolism. In some embodiments, a large thrombus can have a cross-sectional dimension of at least 5 mm. For example, the large thrombi can have a cross-sectional dimension of between about 8 mm and about 30 mm. Such thrombi may be sufficiently large such that the thrombi cannot be readily aspirated into an interventional device without mechanical disruption. A treatment system can include an elongated shaft and a capture structure carried by a distal region of the elongated shaft and configured to be positioned in a blood vessel lumen proximate the obstructive material. The capture structure can comprise a sidewall that surrounds and defines an interior region that is sized to receive and contain obstructive material. The sidewall can be substantially impermeable to fluids, except for a small orifice extending through the thickness of the sidewall. The capture structure can be fluidly coupled to a negative pressure source (via the elongated shaft) to pull obstructive material through the orifice and into the interior region, and ultimately through the elongated shaft and out of the body. The orifice can have a cross-sectional dimension that is smaller than the cross-sectional dimension of the interior region of the capture structure to prevent escape of obstructive material once the material has been pulled into the interior region. In some embodiments, the treatment system can also include a disruptor configured to be positioned within the interior region of the capture structure to mechanically break up obstructive material that has been pulled or otherwise forced into the interior region for easy extraction through the elongated shaft.

According to several aspects of the present technology, a method for disrupting and/or removing obstructive material (such as a thrombus) from a blood vessel comprises accessing the vascular anatomy at a remote location from the thrombus, navigating and positioning the distal region of the elongated shaft proximal to the thrombus with the capture structure in a collapsed configuration, expanding the capture structure to a second radial profile greater than the first radial profile used for navigating, and engaging the thrombus with the sidewall of the capture structure. Some methods include applying a negative pressure through the lumen of the elongated shaft and interior region of the capture structure to pull the thrombus proximally within the capture structure and elongated shaft. In some embodiments, the method includes deforming at least the portion of the sidewall surrounding the orifice to accommodate movement of the larger thrombus through the smaller orifice.

Several methods of the present technology further include disrupting the thrombus with a disrupting element positioned within the interior region of the capture structure. In some embodiments, the disrupting element mechanically modulates the negative pressure within the lumen of the elongated shaft and interior region of the capture structure. In some embodiments, the disrupting element mechanically macerates the thrombus as it enters the lumen of the elongated shaft and/or interior region of the capture structure. In some embodiments, the disrupting element mechanically engages and pulls the thrombus through the elongated shaft and/or interior region of the capture structure. In some embodiments, the thrombus is advanced through the orifice in the sidewall of the capture structure and at least partially into the interior region of the capture structure prior to the negative pressure being applied. In some embodiments, the capture structure applies a radial compressive force to the thrombus within the interior region. In some embodiments, the capture structure is actively steered through the vascular anatomy using at least one pull wire. In some embodiments, the orifice in the sidewall of the capture structure applies a retaining force on the thrombus as the thrombus is advanced into the lumen of the elongated shaft. In some embodiments, the capture structure is repositioned within the vessel without advancing the elongated shaft.

CONCLUSION

Although many of the embodiments are described above with respect to systems, devices, and methods for disrupting and/or removing thrombus from a vessel lumen, the technology is applicable to other applications and/or other approaches, such as disruption and/or removal of any obstruction from any body lumen. For example, the devices, systems, and methods disclosed herein can be used for removing thrombus from the peripheral vasculature. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-36.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the term "and/or" includes any and all combinations of one or more of the associated listed items and may be abbreviated as "/". Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

We claim:

1. A device, the device comprising:
   an elongated shaft having a proximal portion, a distal portion, and a lumen extending therebetween, wherein the distal portion is configured to be positioned at a treatment site within a lumen of a pulmonary blood vessel, proximate a clot material; and
   an expandable enclosure defined by a fluid impermeable wall and carried by the distal portion of the elongated shaft, the enclosure extending longitudinally between a first end portion and a second end portion and having an opening at the first end portion that is fluidly coupled to the lumen of the elongated shaft, wherein, at least when the enclosure is in an expanded state, the enclosure has a cross-sectional dimension greater than a cross-sectional dimension of the elongated shaft and defines an interior region configured to receive captured clot material, and
   wherein the wall comprises an engagement portion at least partially covering a distal end of the expandable enclosure and is configured to engage clot material at the treatment site and an aperture extending through the engagement portion, wherein the engagement portion is configured to flex inwardly into the interior region and deform in response to engaging the clot material such that the aperture enlarges.

2. The device of claim 1, wherein, when the engagement portion of the wall is in a resting state, the aperture is closed.

3. The device of claim 1, wherein a proximal portion of the elongated shaft is configured to be fluidly coupled to a negative pressure source to apply a negative pressure within the enclosure.

4. The device of claim 3, wherein the engagement portion of the wall is configured to deform in response to the application of negative pressure.

5. The device of claim 1, wherein the engagement portion of the wall surrounding and defining the aperture is configured to apply a radially compressive force on clot material positioned within the aperture.

6. The device of claim 1, wherein the wall comprises:
   a first region extending longitudinally between the opening and the second end portion, and
   wherein the engagement portion of the wall extends at an angle relative to a long axis of the expandable enclosure.

7. The device of claim 1, wherein the aperture is a slit.

8. The device of claim 1, wherein the wall comprises a proximal tapered portion.

9. A device, the device comprising:
   an elongated shaft having a proximal portion, a distal portion, and a lumen extending therebetween, wherein the distal portion of the elongated shaft is configured to be positioned at a treatment site within a lumen of a blood vessel; and
   a distal housing having a first end region coupled to the distal portion of the elongated shaft, a second end region, and a longitudinal axis extending therebetween, wherein the distal housing is configured to expand to a cross-sectional dimension greater than a cross-sectional dimension of the elongated shaft, wherein the distal housing comprises a wall having a longitudinal portion extending between the first end region and the second end region, and an engagement portion extending radially inwardly from the longitudinal portion at the second end region and having an aperture extending therethrough, wherein, at least when the distal housing is in an expanded state, the longitudinal portion and engagement portion together enclose an interior region configured to receive an obstructive material, and wherein the engagement portion is configured to flex inwardly into the interior region and deform in response to engagement with the obstructive material, and wherein such deformation causes the aperture to enlarge.

10. The device of claim 9, wherein the interior region of the distal housing is in fluid communication with the lumen of the elongated shaft.

11. The device of claim 9, wherein the engagement portion of the wall surrounding and defining the aperture is configured to apply a radially compressive force on the obstructive material positioned within the aperture.

12. The device of claim 9, wherein the wall is substantially impermeable to fluids.

13. The device of claim 12, wherein a proximal portion of the wall is tapered.

14. The device of claim 9, wherein a cross-sectional dimension of the interior region increases or remains constant in a direction towards the second end region of the distal housing.

15. The device of claim 9, wherein a maximum cross-sectional dimension of the interior region of the distal housing is at least two times greater than the cross-sectional dimension of the lumen of the elongated shaft.

16. The device of claim 9, wherein the longitudinal portion of the wall has a first end coinciding with the first end region of the distal housing and a second end surrounding an opening, the opening having a cross-sectional dimension equivalent to the cross-sectional dimension of the interior region, and wherein the engagement portion of the wall extends across the opening.

17. The device of claim 9, wherein the aperture is a slit.

18. A device, the device comprising:
an enclosure configured to be positioned at a treatment site within a pulmonary blood vessel lumen proximate a clot material, the enclosure having a first end region configured to be carried by a distal portion of an elongated shaft, a second end region, and a longitudinal axis extending therebetween, wherein the enclosure is configured to expand at the treatment site to a cross-sectional dimension greater than a cross-sectional dimension of the elongated shaft, wherein the enclosure comprises a fluid impermeable wall that, at least when the enclosure is in an expanded state, defines an interior region and has: (a) a main body extending between a proximal end at the first end region and a distal end, (b) a clot-engaging face extending across the distal end of the main body and coinciding with the second end region of the enclosure, and (c) an aperture extending through the clot-engaging face, wherein the clot-engaging face is configured to flex inwardly into the interior region and stretch in response to engagement with the clot material to enlarge the aperture to allow clot into the enclosure.

19. The device of claim 18, wherein the enclosure comprises an expandable frame and a cover disposed on the expandable frame.

20. The device of claim 18, wherein the main body comprises a proximal region and a distal region, and wherein the cross-sectional dimension of the enclosure increases distally along the proximal region of the main body.

21. The device of claim 20, wherein the enclosure is tapered.

22. The device of claim 18, wherein a maximum cross-sectional dimension of the interior region of the enclosure is at least two times greater than a cross-sectional dimension of a lumen of the elongated shaft.

23. The device of claim 18, wherein the clot-engaging face is resiliently deformable such that, upon disengagement with the clot material, the clot-engaging face relaxes and returns to its pre-engagement configuration.

24. The device of claim 18, wherein the aperture is a slit.

25. A device, the device comprising:
an elongated shaft having a proximal end portion, a distal end portion, and a lumen extending therebetween, wherein the distal end portion of the elongated shaft is configured to expand from a collapsed delivery state to an expanded state for engaging and capturing an obstructive material, and wherein, at least in the expanded state, an average cross-sectional dimension of the distal end portion of the shaft is greater than the average cross-sectional dimension of the rest of the shaft, wherein the shaft includes an engagement surface extending radially across a distal face of the distal end portion and at least partially covering the distal end portion such that a sidewall of the shaft along the distal end portion and the engagement surface together define an interior capture region, the engagement surface having an aperture extending therethrough, and wherein the engagement surface is configured to flex inwardly into the interior capture region and stretch and relax to increase and decrease, respectively, the size of the aperture to allow clot into the interior capture region.

26. The device of claim 25, wherein a proximal portion of the elongated shaft is configured to be fluidly coupled to a negative pressure source to apply a suction force through the aperture.

27. The device of claim 26, wherein the engagement surface is configured to deform in response to the application of negative pressure.

28. The device of claim 25, wherein a maximum cross-sectional dimension of the interior capture region of the distal end portion is at least two times greater than a cross-sectional dimension of the lumen of the rest of the elongated shaft.

29. The device of claim 25, wherein a portion of the engagement surface surrounding and defining the aperture is configured to apply a radially compressive force on obstructive material positioned within the aperture.

30. The device of claim 25, wherein the aperture is a slit.

* * * * *